(12) United States Patent
Rollins et al.

(10) Patent No.: US 8,945,565 B2
(45) Date of Patent: *Feb. 3, 2015

(54) METHODS OF TREATING INFLAMMATORY OR THROMBOTIC CONDITIONS WITH ANTI-P-SELECTIN ANTIBODIES

(75) Inventors: Scott Rollins, Oklahoma City, OK (US); Richard Alvarez, Edmond, OK (US); Russell Rother, Oklahoma City, OK (US); Rodger P. McEver, Oklahoma City, OK (US); Ziad S. Kawar, Oklahoma City, OK (US)

(73) Assignees: Selexys Pharmaceuticals Corporation, Oklahoma City, OK (US); Oklahoma Medical Research Foundation, Oklahoma City, OK (US)

(*) Notice: Subject to any disclaimer, the term of this patent is extended or adjusted under 35 U.S.C. 154(b) by 0 days.

This patent is subject to a terminal disclaimer.

(21) Appl. No.: 12/974,739

(22) Filed: Dec. 21, 2010

(65) Prior Publication Data

US 2011/0293617 A1 Dec. 1, 2011

Related U.S. Application Data

(63) Continuation-in-part of application No. 12/516,987, filed as application No. PCT/US2007/024692 on Nov. 30, 2007, now Pat. No. 8,377,440.

(60) Provisional application No. 60/872,170, filed on Dec. 1, 2006.

(51) Int. Cl.
*A61K 39/395* (2006.01)
*C07K 16/28* (2006.01)

(52) U.S. Cl.
CPC ......... *C07K 16/2896* (2013.01); *C07K 2317/76* (2013.01); *C07K 2317/34* (2013.01)
USPC .................. 424/153.1; 424/130.1; 424/133.1; 424/141.1; 424/143.1; 424/173.1; 530/387.1; 530/387.3; 530/388.2; 530/388.22; 530/388.7

(58) Field of Classification Search
None
See application file for complete search history.

(56) References Cited

U.S. PATENT DOCUMENTS

| | | | |
|---|---|---|---|
| 4,783,399 A | 11/1988 | Oldstone et al. | |
| 5,530,101 A | 6/1996 | Queen et al. | |
| 5,593,882 A | 1/1997 | Erbe et al. | |
| 5,800,815 A | 9/1998 | Chestnut et al. | |
| 5,859,205 A | 1/1999 | Adair et al. | |
| 6,033,667 A | 3/2000 | Chestnut et al. | |
| 6,210,670 B1 | 4/2001 | Berg | |
| 6,407,213 B1 | 6/2002 | Carter et al. | |
| 6,667,036 B2 | 12/2003 | Cummings et al. | |
| 7,223,845 B2 * | 5/2007 | Cummings et al. | 530/395 |
| 7,317,091 B2 | 1/2008 | Lazar et al. | |
| 7,563,441 B2 | 7/2009 | Graus et al. | |
| 7,754,867 B2 | 7/2010 | Graus et al. | |
| 8,377,440 B2 | 2/2013 | McEver et al. | |
| 2003/0198639 A1 | 10/2003 | Frenette et al. | |
| 2004/0072796 A1 * | 4/2004 | Embury et al. | 514/56 |
| 2005/0048133 A1 | 3/2005 | Pinsky et al. | |
| 2005/0112124 A1 | 5/2005 | Frenette et al. | |
| 2006/0024298 A1 | 2/2006 | Lazar et al. | |
| 2009/0285812 A1 | 11/2009 | Alvarez et al. | |
| 2010/0209423 A1 | 8/2010 | Grouse et al. | |
| 2011/0212096 A1 | 9/2011 | Rollins et al. | |
| 2011/0287017 A1 | 11/2011 | Rollins et al. | |
| 2011/0293617 A1 | 12/2011 | Rollins et al. | |

FOREIGN PATENT DOCUMENTS

| | | | |
|---|---|---|---|
| WO | WO 93/06863 | | 4/1993 |
| WO | WO 93/21956 | | 11/1993 |
| WO | WO 94/25067 | | 11/1994 |
| WO | WO 95/33484 | | 12/1995 |
| WO | WO 95/34324 | | 12/1995 |
| WO | WO 97/48485 | | 12/1997 |
| WO | WO 2005/100402 A1 | | 10/2005 |
| WO | WO 2008/069999 | * | 6/2008 |
| WO | PCT/US2011/66470 | | 4/2012 |

OTHER PUBLICATIONS

PCT/US07/024692, Written Opinion of the International Searching Authority, Oct. 7, 2008.
EP 07867601, Supplementary European Search Report, Aug. 3, 2010.
Geng et al., "Neutrophil in Recognition Requires a $Ca^{2+}$-induced Conformational Change in the Lectin Domain of GMP-140*", The Journal of Biological Chemistry, vol. 266, pp. 22313-22318 (1991).
Berg EL, Fromm C, Melrose J, Tsurushita N. Antibodies cross-reactive with E- and P-selectin block both E- and P-selectin functions. Blood, Jan. 1, 1995;85(1):31-7. PMID: 7528571.
Mehta P, Patel KD, Laue TM, Erickson HP, Mcever RP. Souluble monomeric P-selectin containing only the lectin and epidermal growth factor domains binds to P-selectin glycoprotein ligand-1 on leukocytes. Blood, Sep. 15, 1997; 90(6): 2381-9. PMID: 9310489.

(Continued)

*Primary Examiner* — Phillip Gambel
(74) *Attorney, Agent, or Firm* — Giordano & Chavous LLC

(57) ABSTRACT

Antibodies are disclosed which bind specifically to P-selectin and which block the binding of PSGL-1 to P-selectin. These anti-P-selectin antibodies may also cause dissociation of preformed P-selectin/PSGL-1 complexes. The disclosure identifies a heretofore unrecognized, near N-terminal, antibody binding domain (a conformational epitope) of P-selectin to which the function-blocking antibodies (which may be chimeric, human or humanized antibodies for example) bind. Antibodies are disclosed which bind to the conformational epitope of P-selectin and which have a dual function in blocking binding of PSGL-1 to P-selectin, and in causing dissociation of preformed P-selectin/PSGL-1 complexes. Such single and dual function anti-P-selectin antibodies and binding fragments thereof may be used in the treatment of a variety of inflammatory and thrombotic disorders and conditions. Screening methods for identifying such antibodies are also disclosed.

18 Claims, 11 Drawing Sheets

(56) References Cited

OTHER PUBLICATIONS

Ruchaud-Sparangano MH, Malaud E, Gayet O, Chignier E, Buckland R, McGregor JL. Mapping the epitope of a functional P-selectin monoclonal antibody (LYP20) to a short complement-like repeat (SCR 4) domain: use of human-mouse chimera and homologue-replacement mutagenesis. Biochem. J., 1998. 1;332(Pt2):309-14. PMID: 9601057.

Hirose M, Kawashima H, Miyasaka M. A functional epitope on P-selectin that supports binding of P-selectin to P-selectin glycoprotein ligand-1 but not to sialyl Lewis X oligosaccharides. Int. Immunol., May 1998;10(5): 639-49. PMID: 9645612.

Leppanen A, Mehta P, Ouyang YB, Ju T, Helin J, Moore KL, van Die I, Canfield WM, McEver RP, Cummings RD. 1999. A novel glycosulfopeptide binds to P-selectin and inhibits leukocyte adhesion to P-selectin. J Biol Chem Aug. 27;274(35):24838-48. PMID: 10455156.

Kaul et al. "Hypoxia/reoxygenation causes inflammatory response in transgenic sickle mice but not in normal mice", The Journal of Clinical Invenstigation, vol. 106, No. 3, pp. 411-420, (2000).

Matsui NM, Borsig L, Rosen SD, Yaghmai M, Varki A, Embury SH P-selectin mediates the adhesion of sickle erythrocytes to the endothelium. Blood, 2001. 98(6): p. 1955-62. PMID: 11535535.

Somers WS, Tang J, Shaw GD, Camphausen RT. Insights into the molecular basis of leukocyte tethering and rolling revealed by structures of P- and E-selectin bound to SLe(X) and PSGL-1. Cell, Oct. 27, 2000;103(3):467-79. Erratum in: Cell, Jun. 29, 2001;105(7):971. PMID: 11081633.

Turhan A, Weiss LA, Mohandas N, Collier BS, Freette PS. Primary role for adherent leukocytes in sickle cell vascular occlusion: a new paradigm. Proc Natl Acad Sci U S A, 2002. 99(5): p. 3047-51. PMID: 1180644.

Hebbel RP, Osarogiagbon R, and Kaul D. The endothelial biology of sickle cell disease: inflammation and a chronic vasculopathy. Microcirculation, 2004. 11(2): p. 129-51. Review. PMID: 15280088.

Chiang EY and Frenette PS. Sickle cell vaso-occlusion. Hematol Oncol Clin North Am, 2005. 19(5): p. 771-84, Review. PMID: 16214643.

Embury et al., "The contribution of endothelial cell P-selectin to the microvascular flow of mouse sickle erythrocytes in vivo", The American Society of Hematology, Blood, vol. 104, No. 10, pp. 3378-3385, (2004).

Okpala I, Leukocyte adhesion and the pathophysiology of sickle cell disease. Curr Opin Hematol, 2006. 13(1): p. 40-4. Review. PMID: 16319686.

Embury, SH. The not-so-simple process of sickle cell vasoocclusion. Microcirculation, 2004. 11(2): p. 101-13. PMID: 15280086.

Moore et al., "P-selectin glycoprotein ligand-1 mediates rolling of human neutrophils on P-selectin" J. Cell Biol. (Feb. 1995) vol. 128(4): pp. 661-671.

Beiboer et al., "Guided selection of a pan carcinoma specific antibody reveals similar binding characteristics yet structural divergence between the original murine antibody and its human equivalent." J. Mol. Boil. (2000) 296, pp. 833-849.

Brown et al., "Tolerance of single, but not multiple, amino acid replacements in antibody VH CDR 2: a means of minimizing B cell wastage from somatic hypermutation?" J. Immuno. (May 1996) 3285-3291.

Casset et al., "A peptide mimetic of an anti-CD4 monoclonal antibody by rational design." Biochemical and Biophysical Research Communications (2003) 307, pp. 198-205.

Klimka et al., "Human anti-CD30 recombinant antibodies by guided phage antibody selection using cell panning." British Journal of Cancer (2000) 83, pp. 252-260.

MacCallum et al., "Antibody-antigen Interactions: Contact Analysis and Binding Site Topography." J. Mol. Biol., (1996) 262, pp. 732-745.

Padlan, Anatomy of the antibody molecule. Mol. Immunol. (Feb. 1994) 31(3), pp. 169-217.

Paul, "Fundamental Immunology, Third Edition." (1993), pp. 292-295.

Rudikoff et al., "Single amino acid substitution altering antigen-binding specificity." Proc. Natl. Acad. Sci. USA (Mar. 1982 79(6) pp. 1979-1983.

Vajdos et al., "Comprehensive functional maps of the antigen-binding site of an anti-ErbB2 antibody obtained with shotgun scanning mutagenesis." J. Mol. Biol. (Jul. 5, 2002) 320(2), pp. 415-428.

EP 07867601.2, McEver et al., European Examination, dated Apr. 21, 2011.

EP 07867601.2, McEver et al., Response to European Examination of Apr. 21, 2011, filed Oct. 20, 2011.

* cited by examiner

Human/Mouse P-selectin

```
                A           Lectin Domain      B         C1                D
Human   1   WTYHYSTKAYSWNISRKYCQNRYTDLVAIQNKNEIDYLNKVLPYYSSYYWIGIRKNNKTW
Mouse   1   WTYNYSTKAYSWNNSRVFCRRHFTDLVAIQNKNEIAHLNDVIPFFNSYYWIGIRKINNKW
                D                    E1           C2            E2  C3
Human  61   TWVGTKKALTNEAENWADNEPNNKRNNEDCVEIYIKSPSAPGKWNDEHCLKKKHALCYTA
Mouse  61   TWVGTNKTLTEEAENWADNEPNNKKNNQDCVEIYIKSNSAPGKWNDEPCFKRKRALCYTA
                ▼        F    EGF Domain        ▼                  CR1
Human 121   SCQDMSCSKQGECLETIGNYTCSCYPGFYGPECEYVRECGELELPQHVLMNCSHPLGNFS
Mouse 121   SCQDMSCSNQGECIETIGSYTCSCYPGFYGPECEYVKECGKVNIPQHVLMNCSHPLGEFS
                                            ▼                  CR2
Human 181   FNSQCSFHCTDGYQVNGPSKLECLASGIWTNKPPQCLAAQCPPLKIPERGNMTCLHSAKA
Mouse 181   FNSQCTFSCAEGYELDGPGELQCLASGIWTNNPPKCDAVQCQSLEAPPHGTMACMHPIAA Human 241   FQHQSSCSFSCEEGFALVGPEVVQCTASGVWTAPAPVCK---
Mouse 241   FAYDSSCKFECQPGYRARGSNTLHCTGSGQWSEPLPTCEAIA
```

VH: Chimeric vs human sequence: 62.2%
Humanized vs human sequence: 82.9% (v1) and 79.3% (v2)

Fig. 8

METHODS OF TREATING INFLAMMATORY OR THROMBOTIC CONDITIONS WITH ANTI-P-SELECTIN ANTIBODIES

CROSS-REFERENCE TO RELATED APPLICATIONS

This application is a continuation-in-part of U.S. Ser. No. 12/516,987, filed May 29, 2009, which claims priority under 35 U.S.C. 371 from International Application No. PCT/US2007/024692, filed Nov. 30, 2007, which claims benefit of U.S. Provisional Application No. 60/872,170, filed Dec. 1, 2006. Each of the above applications is hereby expressly incorporated herein by reference in its entirety.

STATEMENT REGARDING FEDERALLY SPONSORED RESEARCH OR DEVELOPMENT

Not applicable.

SEQUENCE LISTING

The instant application contains a Sequence Listing which has been submitted in ASCII format via EFS-Web and is hereby incorporated by reference in its entirety. Said ASCII copy, created on Aug. 8, 2013, is named 2208049.00122US4_SL.txt and is 124,305 bytes in size.

BACKGROUND

The present invention relates to antibodies and antibody fragments which bind to specific conformational epitopes of P-selectin, and to methods of their use and identification.

In normal hemostasis and immune surveillance, leukocytes circulate freely in the blood and respond to injury and infection in a sequential process of adhesion signaling mediated by cell adhesion molecules (1-3). In inflammatory and thrombotic disease, this process is dysregulated and can sustain pathology wherein leukocytes attack the body's own tissue and can cause serious and sometimes deadly complications. It is well known that leukocyte adhesion plays a major role in the pathology of many inflammatory and thrombotic disorders such as vasoocclusion in sickle cell disease, reperfusion injury, thrombosis, atherosclerosis, asthma, rheumatoid arthritis, psoriasis and tumor metastasis (4-15) deep venous thrombosis (DVT). P-selectin is also involved in other disease processes, such as tissue and organ damage associated with inflammation, e.g., ischemia-reperfusion injury. P-selectin is thus a target for intervention in human inflammatory and thrombotic diseases.

Selectins are a family of adhesion proteins which are known to play key roles in the recruitment of leukocytes to activated endothelium and platelets. P-selectin is a member of the selectin family of adhesion glycoproteins which also includes L- and E-selectins (16). The selectins mediate the recruitment, initial tethering and rolling, and adherence of leukocytes to sites of inflammation (1). P-selectin is stored in Weibel-Palade bodies of endothelial cells and alpha-granules of platelets and is rapidly mobilized to the plasma membrane upon stimulation by vasoactive substances such as histamine and thrombin (17).

Sickle Cell Disease

Sickle cell disease (SCD) is a rare inherited blood disorder that causes chronic anemia and vasoocclusion, affecting primarily people of African-American heritage in the United States. Sickle cell disease is the most common single gene disorder in African Americans, affecting approximately 1 in 375-600 persons of African ancestry (18, 19). Sickle cell conditions are also common among people of Mediterranean countries, Africa the Caribbean and parts of South and Central America (18, 19).

SCD is an autosomal recessive disease caused by a single missense mutation (Val6Ala) in the β-globin gene that renders the mutant hemoglobin less soluble and prone to polymerization upon deoxygenation. The polymerization of hemoglobin causes deformation of the erythrocyte to give the cell a sickled shape (20).

SCD has three common variants: homozygous sickle cell disease (hemoglobin SS disease), doubly heterozygous sickle hemoglobin C disease (hemoglobin SC disease) and the sickle β-thalassemias. The most common and severe form of the disease occurs in individuals who inherit two copies of the HbS variant (HbSS) and the primary hemoglobin in their red blood cells is sickle hemoglobin. Other individuals can be affected as compound heterozygotes with varying severity of the disease. They have one copy of the HbS variant paired with a copy of another β-globin gene variant. HBSC results in a mild form of the disease. Hb β-thalassemia variants (resulting in the inability to produce the normal βA globin chain ($\beta^\circ$) or a reduction in its production ($\beta^+$) result in a range of clinical severities. HbS $\beta^\circ$ is a severe form, whereas HbS $\beta^+$ can be moderate or mild based on the contribution of each variant to the total hemoglobin of the patient. Other more rare variants can result if in conjunction with the S gene, another abnormal hemoglobin is inherited from the other parent, such as D, G or O. The predominant form of sickle cell is present in individuals with one copy of HbS and one copy of the normal β-globin gene (HbA). These individuals carry the sickle cell trait (18).

SCD affects an estimated 50-100,000 people in the US (21-24). All individuals that are homozygous or compound heterozygous for HbS show some clinical manifestations of SCD. Symptoms usually appear within the first 6 months of life but there is considerable variability in SCD severity (25). Individuals with HbSS are most severely affected, followed by individuals with HBbS $\beta^\circ$-thalassemia (22, 26). In addition to genotype, additional factors affect disease severity such as the levels of fetal hemoglobin and the haplotye of the β-globin cluster, a region that contains 5 genes that code for the β portion of hemoglobin. Despite the capacity to determine genetic risk factors, the ability to predict disease course from birth is limited (27).

In the USA, sickle cell screening at birth is mandated in all 50 states and the District of Columbia (28) and offers an opportunity for early intervention. Diagnostic testing methodology usually comprises a complete blood count in conjunction with one or more of hemoglobin electrophoresis, isoelectric focusing, high-performance liquid chromatography and DNA testing (22).

Chronic Anemia and Hemolysis

The sickled erythrocyte has a shorter half-life than the normal erythrocyte and results from the instability of HbS and the effects of repeated episodes of hemoglobin polymerization/depolymerization in the circulation. This affects membrane ionic permeability, cellular viscosity and deformability (20) and promotes oxidative membrane damage (29). Sickle cell disease patients are anemic by 2 to 3 months of age and develop symptoms and complications associated with chronic anemia and hemolysis (22, 30) such as renal disease, ophthalmic disorders, leg ulcers, priapism and pulmonary hypertension (26, 31-37). Hemoglobin values for SCD patients range from 6 to 10 g/dL and the hemoglobin S molecule has a poor affinity for oxygen. Triggers for transfusion in patients are a hemoglobin value of 5 or less or a precipitous drop in hemoglobin of 2 g/dL or more. Transfusions are typically given to restore hemoglobin values to baseline levels established for each patient as excessive hemotocrit can precipitate sickling (38). SCD patients are more susceptible to parvovirus B19 infection which can arrest erythropoiesis and lead to aplastic anemia crisis (39).

Vasoocclusive Pain Crisis

Vascular occlusion is central to the clinical course of SCD and likely involves both the micro and macro circulation. Occlusion occurring in the microvasculature can culminate in acute painful episodes or vasoocclusive pain crises. Vasoocclusive pain crisis is the clinical hallmark of microvascular occlusions and accounts for over 90% of hospital admissions of adults SCD patients. It is well known that polymerization of hemoglobin S during deoxygenation and cell sickling leads to blockage of the microvasculature (40). However, it has recently become clear that hemoglobin S polymerization is not solely responsible for vasoocclusion. It has now been demonstrated that such events as sickled red cell lysis, cell membrane damage and oxidative stress, repeated ischemic damage, and microvasculature injury due to the adhesive interactions between sickle red cells and the endothelium that culminate in a proinflammatory environment (41-43). In this environment of chronic vascular inflammation, the adherence of leukocytes, platelets and sickled red cells to activated blood vessel endothelium and to each other is believed to be a primary cause of microvasculature blockage and vasoocclusive pain crisis (43-47). Additional factors such as the rigidity of sickled cells, increased blood viscosity, and local vasoconstriction have also been identified as potentially contributing to the vasoocclusion process.

Long-term repeated vasoocclusive events and occlusions occurring in the macrovasculature can cause life-threatening complications leading to organ damage and failure, stroke and death (40). There is an approximately 20 to 30 year reduction in life expectancy in sickle cell disease patients (48). Chronic pain in SCD is not just a continuation of the pain of vasoocclusion: it is usually secondary to avascular necrosis of bone at various joints (49). Sickled red cells can become trapped in the spleen causing it to become enlarged and precipitating splenic sequestration crisis causing sudden and severe anemia. Functional asplenia leaves patients susceptible to infection (18). Bone growth retardation, renal (32), ophthalmic (33) and cerebrovascular complications (ranging from clinically evident acute stroke to transient silent ischemic infarct) (50) are seen as major clinical consequences of SCD and vasoocculsive injury (22). Acute chest syndrome is another major complication (51), and is a significant cause of morbidity and mortality (52).

Pain episodes appear to be triggered by a number of factors including cold, stress and physical exertion (38, 53). The frequency, severity, location and duration of pain crises can vary considerably, even within a specific disease subtype. Patients with homozygous sickle cell and sickle cell β°-thalassemia have a higher frequency of vasoocclusive pain crises than patients with hemoglobin SC and sickle cell-β°-thalassemia genotype (54). Disease severity is thought to depend on a complex interaction of genetic, rheologic and hematologic factors, as well as microvascular and endothelial factors. Crises commonly involve pain in the back, legs, knees, arms, chest and abdomen (53). The frequency of crisis and pain severity varies considerably among patients and in the same patient over time. One study evaluating pain rates in patients ranging from newborns to age 50 years indicated that 5.2 percent of patients with sickle cell disease have three to 10 episodes of severe pain every year (54). In an independent study, over 30% of sickle cell patients in the US (approximately 27,000 patients) have three or more pain crises per year (55). Moreover, a recent study (PISCES) evaluating health related quality of life issues in SCD patients indicated that pain crisis might be significantly underreported among SCD patients (56).

Current Therapies for Vascular Occlusion

Vascular occlusion in SCD patients can manifest in multiple ways including vasoocclusive pain crisis, acute chest syndrome, cerebrovascular events and multiple types of organ failure. Therefore, treatment modalities for vascular occlusion depend on the clinical course and severity of the disease and are generally symptomatic or palliative in nature. Patient education in the avoidance of initiating factors that precipitate vasoocclusive pain crisis has shown some prophylactic benefit. The two most common symptomatic treatments are blood transfusions and analgesics. Most SCD patients commonly have hemoglobin values between 6 and 10 g/dL and hemoglobin values typically drop at least 1 g per dL during a vasoocclusive pain crisis. Severe pain resulting from vasoocclusive crisis can be treated with narcotics but their use is controversial due to concerns of narcotic addiction and tolerance. Other complications with narcotic use are drug-seeking behavior, sedation and respiratory depression. Oxygen management has been utilized to treat vasoocclusive pain crisis despite the lack of strong evidence supporting its effectiveness. Rehydration is also sometime used during vasoocclusive pain crises with some benefit (22, 38).

Bone marrow transplantation may be considered and can be curative, but its use is restricted to a limited number of patients, and carries a high risk of morbidity and mortality (22).

Hydroxyurea (Droxia) is the only FDA approved drug for treatment of SCD pain crises. The mechanisms by which it produces its beneficial effects are uncertain but may involve increasing hemoglobin F levels in RBCs thereby decreasing the level of hemoglobin S polymerization. Hydroxyurea is cytotoxic, myelosuppressive and teratogenic (57, 58) which implies a carcinogenic risk to SCD patients. The long-term effects however, on hematologic toxicities, organ damage and carcinogenicity are currently unknown (59, 60).

In summary, most therapies for vasoocclusive pain crisis in SCD patients provide symptomatic relief and do not address the underlying cause of this debilitating condition. To date only one therapy has been approved by the FDA for the treatment of pain crisis, thus, patients with SCD represent a major unmet medical need in a life-threatening disease with severe morbidities.

P-Selectin as a Therapeutic Target for SCD

In SCD, as noted above, interactions between sickled red cells, platelets, leukocytes and the microvasculature are P-selectin-dependent processes and result in vasoocclusion and painful crisis. Studies in transgenic mice engineered to express human β hemoglobin S ($\beta^S$) have shown that antibody-mediated inhibition of P-selectin function can prevent and/or reduce vasoocclusion, indicating a therapeutic potential for this target. In addition mice expressing the $\beta^S$ hemoglobin that lack P-selectin (due to gene deletion) do not suffer vasoocclusion, further supporting a key role for this molecule in this morbidity.

The hyper-inflammatory state in SCD patients is characterized by activated monocytes and vascular endothelium (61-63). A similar proinflammatory phenotype was demonstrated in resting state $\beta^S$ mice which exhibit elevated levels of peripheral leukocytes and neutrophils, an increased number of rolling and adherent leukocytes, and reduced blood flow volume and red blood cell velocities (64). The $\beta^S$ mice were hypersensitive to hypoxia/reoxygenation resulting in an inflammatory response represented by a significant increase in the number of adherent and emigrated leukocytes. This inflammatory response was completely blocked by a functionally blocking anti-mouse P-selectin antibody, but not by a functionally blocking anti-mouse E-selectin antibody, demonstrating a critical role for P-selectin in this process.

Inflammatory Bowel Disease

Inflammatory Bowel Disease ("IBD") is the collective term used to describe two chronic, idiopathic inflammatory diseases of the gastrointestinal tract: ulcerative colitis ("UC") and Crohn's Disease ("CD"). UC and CD are considered together because of their overlapping clinical, etiologic, and pathogenetic features. From a therapeutic and prognostic standpoint, however, it is useful to distinguish them.

IBD occurs world-wide and is reported to afflict as many as two million people. Onset has been documented at all ages; however, IBD predominately begins in young adulthood. The three most common presenting symptoms of IBD are diarrhea, abdominal pain, and fever. The diarrhea may range from mild to severe and is often accompanied by urgency and frequency. In UC, the diarrhea is usually bloody and may contain mucus and purulent matter as well. Anemia and weight loss are additional common signs of IBD. Reports of an increasing occurrence of psychological problems, including anxiety and depression, are perhaps not surprising secondary effects of what is often a debilitating disease that occurs in people in the prime of life.

A battery of laboratory, radiological, and endoscopic evaluations are combined to derive a diagnosis of IBD and to assess the extent and severity of the disease. Nevertheless, differentiating UC from CD, as well as other types of inflammatory conditions of the intestines, such as irritable bowel syndrome, infectious diarrhea, rectal bleeding, radiation colitis, and the like, is difficult, because the mucosa of the small and large intestines reacts in a similar way to a large number of different insults. Once other types of bowel disorders have been ruled out, the final diagnosis is often made on the basis of the progression of the disease. In many patients, though, the colitis must still be regarded as indeterminate because of the overlapping features of UC and CD, particularly with CD of the colon.

The leading early symptoms of UC and CD are chronic recurrent diarrhea, bloody diarrhea, recurrent abdominal pain, nausea, weight loss general evidence of inflammation without any obvious explanation (fever, raised ESR, leucocytosis, thrombocytosis and dysproteinenemia or anemia). Among these symptoms, diarrhea and anemia are more characteristic of UC while pain and weight loss and marked evidence of inflammation are more common in CD. While the history and physical examination of a patient can help, the final confirmation of the diagnosis has traditionally been made endoscopically, histologically and, in relation to the small intestine, radiologically as well.

The SAMP-1/Yit mouse model of spontaneous iletis closely resembles human Crohn's Disease (65, 66). Therapeutic inhibition of PSGL-1 binding uniquely ameliorates ileitis in this model whereas blockade of individual selectins does not (67). Inhibition of TNF in this model does reduce the severity of ileitis in a manner similar to anti-PSGL-1 binding although the therapeutic effect does not appear to be as potent as anti-PSGL-1. Thus, the SAMP-1 model appears to closely mirror human Crohn's Disease not only in its pathophysiology but also in its response to therapeutic intervention. This evidence points to the conclusion that therapeutic substances which inhibit P-selectin-PSGL-1 binding activity in humans (and other primates) would also be effective as treatments of Crohn's Disease.

P-selectin plays its central role in the recruitment of leukocytes to inflammatory and thrombotic sites by binding to its counter-receptor, P-selectin glycoprotein ligand-1 (PSGL-1) (or a PSGL-1-like receptor on sickled red blood cells), which is a mucin-like glycoprotein constitutively expressed on leukocytes including neutrophils, monocytes, platelets, and on some endothelial cells (68). The ultimate physiologic function of the selectins is to promote extravasation of leukocytes into inflamed or damaged tissues. The initial binding of P-selectin on the endothelium to PSGL-1 on the leukocytes is essential and central to this process. The predominant mechanism for rolling and tethering of leukocytes to activated endothelium and platelets is the binding of leukocyte PSGL-1 to the P-selectin on these cells (68, 69). PSGL-1 binds to P-, L- and E-selectin (70). P-selectin and SGP-3, a glycosulfopeptide modeled from the N-terminus of PSGL-1, have been co-crystallized and the contact residues for lectin-ligand binding have been identified (71).

The selectins share common structural motifs including a lectin domain (or carbohydrate recognition domain), an epidermal growth factor-like domain (EGF), a varying series of consensus repeats, a transmembrane domain and a cytoplasmic tail (70). As noted, the initial tethering and rolling of leukocytes is mediated by the interaction of P-selectin and PSGL-1. Thus the blocking of P-selectin function by using (1) antibodies to P-selectin, (2) antibodies to PSGL-1, (3) fragments of PSGL-1 or recombinant forms of PSGL-1, (4) small molecules that mimic the binding domain of PSGL-1, and (5) other molecules that disrupt the binding of P-selectin to PSGL-1, can block leukocyte rolling and tethering and thus prevent firm adhesion to endothelial cells or platelets. Mice deficient in P-selectin or PSGL-1 also fail to support leukocyte tethering and rolling on activated endothelial cells (72, 74). L-selectin plays a dual role in that it is constitutively expressed on circulating leukocytes and can initiate "secondary binding" by interaction with PSGL-1 on other leukocytes (75). This process leads to further recruitment of new leukocytes to the inflamed area. L-selectin binding to PSGL-1 also plays a role in homing of lymphocytes to the high endothelial vasculature (HEV) venules in the secondary lymphatic system (76). E-selectin is transcriptionally regulated and is expressed on activated endothelial cells hours after P-selectin mediated events. E-selectin can bind PSGL-1 with low affinity but can also bind other ligands. Single transgenic knockout mice for each selectin have shown that these molecules possess compensatory selectin mechanisms for leukocyte homing and rolling (77).

In view of the above, there is a well-established need for new treatments, such as antibodies, that target P-selectin as a means of treating inflammatory and thrombotic diseases by disrupting the binding of P-selectin and PSGL-1. It is therefore a preferred goal of the present invention to block P-selectin binding to PSGL-1 to block the adherence of blood cells that contribute to vasoocclusion in SCD and other thrombotic disorders.

SUMMARY OF THE DISCLOSURE

The presently disclosed and claimed inventive concepts, in one embodiment, are directed to "function-blocking" antibodies which bind specifically to P-selectin and which block the binding of PSGL-1 to P-selectin. These anti-P-selectin antibodies may also cause dissociation of preformed P-selectin/PSGL-1 complexes. The present disclosure describes a heretofore unrecognized antibody binding domain (a conformational epitope) within the lectin domain (e.g., carbohydrate recognition domain, CRD) of P-selectin to which the function-blocking antibodies (which may be chimeric, human or humanized antibodies or fragments thereof for example) bind. The presently disclosed and claimed inventive concepts, in one embodiment, are also directed to anti-P-selectin antibodies which bind to the conformational epitope described herein and which have a dual function in (1) blocking binding of PSGL-1 to P-selectin, and (2) causing dissociation of preformed P-selectin/PSGL-1 complexes. The presently disclosed and claimed inventive concepts in particular are directed to using such single and dual function anti-P-selectin antibodies or antibody fragments as described herein in treatments for inflammatory, thrombotic or other conditions or disorders in primates (including humans) which involve platelet, sickled red cell, leukocyte, lymphocyte, and/or endothelial cell adhesion, wherein the condition or disorder comprises or is associated with (but not limited to) at least one of sickle cell vasoocclusive pain crisis, inflammatory bowel disease (e.g., Crohn's Disease, ulcerative colitis, enteritis), arthritis (e.g., rheumatoid arthritis, osteoarthritis, psoriatic arthritis), graft rejection, graft versus host disease, asthma, chronic obstructive pulmonary disease, psoriasis, dermatitis, sepsis, nephritis, lupus erythematosis, scleroderma, rhinitis, anaphylaxis, diabetes, multiple sclerosis, atherosclerosis, thrombosis, tumor metastasis, allergic reactions, thyroiditis, ischemic reperfusion injury (e.g., due to myocardial infarction, stroke, or organ transplantation), and conditions associated with extensive trauma, or chronic inflammation, such as for example, type IV delayed hypersensitivity, associated for example with infection by Tubercle bacilli, or systematic inflammatory response syndrome, or multiple organ failure. Other embodiments of the inventive concepts disclosed and claimed herein will be apparent in the Detailed Description below.

BRIEF DESCRIPTION OF THE DRAWINGS

FIG. 1 shows a homology comparison at the amino acid level of human P-selectin (SEQ ID NO:1) and mouse P-selectin (SEQ ID NO:2) indicating the location of lectin, EGF, CR1 and CR2 domains (transition between domains is indicated by ↓). Nonlinear conformational domains. A, B, C1, D, E1, C2, E2, C3, and F are indicated by dashed boxes. Amino acid differences are indicated in boldface.

FIG. 7 is a schematic showing proposed humanized variable light chain sequences prepared using sequences from murine mAb G1. G1-VK shows the original murine variable light chain sequence. AAZ0906 shows the acceptor human variable light chain sequence. Hu-01_VK_v1 and Hu-01_VK_v2 show two alternative versions of the humanized antibody variable light chain sequence, in which light chain CDR regions 1-3 of the human sequence are replaced with those of the murine light chain CDR regions 1-3.

FIG. 8 is a schematic showing proposed humanized variable heavy chain sequences prepared using sequences from murine mAb G1. G1-VH shows the original murine variable heavy chain sequence. AAC18323 shows the acceptor human variable heavy chain sequence. Hu-G1_VH_v1 and Hu-G1_VH_v2 show two alternative versions of the humanized antibody variable heavy chain sequence, in which heavy chain CDR regions 1-3 of the human sequence are replaced with those of the murine heavy chain CDR regions 1-3.

DETAILED DESCRIPTION

Figure 2:
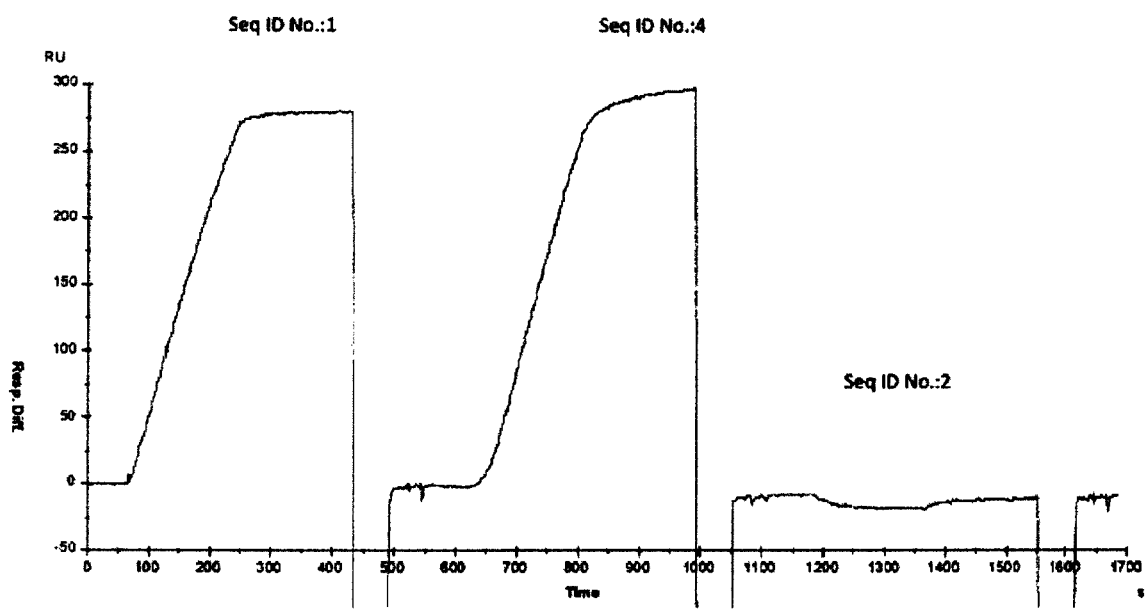
FIG. 2 shows a representative sensogram showing the ability of the G1 test antibody to bind various P-selectin chimeras: SEQ ID NO:1 (human P-selectin), SEQ ID NO:2 (mouse P-selectin), and SEQ ID NO:4 (human cluster A (aa 1-35) replaces mouse aa 1-35 in mouse P-selectin). The G1 antibody binds to human P-selectin (SEQ ID NO:1), does not bind to mouse P-selectin (SEQ ID NO:2), and binds mouse P-selectin when human amino acids from Cluster A have been inserted into the mouse sequence in residues 3-23 (SEQ ID NO:4).

As indicated above, the presently disclosed and claimed inventive concepts, in one embodiment, are directed to antibodies which bind specifically to P-selectin and which block the binding of PSGL-1 to P-selectin (and are referred to herein as "function-blocking" antibodies). In some embodiments, these anti-P-selectin antibodies may also cause dissociation of preformed P-selectin/PSGL-1 complexes. The disclosure describes a heretofore unrecognized antibody binding domain (a conformational epitope) within the lectin domain (e.g., carbohydrate recognition domain, CRD) of P-selectin to which the function-blocking antibodies (which may be chimeric, human or humanized antibodies, or fragments thereof for example) bind. The presently disclosed and claimed inventive concepts also directed to anti-P-selectin antibodies which bind to the conformational epitope described herein and which have a dual function in (1) blocking binding of PSGL-1 to P-selectin and (2) causing dissociation of preformed P-selectin/PSGL-1 complexes. The presently disclosed and claimed inventive concepts in particular are directed to using such single and dual function anti-P-selectin antibodies or antibody fragments as described herein in treatments for inflammatory, thrombotic or other conditions or disorders in primates (including humans) which involve platelet, sickled red cell, leukocyte, lymphocyte, and/or endothelial cell adhesion, wherein the condition or disorder comprises or is associated with (but not limited to) at least one of sickle cell vasoocclusive pain crisis, inflammatory bowel disease (e.g., Crohn's Disease, ulcerative colitis, enteritis), arthritis (e.g., rheumatoid arthritis, osteoarthritis, psoriatic arthritis), graft rejection, graft versus host disease, asthma, chronic obstructive pulmonary disease, psoriasis, dermatitis, sepsis, nephritis, lupus erythematosis, scleroderma, rhinitis, anaphylaxis, diabetes, multiple sclerosis, atherosclerosis, thrombosis, tumor metastasis, allergic reactions, thyroiditis, ischemic reperfusion injury (e.g., due to myocardial infarction, stroke, or organ transplantation), and conditions associated with extensive trauma, or chronic inflammation, such as for example, type IV delayed hypersensitivity, associated for example with infection by Tubercle bacilli, or systematic inflammatory response syndrome, or multiple organ failure. The presently disclosed and claimed inventive concepts are also directed to a screening assay for the detection of anti-P-selectin antibodies which bind to the conformational epitope of P-selectin described here, and, in one embodiment, also block binding of PSGL-1 to P-selectin, and which, in another embodiment, cause reversal of the binding of PSGL-1 to P-selectin (i.e., dissociation of the preformed complex).

It is noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the presently disclosed and claimed inventive concepts, the preferred methods and materials are now described.

"Leukocyte rolling," as used herein, includes weak adhesion of leukocytes to endothelial cells of blood vessels and rolling of leukocytes along endothelial cells of blood vessels prior to firm adhesion and transmigration of leukocytes into endothelial tissue. Following leukocyte rolling, these adherent leukocytes can migrate through the endothelium and destroy ischemic tissue during reperfusion. Accordingly, reduction of leukocyte rolling results in a reduction of damage to tissues and organs caused by acute inflammatory responses.

As used herein, a "P-selectin antagonist" includes any agent which is capable of antagonizing P-selectin, e.g., by inhibiting interaction between P-selectin and a P-selectin glycoprotein ligand-1, e.g., by inhibiting interactions of P-selectin expressing endothelial cells and activated platelets with PSGL-1 expressing leukocytes.

As noted herein, the presently disclosed and claimed inventive concepts are directed to purified antibodies (including but not limited to chimeric, human, or humanized antibodies and fragments thereof), which recognize (i.e., bind to) P-selectin (SEQ ID NO:1) and which block binding of P-selectin to PSGL-1 (or PSGL-1-like receptors), and to methods for screening for such antibodies and binding fragments thereof, and to therapeutic methods of use thereof.

More particularly, the presently disclosed and claimed inventive concepts are directed to purified antibodies (or fragments thereof), against P-selectin, host cells that produce such anti-P-selectin antibodies (or fragments thereof), screening assays to identify anti-P-selectin antibodies (or fragments thereof) which block leukocytes, sickled erythrocytes, lymphocyte, platelet and endothelial cell P-selectin-mediated adhesion and optionally further cause dissociation of preformed adhesions or cell complexes that were mediated through PSGL-1/P-selectin interactions, and therapeutic methods using such antibodies (or binding fragments thereof). The presently disclosed and claimed inventive concepts include novel antibodies against primate (including human) P-selectin and binding fragments thereof, particularly including, in one embodiment, hSel001 antibody. Preferred antibodies of the disclosure are capable of specifically binding primate (particularly human) P-selectin, and inhibiting one or more P-selectin activities in vitro and/or in vivo. Where used herein, the term "PSGL-1" is also intended to include "PSGL-1-like receptor" on sickled red cells (erythrocytes).

Antibodies

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain.

Depending on the amino acid sequences of the constant domain of their heavy chains, immunoglobulins can be assigned to different classes. There are at least five major classes of immunoglobulins: IgA, IgD, IgE, IgG and IgM, and several of these may be further divided into subclasses (isotypes), e.g. $IgG_1$, $IgG_2$, $IgG_3$ and $IgG_4$ and $IgA_1$ and $IgA_2$. The constant domains of the heavy chains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments per chain called complementarity determining regions (CDRs), also known as hypervariable regions, both in the light chain and the heavy chain variable domains.

The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each light and heavy chain are held together in close proximity by the FR regions and contribute to the formation of the antigen-binding site of the antibody. The constant domains are not involved directly in binding an antibody to an antigen, but exhibit various effector functions, such as participation of the antibody in antibody-dependent cellular toxicity.

An antibody of the presently disclosed and claimed inventive concepts thus can be in any of a variety of forms, including a whole immunoglobulin, an antibody fragment such as Fv, Fab, and similar fragments, a single chain antibody which includes the variable domain complementarity determining regions (CDRs), and the like forms, all of which fall under the broad term "antibody", as used herein. In preferred embodiments, in the context of both the therapeutic and screening methods described below, an antibody or fragment thereof is used that is immuno-specific for an antigen or epitope of the presently disclosed and claimed inventive concepts as described herein.

The term "antibody fragment" as used herein refers to a portion of a full-length antibody, generally the antigen binding or variable region. Examples of antibody fragments include Fab, Fab', $F(ab')_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an $F(ab')_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and $F(ab')_2$ fragments.

Antibody fragments may be as small as about 4, 5, 6, 7, 8, 9, 10, 11, 12, 13, 14, 15, 16, 17, 18, 19, 20, 21, 22, 23, 24, 25, 26, 27, 28, 29, or 30, 35, 40, 45 or 50 or 75 or 100 (inclusive) or more amino acids, for example. In general, an antibody fragment of the presently disclosed and claimed inventive concepts can have any upper size limit so long as it is has similar or immunological properties relative to antibody that binds with specificity to the P-selectin-binding described herein and which blocks binding of PSGL-1 to P-selectin. Where used herein the term "inclusive" is intended to refer to all integers between any two numbers listed herein.

As noted elsewhere herein, antibody fragments contemplated herein retain the ability to selectively bind to all of or a portion of the P-selectin binding epitope described herein. Preferably, an antibody or binding fragment of an antibody of the present invention is capable of binding to an epitope comprising one or more of amino acid residues 1-35, or, more particularly, 4-23, of the sequence set forth in SEQ ID NO:1. Some types of antibody fragments are defined as follows:

Fab is the fragment that contains a monovalent antigen-binding fragment of an antibody molecule. A Fab fragment can be produced by digestion of whole antibody with the enzyme papain to yield an intact light chain and a portion of one heavy chain.

Fab' is the fragment of an antibody molecule can be obtained by treating whole antibody with pepsin, followed by reduction, to yield an intact light chain and a portion of the heavy chain. Two Fab' fragments are obtained per antibody molecule.

Fab' fragments differ from Fab fragments by the addition of a few residues at the carboxyl terminus of the heavy chain CH1 domain including one or more cysteines from the antibody hinge region.

$(Fab')_2$ is the fragment of an antibody that can be obtained by treating whole antibody with the enzyme pepsin without subsequent reduction. $F(ab')_2$ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association (VH-VL dimer). It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

A single chain antibody (SCA) is defined herein as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" or "scFv" antibody fragments. Generally, the Fv polypeptide further comprises a polypeptide linker between the VH and VL domains that enables the sFv to form the desired structure for antigen binding.

As noted above, the antibodies or antibody fragments of the presently disclosed and claimed inventive concepts in preferred embodiments comprise immunoglobulins of the isotypes $IgG_1$, $IgG_2$, $IgG_3$, $IgG_4$ or $IgG_2/G_4$ chimeras, preferably binds to P-selectin with a high affinity (for example wherein the $K_d$ is ≤1000 nM) and preferably comprises a human constant region, and preferably inhibits binding of P-selectin to PSGL-1 and more preferably also caused reversal of binding of P-selectin to PSGL-1 in a preformed complex. Further, the anti-P-selectin antibody or binding fragment thereof preferably does not activate complement via the classical pathway by interacting with C1q and preferably does not bind Fc receptors, collectively called antibody effector function. The presently disclosed and claimed inventive concepts in particular are directed to using such single and dual function anti-P-selectin antibodies or antibody fragments as described and identified herein in treatments for inflammatory, thrombotic or other conditions or disorders in primates (including humans) which involve platelet, sickled red cell, leukocyte, lymphocyte, and/or endothelial cell adhesion, wherein the condition or disorder comprises or is associated with (but not limited to) at least one of sickle cell vasoocclusive pain crisis, inflammatory bowel disease (e.g., Crohn's Disease, ulcerative colitis, enteritis), arthritis (e.g., rheumatoid arthritis, osteoarthritis, psoriatic arthritis), graft rejection, graft versus host disease, asthma, chronic obstructive pulmonary disease, psoriasis, dermatitis, sepsis, nephritis, lupus erythematosis, scleroderma, rhinitis, anaphylaxis, diabetes, multiple sclerosis, atherosclerosis, thrombosis, tumor metastasis, allergic reactions, thyroiditis, ischemic reperfusion injury (e.g., due to myocardial infarction, stroke, or organ transplantation), and conditions associated with extensive trauma, or chronic inflammation, such as for example, type IV delayed hypersensitivity, associated for example with infection by Tubercle bacilli, or systematic inflammatory response syndrome, or multiple organ failure.

As noted elsewhere herein, P-selectin plays a central role in recruitment of leukocytes and lymphocytes to inflammatory and thrombotic sites by binding to a surface ligand (PSGL-1) on these cells and in the binding of sickled red cells to endothelia having activated endothelial cells. PSGL-1 is constitutively expressed on leukocytes, including neutrophils and monocytes, and on some endothelial cells. A PSGL-1-like receptor is expressed on sickled red cells and enables these cells to bind P-selectin on activated endothelial cells.

Without wanting to be bound by theory, it is believed that the treatment of vasoocclusive sickle cell pain crisis, for example by the anti-P-selectin antibody of the present invention, is effective by inhibiting any one or more of the following interactions: (1) PSGL-1 on leukocytes binding to P-selectin on activated endothelium; (2) a PSGL-1-like ligand on sickled red cells binding to P-selectin on activated endothelium; (3) P-selectin on the surface of activated platelets binding PSGL-1 on endothelial cells; (4) sickled red cells binding leukocytes through an uncharacterized ligand-receptor interaction; (5) P-selectin on activated platelets binding the PSGL-1 like receptor on sickled red cells, and/or; (6) P-selectin on the surface of activated platelets binding PSGL-1 on leukocytes. It is expected that the function-blocking anti-P-selectin antibody blocks the initiation and propagation of vasoocclusion at multiple levels of cell-cell interactions in the microvasculature.

The presently disclosed and claimed inventive concepts in one embodiment are directed to antibodies that specifically bind to human P-selectin. CDRs in such antibodies are not limited to the specific sequences of VH and VL shown herein or in the documents incorporated by reference herein and may include variants of these sequences that retain the ability to block P-selectin binding to PSGL-1. Such variants may be produced by a skilled artisan using techniques well known in the art. For example, amino acid substitutions, deletions, or additions, can be made in the FRs and/or in the CDRs as described elsewhere herein. While changes in the FRs are usually designed to improve stability and decrease immunogenicity of the antibody, changes in the CDRs are typically designed to increase affinity of the antibody for its target. Variants of FRs also include naturally occurring immunoglobulin allotypes. Such affinity-increasing changes may be determined empirically by routine techniques that involve altering the CDR and testing the affinity antibody for its target.

For example, conservative amino acid substitutions can be made within any one of the disclosed CDRs. Various alterations can be made according to methods well known to those skilled in the art (78). These include but are not limited to nucleotide sequences that are altered by the substitution of different codons that encode an identical or a functionally equivalent amino acid residue ("conservative substitutions") within the sequence, thus producing a "silent" change. For example, the nonpolar amino acids which may be conservatively substituted include alanine, leucine, isoleucine, valine, proline, phenylalanine, tryptophan, and methionine. The polar neutral amino acids which may be substituted conservatively include glycine, serine, threonine, cysteine, tyrosine, asparagine, and glutamine. The positively charged (basic) amino acids which may be conservatively substituted include arginine, lysine, and histidine. The negatively charged (acidic) amino acids which may be conservatively substituted include aspartic acid and glutamic acid. Substitutes for an amino acid within the sequence may also be selected from other members of the class to which the amino acid belongs.

Derivatives and analogs of antibodies of the invention can be produced by various techniques well known in the art, including recombinant and synthetic methods (79, 80). Antibodies in which CDR sequences differ only insubstantially from those of the variable regions of anti-P-selectin antibodies such as hSel001, discussed in further detail below, are also encompassed within the scope of this invention. As noted above, typically, an amino acid is substituted by a related amino acid having similar charge, hydrophobic, or stereochemical characteristics. Such substitutions would be within the ordinary skills of an artisan. Further, a skilled artisan would appreciate that changes can be made in FRs without adversely affecting the binding properties of an antibody. Changes to FRs include, but are not limited to, humanizing a non-human derived or engineering certain framework residues that are important for antigen contact or for stabilizing the binding site, e.g., changing the class or subclass of the constant region, changing specific amino acid residues which might alter the effector function such as Fc receptor binding.

As used herein, the "affinity" of the antibody for P-selectin or the conformational epitope thereof is characterized by its $K_d$, or disassociation constant. A stronger affinity is represented by a lower $K_d$ while a weaker affinity is represented by a higher $K_d$. As such, an antibody of the present invention preferably has an affinity for a P-selectin conformational epitope represented by a $K_d \leq 1000$ nM, or $\leq 500$ nM, or $\leq 100$ nM, or $\leq 50$ nM, or more preferably by a $K_d \leq 25$ nM, and still more preferably by a $K_d \leq 10$ nM, and even more preferably by a $K_d \leq 5$ nM, $\leq 1$ nM, or $\leq 0.1$ nM.

An antibody or antibody fragment "homolog," as used herein, means that a relevant amino acid sequence (preferably for example in the CDRs and/or variable domains VH and/or VL) of a protein or a peptide is at least 50%, 60%, 70%, 75%, 80%, 85%, 90%, 95%, 96%, 97%, 98%, 99%, 99.5%, or 100% identical to a given sequence. By way of example, such sequences may be variants derived from various species, or the homologous sequence may be recombinantly produced. The sequence may be derived from the given sequence by truncation, deletion, amino acid substitution, or addition. Percent identity between two amino acid sequences is determined by standard alignment algorithms such as, for example, Basic Local Alignment Tool (BLAST) and other alignment algorithms and methods of the art (81-84).

The term "isolated" or "purified" refers to a molecule that is substantially free of its natural environment. For instance, an isolated protein is substantially free of cellular material or other proteins from the cell or tissue source from which it was derived. The term also refers to preparations where the isolated protein is at least 70-80% (w/w) pure; or at least 80-90% (w/w) pure; or at least 90-95% pure; or at least 80%, 85%, 90%, 95%, 96%, 97%, 98%, 99%, or 100% (w/w) pure. In some embodiments, the isolated molecule is sufficiently pure for pharmaceutical compositions.

Inhibitory activity refers to a reduction in an activity of P-selectin by a P-selectin inhibitor (such as an antibody or fragment thereof), relative to the activity of P-selectin in the absence of the same inhibitor. A neutralizing antibody may reduce one or more P-selectin activities. For example, the reduction in activity (e.g., P-selectin binding to PSGL-1) is preferably at least about 10%, 20%, 30%, 40%, 50%, 60%, 70%, 75%, 80%, 85%, 90%, 95%, or higher. In another example, the dissociative activity of a dual function antibody or fragment (i.e., the percentage of preformed P-selectin/PSGL-1 complex which may be caused to dissociate) may be 10%, 20%, 30%, 40%, 50%, 60%, 70%, 75%, 80%, 85%, 90%, 95%, or higher.

The term "P-selectin inhibitor" when used herein includes any agent, such as, e.g., a neutralizing antibody, capable of inhibiting activity, expression, processing, binding, or cell surface localization of P-selectin. Such inhibitors are said to "inhibit," "neutralize," or "reduce" the biological activity of P-selectin.

The preparation of monoclonal antibodies is conventional and well known to persons of ordinary skill in the art. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography.

Methods of in vitro and in vivo manipulation of monoclonal antibodies are well known to those skilled in the art. For example, the monoclonal antibodies to be used in accordance with the present invention may be made by the hybridoma method first described by Kohler and Milstein (85), or may be made by recombinant methods, e.g., as described in U.S. Pat. No. 4,816,567, for example.

Another method involves humanizing a monoclonal antibody by recombinant means to generate antibodies containing, for example, human or primate specific and recognizable sequences.

Methods of making antibodies of the presently disclosed and claimed inventive concepts which bind with high affinity to human P-selectin or to the conformational epitopes thereof as described herein may comprise transfecting a cell with a DNA construct, the construct comprising a DNA sequence encoding at least a portion of the neutralizing P-selectin specific antibodies of the invention, culturing the cell under conditions such that the antibody protein is expressed by the cell, and isolating the antibody protein.

Preferably, the constant region has been modified to modulate (i.e. reduce or enhance) effector function as noted elsewhere as compared to the effector function of a wild-type immunoglobulin heavy chain Fc region. In various embodiments, the IgG constant region has reduced effector function, or alternatively it has increased effector function, for example. Fc effector function includes, for example, antibody-dependent cellular cytotoxicity (ADCC), phagocytosis, complement-dependent cytotoxicity, and half-life or clearance rate function. The IgG amino acid sequence of the Fc domain can be altered to affect binding to Fc gamma receptors (and thus ADCC or phagocytosis functions), or to alter interaction with the complement system (complement-dependent cytotoxicity function).

In one embodiment, the antibody comprises a constant region or Fc portion that has low or no affinity for at least one Fc receptor. In an alternative embodiment, the second polypeptide has low or no affinity for complement protein C1q. In general, an effector function of an antibody can be altered by altering the affinity of the antibody for an effector molecule such as an Fc receptor. Binding affinity will generally be varied by modifying the effector molecule binding site. Disclosure of IgG modifications that alter interaction with effector molecules such as Fc receptors can be found for example in U.S. Pat. Nos. 5,624,821 and 5,648,260.

Antibody proteins of the presently disclosed and claimed inventive concepts can be produced using techniques well known in the art. For example, the antibody proteins can be produced recombinantly in cells (79, 86).

For recombinant production, a polynucleotide sequence encoding the antibody protein is inserted into an appropriate expression vehicle, such as a vector which contains the necessary elements for the transcription and translation of the inserted coding sequence. The expression vehicle is then transfected into a suitable target cell which will express the peptide. Transfection techniques known in the art include, but are not limited to, calcium phosphate precipitation (87) and electroporation (88). A variety of host-expression vector systems may be utilized to express the antibody proteins described herein preferably including eukaryotic cells.

The presently disclosed and claimed inventive concepts further provide isolated nucleic acids encoding the antibodies disclosed or otherwise enabled herein. The nucleic acids may comprise DNA or RNA and may be wholly or partially synthetic or recombinant. Reference to a nucleotide sequence as set out herein encompasses a DNA molecule with the specified sequence, and encompasses a RNA molecule with the specified sequence in which U is substituted for T, unless context requires otherwise.

In another embodiment, the nucleic acid molecules which encode the antibodies of the presently disclosed and claimed inventive concepts also comprise nucleotide sequences that are, for example, at least 50% identical to the sequences disclosed herein. Also contemplated are embodiments in which a sequence is at least 85%, 90%, 95%, 96%, 97%, 98%, 99%, or 99.5% identical to a sequence disclosed herein and/or which hybridize to a sequence of the presently disclosed and claimed inventive concepts under conditions of high or moderate stringency. The percent identity may be determined by visual inspection and mathematical calculation.

Stringency, including "high stringency," as used herein, includes conditions readily determined by the skilled artisan based on, for example, the length of the DNA. Generally, such conditions are defined as hybridization conditions of 50% formamide, 6×SSC at 42° C. (or other similar hybridization solution, such as, e.g., Stark's solution, in 50% formamide at 42° C.), and with washing at approximately 68° C., 0.2×SSC, 0.1% SDS. The skilled artisan will recognize that the temperature and wash solution salt concentration can be adjusted as necessary according to factors such as the length of the probe.

"Moderate stringency," as used herein, includes conditions that can be readily determined by those having ordinary skill in the art based on, for example, the length of the DNA. The basic conditions are set forth by Sambrook et al. (79) and include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, generally being directed against a single epitopic site. Furthermore, in contrast to conventional polyclonal antibody preparations that typically include different antibodies directed against different determinants (epitopes), each monoclonal antibody is directed against a single determinant. In addition to their specificity, the monoclonal antibodies are advantageous in that, in one embodiment, they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567).

Methods of making antibody fragments are also known in the art (89) (incorporated herein by reference). Antibody fragments of the present invention can be prepared by proteolytic hydrolysis of the antibody or by expression in E. coli of DNA encoding the fragment. Antibody fragments, as noted above, can be obtained by pepsin or papain digestion of whole antibodies conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. No. 4,036,945 and U.S. Pat. No. 4,331,647, and references contained therein, which are hereby expressly incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the conformational epitope that is recognized by the intact antibody. For example, Fv fragments comprise an association of VH and VL chains. This association may be noncovalent or the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Another form of an antibody fragment is a peptide coding for a single CDR. CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells.

The presently disclosed and claimed inventive concepts comprise engineered antibodies including fully human and humanized forms of non-human (e.g., primate or murine) antibodies. Such humanized antibodies are chimeric immunoglobulins, immunoglobulin chains or fragments thereof (such as Fv, Fab, Fab', F(ab')$_2$ or other antigen-binding subsequences of antibodies) that contain minimal sequences derived from non-human immunoglobulin. For the most part, humanized antibodies are human immunoglobulins in which residues from a CDR of the recipient are replaced by residues from a CDR of a nonhuman species such as mouse, rat or rabbit having the desired specificity, affinity and capacity.

In making an engineered antibody, a DNA sequence encoding an antibody molecule of the presently disclosed and claimed inventive concepts is prepared synthetically by established standard methods. For example, according to the phosphoamidine method, oligonucleotides are synthesized, e.g. in an automatic DNA synthesizer, purified, annealed, ligated and cloned in suitable vectors.

The DNA sequence may then be inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

In the vector, the DNA sequence encoding the protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells include, but are not limited to, the LTR promoter, SV 40 promoter, the MT-1 (metallothionein gene) promoter or the adenovirus 2 major late promoter. A suitable promoter for use in insect cells is the polyhedrin promoter. Suitable promoters for use in yeast host cells include promoters from yeast glycolytic genes or alcohol dehydrogenase genes or the TPI1 or ADH2-4c promoters. Suitable promoters for use in filamentous fungus host cells are, for instance, the ADH3 promoter or the tpiA promoter.

The DNA coding sequence may also be operably connected to a suitable terminator, such as the human growth hormone terminator or (for fungal hosts) the TPI1 or ADH3 promoters. The vector may further comprise elements such as polyadenylation signals (e.g. from SV 40 or title adenovirus 5 Elb region), transcriptional enhancer sequences (e.g. the SV 40 enhancer) and translational enhancer sequences (e.g., ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the proteins, the promoter and the terminator, respectively, and to insert them into suitable vectors containing the information necessary for replication, are well known to persons skilled in the art.

To obtain recombinant proteins of the presently disclosed and claimed inventive concepts the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-S-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK (SEQ ID NO:30), thrombin, with the amino acid sequence LVPR/GS (SEQ ID NO:31), or *Acharombacter lyticus*, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines include, but are not limited to, the HEk293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are well known in the art.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes.

The proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

The antibodies of the present invention preferably include one or more modifications which inactivate complement. The term "complement activity" broadly encompasses the biochemical and physiological activities associated with activation of the complement system, individual complement pathway associated molecules, as well as genes encoding these molecules. Therefore, complement activities include, e.g., structure and expression of a gene encoding a complement pathway molecule, biochemical activity (e.g., enzymatic or regulatory) of a complement pathway molecule, cellular activities that initiate or result from activation of the complement system, and presence of serum autoantibodies against complement pathway molecules. In the hSel001 antibody the preferred modification to inactivate complement is a replacement of a lysine residue with alanine at position 342 in the heavy chain constant region CH2. Other substitutions at the same position may include for example any of gly, leu, trp, tyr, pro, thr, ser, met, asp, asn, glu, gln, phe, ile, val, thr, and cys with the proviso that the substitution is also effective in eliminating the ability of the constant region to activate complement.

The terms "complement pathway associated molecules," "complement pathway molecules," and "complement pathway associated proteins" are used interchangeably and refer to the various molecules that play a role in complement activation and the downstream cellular activities mediated by, responsive to, or triggered by the activated complement system. They include initiators of complement pathways (i.e., molecules that directly or indirectly triggers the activation of complement system), molecules that are produced or play a role during complement activation (e.g., complement proteins/enzymes such as C3, C5, C5b-9, Factor B, MASP-1, and MASP-2), complement receptors or inhibitors (e.g., clusterin, vitronectin, CR1, or CD59), and molecules regulated or triggered by the activated complement system (e.g., membrane attack complex-inhibitory factor, MACIF). Thus, in addition to complement proteins noted above, complement pathway associated molecules also include, e.g., C3/C5 convertase regulators (RCA) such as complement receptor type 1 (also termed CR1 or CD35), complement receptor type 2 (also termed CR2 or CD21), membrane cofactor protein (MCP or CD46), and C4bBP; MAC regulators such as vitronectin, clusterin (also termed "SP40,40"), CRP, CD59, and homologous restriction factor (HRF); immunoglobulin chains such as Ig kappa, Ig lambda, or Ig gamma; C1 inhibitor; and other proteins such as CR3, CR4 (CD11b/18), and DAF (CD55).

In an alternative to preparing monoclonal antibody-secreting hybridomas, a monoclonal anti-P-selectin antibody can be identified and isolated by screening a recombinant combinatorial immunoglobulin library (e.g., an antibody phage display library) with the conformational epitopes described herein respectively to thereby isolate immunoglobulin library members that bind P-selectin in accordance with the present invention. Kits for generating and screening phage display libraries are commercially available (e.g., the Pharmacia Recombinant Phage Antibody System, Catalog No. 27-9400-01; and the Stratagene SurJZAP™. Phage Display Kit, Catalog No. 240612).

P-selectin mediates interaction of activated platelets or endothelial cells with blood cells including certain red blood cells (i.e. sickled red cells) and leukocytes including monocytes, neutrophils, eosinophils, $CD4^+$T cells, $CD8^+$T cells, B cells and natural killer (NK) cells. As noted herein, it is known that P-selectin is involved in a number of cellular responses to inflammation resulting from injury, infection, or physicochemical assaults. Atherosclerosis, characterized by atherosclerotic lesions on the inner surfaces of blood vessels, is one example of a condition involving the binding of certain leukocytes to P-selectin-bearing endothelial cells on the inner lining of blood vessel walls.

As indicated above, therapies directed to blocking P-selectin function, for example, using antibodies to P-selectin to prevent the tethering and rolling of leukocytes and adherence of red blood cells (i.e. sickled red cells), could have a profound effect on numerous types of inflammatory and thrombotic diseases. Given its pivotal roll in the initiation of rolling and tethering of leukocytes to the endothelium and platelets, P-selectin is a primary target for therapeutic development to treat inflammatory and thrombotic disorders. For example, the transient nature of the acute phase of sickle cell anemia coupled with the recurrent chronic effects of organ damage and associated complications and morbidity suggests that a therapeutic intervention that exhibits both blocking initial adhesion due to binding of P-selectin and PSGL-1, and inducing dissociation of prior, ongoing or preestablished adhesion, would have novel application to this and other inflammatory and thrombotic diseases. The present invention thus encompasses, in one embodiment, a method of using a conformational antibody binding epitope of P-selectin to screen for and identify "single function"-blocking antibodies to P-selectin which block P-selectin/PSGL-1 binding, and "dual function" antibodies to P-selectin which not only block P-selectin-PSGL-1 binding, but which also cause dissociation of preformed P-selectin/PSGL-1 complex (and thus cell-cell complex), and the use of such antibodies for therapeutic treatment of diseases, such as, but not limited to, inflammatory and thrombotic diseases.

As noted above, novel conformational binding epitopes of P-selectin have been discovered. These binding epitopes have enabled the identification herein of antibodies to human P-selectin which block the binding of PSGL-1 to P-selectin and thus block the function of P-selectin (thus the antibodies may be referred to herein as "function-blocking" antibodies). The discovery of these conformational epitopes have further led to the discovery of dual function anti-P-selectin antibodies which bind with high specificity to the conformational epitope and which not only block the binding of P-selectin and PSGL-1, but which also induce the dissociation of preformed P-selectin/PSGL-1 complexes (i.e., the reversal of P-selectin-PSGL-1 binding) thereby causing the dissociation of cell complexes such as leukocyte/endothelial cell, leukocyte/platelet, lymphocyte/endothelial cell, lymphocyte/platelet, sickled red cell/endothelial cell or sickled red cell/platelet complexes.

The binding regions for some antibodies to P-selectin have been previously mapped using constructs of large functional domains encompassing the lectin, epidermal growth factor (EGF) and consensus repeat (CR) regions of the native protein P-selectin in mouse and human (90, 70, 91-95). These results indicated the primary binding areas for some function-blocking antibodies to P-selectin were in the lectin binding domain, a region that spans amino acid residues 1-120 of the native P-selectin protein, or in the EGF domain spanning amino acids 121-154.

The present disclosure describes the discovery of novel nonlinear (e.g., conformational) epitopes by using mouse/human chimeras containing the lectin, EGF, CR1 and CR2 domains of P-selectin that were probed with function-blocking test antibodies to P-selectin. Previous work has shown that, at a minimum, expression of the lectin and EGF domains are required for proper folding and conformation of P-selectin constructs (91). A comparison of the amino acid sequences of human and mouse P-selectin indicated that there is homology in the lectin domain with a specific number of amino acid residue differences between human and mouse. Herein, three-dimensional (3-D) homology was used to compare the human and mouse lectin, EGF, CR1 and CR2 domains of P-selectin (FIG. 1) to identify amino acid differences between human and mouse P-selectins (sequences and numbering according to the mature proteins).

Where used herein the term "mouse amino acid" refers to an amino acid residue which is found in mouse P-selectin but is not found in the corresponding position in human P-selectin. Where used herein the term "human amino acid" refers to an amino acid residue which is found in human P-selectin but is not found in the corresponding position in mouse P-selectin.

The method used 3-D modeling of P-selectin to compare the positions of amino acid differences between human and mouse P-selectin on the exposed surface of the protein and to identify clusters of amino acid differences between human and mouse in the lectin and EGF domains which are located on the surface of the folded protein. This 3-D method represents clusters of amino acid differences which result from juxtaposition of discontinuous amino acids brought into proximity to one another by folding of the protein. For example, some amino acids will form conformational epitopes by virtue of being on the same surface, e.g. face, of helical structures. Homology comparison of such clusters allowed for selection of amino acid substitutions to test the effect of such changes on the binding of function-blocking (PSGL-1 blocking) antibodies to human P-selectin.

The method further involved mapping of conserved restriction sites in the open reading frames of the cDNA to identify a strategy for constructing chimeric proteins that span the lectin, EGF, CR1 and CR2 domains and would enable substitution of single or multiple amino acids at specific sites in the human or mouse P-selectin to identify those amino acids which optimize antibody binding to human P-selectin. Chimeras were constructed with known molecular cloning techniques, using human and mouse P-selectin N-terminal regions spanning the ATG through CR2 domain with a suitable vector such as pBluescript (pBS-hPsel and pBS-mPsel). The chimeras were inserted into another suitable vector such as pIG1 (pIG-hPsel and pIG-mPsel) where the constructs were fused to the Fc region of human IgG1 containing the hinge, CH2 and CH3 region. These constructs preserved structures that are consistent with the native conformation of P-selectin. Thus domains that were exposed on the surface of the native protein were also present on the chimera constructs and thus served as putative epitopes for binding of test antibodies. Such constructs could be transfected and transiently expressed using molecular and cell expression techniques known to persons having ordinary skill in the art.

Using this method, test antibodies, can be evaluated for binding to the human/mouse chimeras using fluorescence-activated cell sorting (FACS) and surface plasmon resonance (BIACORE) methods known to persons having ordinary skill in the art. The effects of changes in amino acids in various positions in the chimera constructs by substitution of mouse amino acids, for example, into the human sequence, conversely, or human amino acids into the mouse sequence, for example, that abrogated or enabled binding of antibodies directed to human P-selectin were evaluated and thus enabled identification of particular amino acids for optimal binding.

Characterization of Chimera Constructs

Amino acids of mouse P-selectin which have been substituted into the human P-selectin sequence are indicated in boldface in the chimeras described below. Amino acids of human P-selectin which have been substituted into the mouse sequence are indicated in italicized boldface. Substitution of glutamine for histidine is indicated as underlined boldface.

Native Protein Constructs

SEQ ID NO: 1

Human P-selectin lectin, EGF, CR1, CR2 domains
  1 WTYHYSTKAYSWNISRKYCQNRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

SEQ ID NO: 2

Mouse P-selectin lectin, EGF, CR1, CR2 domains-
Amino acid differences from human in boldface.
 42 WTYNYSTKAYSWNNSRVFCRRHFTDLVAIQNKNEIAHLNDVIPFFNSYYWIGIRKINNKW 102 TWVGTNKTLTEEAENWADNEPNNKKNNQDCVEIYIKSNSAPGKWNDEPCFKRKRALCYTA 162 SCQDMSCSNQGECIETIGSYTCSCYPGFYGPECEYVKECGKVNIPQHVLMNCSHPLGEFS 222 FNSQCTFSCAEGYELDGPGELQCLASGIWTNNPPKCDAVQCQSLEAPPHGTMACMHPIAA

282 FAYDSSCKFECQPGYRARGSNTLHCTGSGQWSEPLPTCEAIA

Human/Mouse Chimera Constructs

SEQ ID NO: 3

Chimera-1
(mouse substitutions in human cluster A - N$_4$N$_{14}$V$_{17}$F$_{18}$R$_{20}$R$_{21}$H$_{22}$F$_{23}$)
  1 WTYNYSTKAYSWNNSRVFCRRHFTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

SEQ ID NO: 4

Chimera-2
(human cluster A to I$_{35}$ - mouse thereafter)
  1 WTYHYSTKAYSWNISRKYCQNRYTDLVAIQNKNEIAHLNDVIPFFNSYYWIGIRKINNKW 61 TWVGTNKTLTEEAENWADNEPNNKKNNQDCVEIYIKSNSAPGKWNDEPCFKRKRALCYTA 121 SCQDMSCSNQGECIETIGSYTCSCYPGFYGPECEYVKECGKVNIPQHVLMNCSHPLGEFS 181 FNSQCTFSCAEGYELDGPGELQCLASGIWTNNPPKCDAVQCQSLEAPPHGTMACMHPIAA

241 FAYDSSCKFECQPGYRARGSNTLHCTGSGQWSEPLPTCEAIA

SEQ ID NO: 5

Chimera-3
(substitutions in human cluster A - to mouse N$_4$N$_{14}$V$_{17}$F$_{18}$)
  1 WTYNYSTKAYSWNNSRVFCQNRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

SEQ ID NO: 6

Chimera-4
(substitutions in human cluster A - to mouse R$_{20}$R$_{21}$H$_{22}$F$_{23}$)
  1 WTYHYSTKAYSWNISRKYCRRHFTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

-continued

SEQ ID NO: 7

Chimera-5
(single amino acid change - human $H_4$ to mouse $N_4$)
1 WTYNYSTKAYSWNISRKYCQNRYTDLVAIQNKNEIDYLNKVLPYYSSYYWIGIRKNNKTW

61 TWVGTKKALTNEAENWADNEPNNKRNNEDQVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

SEQ ID NO: 8

Chimera-5Q
(substitution of Q for $H_4$ in cluster A - removes putative glycosylation site)
1 WTYQYSTKAYSWNISRKYCQNRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

SEQ ID NO: 9

Chimera-6
(human sequence to EGF - $S_{121}$ - mouse EGF, CR1 and CR2)
1 WTYHYSTKAYSWNISRKYCQNRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSNQGECIETIGSYTCSCYPGFYGPECEYVKECGKVNIPQHVLMNCSHPLGEFS

181 FNSQCTFSCAEGYELDGPGELQCLASGIWTNNPPKCDAVQCQSLEAPPHGTMACMHPIAA

241 FAYDSSCKFECQPGYRARGSNTLHCTGSGQWSEPLPTCEAIA

SEQ ID NO: 10

Chimera-7
(human sequence to $G_{177}$ - mouse thereafter)
1 WTYHYSTKAYSWNISRKYCQNRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGEFS

181 FNSQCTFSCAEGYELDGPGELQCLASGIWTNNPPKCDAVQCQSLEAPPHGTMACMHPIAA

241 FAYDSSCKFECQPGYRARGSNTLHCTGSGQWSEPLPTCEAIA

SEQ ID NO: 11

Chimera-7B
(human sequence to end of EGF - $V_{156}$ - mouse thereafter)
1 WTYHYSTKAYSWNISRKYCQNRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVKECGKVNIPQHVLMNCSHPLGEFS

181 FNSQCTFSCAEGYELDGPGELQCLASGIWTNNPPKCDAVQCQSLEAPPHGTMACMHPIAA

241 FAYDSSCKFECQPGYRARGSNTLHCTGSGQWSEPLPTCEAIA

SEQ ID NO: 12

Chimera-8
(single amino acid change - human $I_{14}$ to mouse $\mathbf{N}_{14}$)
1 WTYNYSTKAYSWNNSRKYCQNRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

SEQ ID NO: 13

Chimera-9
(single amino acid change - human K$_{17}$ to mouse V$_{17}$)
1 WTYHYSTKAYSWNISRVYCQNRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

SEQ ID NO: 14

Chimera-10
(single amino acid change - human Y$_{18}$ to mouse F$_{18}$)
1 WTYHYSTKAYSWNISRKFCQNRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

SEQ ID NO: 15

Chimera-11
(single amino acid change - human Q$_{20}$ to mouse R$_{20}$)
1 WTYHYSTKAYSWNISRKYCRNRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

SEQ ID NO: 16

Chimera-12
(single amino acid change - human N$_{21}$ to mouse R$_{21}$)
1 WTYHYSTKAYSWNISRKYCQRRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

SEQ ID NO: 17

Chimera-13
(single amino acid change - human R$_{22}$ to mouse H$_{22}$)
1 WTYHYSTKAYSWNISRKYCQNHYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

SEQ ID NO: 18

Chimera-14
(single amino acid change - human Y$_{23}$ to mouse F$_{23}$)
1 WTYHYSTKAYSWNISRKYCQNRFTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

241 FQHQSSCSFSCEEGFALVGPEVVQCTASGVWTAPAPVCK - - -

```
                                                 SEQ ID NO: 19
Chimera-15
(human sequence to cluster C2 - S_97 - mouse thereafter)
  1 WTYHYSTKAYSWNISRKYCQNRYTDLVAIQNKNEIDYLNKVLPYYSSYYWIGIRKNNKTW

61 TWVGTKKALTNEAENWADNEPNNKRNNEDCVEIYIKSNSAPGKWNDEPCFKRKRALCYTA

121 SCQDMSCSNQGECIETIGSYTCSCYPGFYGPECEYVKECGKVNIPQHVLMNCSHPLGEFS

181 FNSQCTFSCAEGYELDGPGELQCLASGIWTNNPPKCDAVQCQSLEAPPHGTMACMHPIAA

241 FAYDSSCKFECQPGYRARGSNTLHCTGSGQWSEPLPTCEAIA

SEQ ID NO: 20
Chimera-16
(substitution of human H_4 I_14 K_17 N_21 R_22 into mouse Cluster A)
  1 WTYHYSTKAYSWNISRKFCRNRFTDLVAIQNKNEIAHLNDVIPFFNSYYWIGIRKINNKW

61 TWVGTNKTLTEEAENWADNEPNNKKNNQDCVEIYIKSNSAPGKWNDEPCFKRKRALCYTA

121 SCQDMSCSNQGECIETIGSYTCSCYPGFYGPECEYVKECGKVNIPQHVLMNCSHPLGEFS

181 FNSQCTFSCAEGYELDGPGELQCLASGIWTNNPPKCDAVQCQSLEAPPHGTMACMHPIAA

242 FAYDSSCKFECQPGYRARGSNTLHCTGSGQWSEPLPTCEAIA

SEQ ID NO: 21
Chimera-17
(human sequence to Cluster B to I_35 - mouse Cluster B to I_42 -
human to CR1 to E_154 - mouse CR1, CR2)
  1 WTYHYSTKAYSWNISRKYCQNRYTDLVAIQNKNEIAHLNDVIPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVKECGKVNIPQHVLMNCSHPLGEFS

181 FNSQCTFSCAEGYELDGPGELQCLASGIWTNNPPKCDAVQCQSLEAPPHGTMACMHPIAA

242 FAYDSSCKFECQPGYRARGSNTLHCTGSGQWSEPLPTCEAIA

SEQ ID NO: 22
Chimera-17B
(human sequence to Cluster B to I_35 - mouse Cluster B to I_42-
human thereafter)
  1 WTYHYSTKAYSWNISRKYCQNRYTDLVAIQNKNEIAHLNDVIPYYSSYYWIGIRKNNKTW

61 TWVGTKKALTNEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

242 FQHQSSCSFSCEEGFALVGPEVVQCTASGVWTAPAPVCK - - -

SEQ ID NO: 23
Chimera-18
(human sequence with mouse cluster C (C1, C2, C3) and
mouse CR1, CR2)
  1 WTYHYSTKAYSWNISRKYCQNRYTDLVAIQNKNEIDYLNKVLPFFNSYYWIGIRKNNKTW

61 TWVGTKKALTNEAENWADNEPNNKRNNEDCVEIYIKSNSAPGKWNDEHCLKKKRALCYTA

121 SCQDMSCSKQGECLETIGNYTCSCYPGFYGPECEYVKECGKVNIPQHVLMNCSHPLGEFS

181 FNSQCTFSCAEGYELDGPGELQCLASGIWTNNPPKCDAVQCQSLEAPPHGTMACMHPIAA

242 FAYDSSCKFECQPGYRARGSNTLHCTGSGQWSEPLPTCEAIA

SEQ ID NO: 24
Chimera-18B
(human sequence with mouse cluster C (C1, C2, C3)
  1 WTYHYSTKAYSWNISRKYCQNRYTDLVAIQNKNEIDYLNKVLPFFNSYYWIGIRKNNKTW

61 TWVGTKKALTNEAENWADNEPNNKRNNEDCVEIYIKSNSAPGKWNDEHCLKKKRALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

242 FQHQSSCSFSCEEGFALVGPEVVQCTASGVWTAPAPVCK - - -
```

```
                                                      SEQ ID NO: 25
Chimera-19
(human sequence with mouse Cluster D and mouse CR1, CR2)
  1 WTYHYSTKAYSWNISRKYCQNRYTDLVAIQNKNEIDYLNKVLPYYSSYYWIGIRKINNKW

61 TWVGTNKTLTEEAENWADNEPNNKRNNEDCVEIYIKSPSAPGKWNDEHCLKKKHALCYTA

121 SCQDMSCSKQGECLETIGNYTCSCYPGFYGPECEYVKECGKVNIPQHVLMNCSHPLGEFS

181 FNSQCTFSCAEGYELDGPGELQCLASGIWTNNPPKCDAVQCQSLEAPPHGTMACMHPIAA

242 FAYDSSCKFECQPGYRARGSNTLHCTGSGQWSEPLPTCEAIA

SEQ ID NO: 26
Chimera-19B
(human sequence with mouse Cluster D)
  1 WTYHYSTKAYSWNISRKYCQNRYTDLVAIQNKNEIDYLNKVLPYYSSYYWIGIRKINNKW

61 TWVGTNKTLTEEAENWADNEPNNKRNNEDCVEIYIKSPSAPGKWNDEHCLKKKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

242 FQHQSSCSFSCEEGFALVGPEVVQCTASGVWTAPAPVCK - - -

SEQ ID NO: 27
Chimera-20
(human sequence with mouse Cluster E and mouse CR1, CR2)
  1 WTYHYSTKAYSWNISRKYCQNRYTDLVAIQNKNEIDYLNKVLPYYSSYYWIGIRKNNKTW

61 TWVGTKKALTNEAENWADNEPNNKRNNEDCVEIYIKSPSAPGKWNDEPCFKRKHALCYTA

121 SCQDMSCSKQGECLETIGNYTCSCYPGFYGPECEYVKECGKVNIPQHVLMNCSHPLGEFS

181 FNSQCTFSCAEGYELDGPGELQCLASGIWTNNPPKCDAVQCQSLEAPPHGTMACMHPIAA

242 FAYDSSCKFECQPGYRARGSNTLHCTGSGQWSEPLPTCEAIA

SEQ ID NO: 28
Chimera-20B
(human sequence with mouse Cluster E)
  1 WTYHYSTKAYSWNISRKYCQNRYTDLVAIQNKNEIDYLNKVLPYYSSYYWIGIRKNNKTW

61 TWVGTKKALTNEAENWADNEPNNKRNNEDCVEIYIKSPSAPGKWNDEPCFKRKHALCYTA

121 SCQDMSCSKQGECLETIGNYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

242 FQHQSSCSFSCEEGFALVGPEVVQCTASGVWTAPAPVCK - - -

SEQ ID NO: 29
Chimera-21
(human sequence with mouse Cluster F)
  1 WTYHYSTKAYSWNISRKYCQNRYTDLVAIQNKNEIDYLNKVLPYYSSYYWIGIRKNNKTW

61 TWVGTKKALTNEAENWADNEPNNKRNNEDCVEIYIKSPSAPGKWNDEHCLKKKHALCYTA

121 SCQDMSCSNQGECIETIGSYTCSCYPGFYGPECEYVRECGELELPQHVLMNCSHPLGNFS

181 FNSQCSFHCTDGYQVNGPSKLECLASGIWTNKPPQCLAAQCPPLKIPERGNMTCLHSAKA

242 FQHQSSCSFSCEEGFALVGPEVVQCTASGVWTAPAPVCK - - -
```

FACS Analysis of Anti-P-Selectin Antibodies to Human/Mouse Chimeras

Antibody binding to human/mouse chimeras of P-selectin was analyzed using FACS analysis on a system such as a BD BIOSCIENCES FACSARIA™ CELL SORTER to measure binding of anti-P-selectin antibodies to human/mouse chimeras which were coupled to beads coated with a goat anti-human Fc antibody. Such beads coated with chimeras were incubated with test anti-P-selectin antibodies that were then detected with anti-mouse Fc or isotype specific antibodies labeled with reporters, such as FITC, suitable for detection by the FACs system.

One-Step Surface Plasmon Resonance (BIACORE)

In one aspect of the presently disclosed and claimed inventive concepts, BIACORE chips were used to capture a test anti-P-selectin antibody. Human-mouse P-selectin chimeras described herein were disposed onto the chip and test antibodies were added to the prebound chip. Binding of the chimeras to test antibodies was measured by resonance response units.

Two-Step Surface Plasmon Resonance (BIACORE) Analysis

In another aspect of the presently disclosed and claimed inventive concepts, a capture chip, such as a BIACORE chip was provided with a goat anti-human IgG Fc polyclonal antibody covalently attached to its surface. P-selectin chimeric human/mouse constructs of the lectin, EGF, CR1 and CR2 domain on a human IgG Fc were injected onto the chip and captured at concentrations that achieve a standardized level of surface coating as measured by the resonance response. The resonance response level achieved after loading each P-selectin chimera construct was designated as a new "secondary baseline" level. Test anti-P-selectin antibodies (e.g., mouse monoclonal anti-P-selectin antibodies G1, G3 and G5) were then injected onto the BIACORE chip and incubated for binding to the P-selectin chimera construct already captured on the surface. The method could be modified to test humanized antibodies by creating P-selectin constructs on mouse IgG Fc and capturing with a goat anti-mouse IgG Fc polyclonal antibody and then probing with test humanized anti-P-selectin antibodies. Antibodies which bind to the P-selectin constructs cause an increase of the resonance response level from the secondary baseline. The resulting increase in resonance response may be measured as "added resonance units (RUs)" and thus indicate the level of binding to the P-selectin construct pre-coated onto the capture chip of the test antibody. Using these methods, optimal requirements for the binding of anti-P-selectin antibodies to P-selectin chimeras were precisely mapped to particular conformational epitopes.

Identification of Dual Function Anti-P-Selectin Antibodies (Antibodies that Both Block and Dissociate Binding of P-Selectin to PSGL-1)

BIACORE analysis was also used to discover dual functionality of specific anti-P-selectin antibodies, i.e., as discussed above, they can both block and dissociate (reverse) binding interactions between P-selectin and PSGL-1. In this method, PSGL-1, or small molecule mimetics of the binding epitope of PSGL-1 such as a biotinylated glycosulfopeptide mimetic (e.g., GSP-6), or chimeric proteins containing the N-terminus of PSGL-1, are captured on a BIACORE chip, such as a streptavidin chip, using methods known to persons having ordinary skill in the art (GSP-6 is a glycosylated, sulfated 18 amino acid peptide mimetic of amino acids 42-60 of the exposed N-terminus of PSGL-1 described in detail in U.S. Pat. No. 6,593,459, for example). First, to demonstrate "function-blocking" ability, in one embodiment, an anti-P-selectin antibody is pre-mixed with soluble P-selectin and incubated for a period to allow formation of the P-selectin/antibody complex. The resulting anti-P-selectin antibody/P-selectin complex is introduced onto the chip bearing the PSGL-1 (or PSGL-1 mimetic) and binding to the PSGL-1 or its mimetic is measured. Anti-P-selectin antibodies, which prevent binding of P-selectin to the PSGL-1 or PSGL-1 mimetic on the chip, are designated as function-blocking antibodies.

Second, anti-P-selectin antibodies which have been shown (by the above-method or another similar method) to be function-blocking antibodies (i.e., which block PSGL-1 binding to P-selectin), can be tested for an additional function, that is, having the ability to dissociate (reverse) binding between preformed P-selectin PSGL-1 complex. Such antibodies can be tested for "dual function" properties using the method of BIACORE analysis discussed herein. In one embodiment, to demonstrate the dual function property, PSGL-1, or a mimetic thereof such as GSP-6, is coupled to a BIACORE chip. P-selectin is then disposed on the chip and allowed to bind to the PSGL-1, or the mimetic. After equilibrium binding of P-selectin to PSGL-1, or the mimetic, is indicated by the sensogram, function-blocking anti-P-selectin antibodies are introduced and the dissociation of P-selectin binding to PSGL-1, or the mimetic is measured by any appropriate method. Such antibodies that are shown to dissociate (i.e., reverse), P-selectin/PSGL-1 binding are designated as "dissociating antibodies" and are characterized as dual function antibodies, i.e., they possess both function-blocking and dissociating properties in disrupting binding of P-selectin to PSGL-1. Such dual function antibodies are a particularly preferred embodiment of the invention as they are especially suitable for therapeutic application as treatments of acute and chronic inflammatory and thrombotic diseases such as are described elsewhere herein.

Discovery of Conformational Epitopes

The three-dimensional (3-D) structure of the mature human and mouse P-selectin proteins were analyzed and compared as to amino acid differences in the lectin and EGF domains. Six clusters of conformational amino acid differences were identified on exposed surfaces of the proteins. These were designated as clusters A, B, C, D, E and F (FIG. 1). The N-termini of human and mouse P-selectins spanning residues 1-35 contain 8 amino acid differences. Cluster A was arbitrarily defined by the boundary of the first amino acid difference ($H_4$) and the last amino acid difference ($Y_{23}$). Cluster A contains 20 amino acids and forms a rigid alpha helix with a cysteine bond near the N-terminus of the protein (see region "1" in FIG. 5). Cluster B (FIG. 1) is a conformational epitope spanning amino acid residues 36-42 and contains 4 amino acid differences between human and mouse P-selectin. Where used herein, the term "conformational epitope" is intended to refer to an epitope which is not recognized under reducing conditions. Clusters C and E (FIG. 1) are conformational and discontinuous and are brought into proximity by folding of the native P-selectin protein. Cluster C has three conformational regions (C1, C2, C3) containing 5 amino acid differences between human and mouse P-selectin. Cluster C1 is separated from C2 by 51 amino acids and cluster C2 is separated from C3 by 15 amino acids. Likewise cluster E has two conformational epitopes (E1, E2) containing five amino acid differences between human and mouse P-selectin with cluster E1 being separated from E2 by 19 amino acids. Clusters A, B, C, D and E lie within the consensus lectin domain of P-selectin (FIG. 1). Cluster F resides in the EGF domain and has 3 amino acid differences out of 11 amino acids. Clusters C1, E1, C2, E2 and C3 encompass key contact residues which have previously been identified for interaction of P-selectin with its physiological ligand PSGL-1 (Somers et al). Clusters A and B are distal to (upstream of) these contact residues.

The open reading frames of cDNAs for human and mouse P-selectin were analyzed to identify common restriction sites that could be used to assemble chimeras spanning the clusters. PCR and chemical DNA synthesis was used to generate cDNAs coding for specific protein or chimera constructs such as SEQ ID NO: 1-29 (described above, and in the Sequence Listing). Restriction cloning was used to construct plasmids coding for the human/mouse chimeras. The chimeras were transiently expressed in COS-7 cells and utilized for FACs and BIACORE analysis. P-selectin chimeras were tested for binding function using BIACORE by analyzing their binding to GSP-6 bound to a BIACORE chip. As noted above, GSP-6 is a small molecule that mimics the N-terminus of human PSGL-1 (96). All tested chimeras bound to the GSP-6 on the chip, though to varying degrees, as mouse P-selectin has a lower binding affinity to human PSGL-1 than does human P-selectin. This indicated that chimeras had maintained function after expression and purification.

FACS Analysis

The results of FACs analysis of anti-P-selectin antibodies, using the constructs or chimeras corresponding to SEQ ID NOs.:1-29 are summarized in Table 1 (below). Three anti-P- selectin test antibodies (G1, G3 and G5) were isolated from hybridomas generated by immunization of mice with a human recombinant P-selectin containing the lectin and EGF domains (90). Previous studies had shown that these antibodies were specific to human P-selectin and that G1 and G3 are function-blocking antibodies and G5 is non-blocking (90, and unpublished data). G1 and G3 were determined herein to bind to human P-selectin (SEQ ID NO:1) but did not bind to mouse P-selectin (SEQ ID NO:2). When the corresponding eight mouse amino acids were substituted in cluster A of the human sequence (Chimera 1, SEQ ID NO:3), binding by G1 antibody was abolished, indicating that at least one or more of the corresponding eight amino acid positions in cluster A was essential for binding of the G1 antibody to P-selectin and that the substitution with the "mouse" amino acids in those one or more positions abolished the binding. To further evaluate the binding specificity of the G1 test antibody, the eight different human amino acids in positions 1-23 were substituted in cluster A of the mouse sequence (SEQ ID NO:4, chimera-2) and G1 binding was achieved. Chimeras containing the human P-selectin lectin domain with mouse amino acid substitutions in the EGF, CR1 and CR2 domains (SEQ ID NO:9, chimera-6), and human sequence through the EGF domain with mouse CR1 and CR2 domains (SEQ ID NO:11, chimera-7B), were bound by G1 and G3 indicating that the primary binding epitopes remained intact after substitution of these mouse amino acids and that the conformation of the antibody binding epitopes were not adversely affected.

Using these methods, the test antibody G3 was shown to bind human P-selectin, did not bind mouse P-selectin and in contrast to G1, bound to SEQ ID NO:3 (chimera-1), indicating that G3 binds to an epitope distinct from the epitope bound by G1. Specifics of the G3 epitope mapping are outlined in Table 1 below.

The test antibody G5, previously shown to be non-blocking, was also analyzed using this method. G5 was shown to be specific for human P-selectin, did not bind mouse P-selectin, and was confirmed as a non-blocking antibody. G5 bound to SEQ ID NO:1 (human P-selectin), SEQ ID NO:3, and SEQ ID NO:10 that spans the EGF domain and includes the first part of CR1 to $N_{178}$, but G5 did not bind to SEQ ID NO:2 (mouse P-selectin) or to SEQ ID NO:9 that spans to $S_{128}$, or to SEQ ID NO:11 that spans to the start of CR1 at $V_{156}$. These results indicate that antibody G5 binds to the first part of CR1 and requires at least amino acids $R_{157}$ through $N_{178}$.

TABLE 1

Results of binding of various antibodies (G1, G3, G4, G5, hSel001) to human and mouse P-selectin and chimera constructs thereof.

| SeqId | Mouse Domains Inserted in Human P-selectin | Human | Mouse | G1 | G3 | G5 | G4 | hSel001 |
|---|---|---|---|---|---|---|---|---|
| 1 | none | 1-279 | 0 | +[1,2,3] | +[1,2,3] | +[1,3] | +[3] | +[2] |
| 2 | all | 0 | 1-282 | −[1,2,3] | −[1,2,3] | −[1,3] | −[3] | −[2] |
| 3 | $A_{4,14,17,18,20,21,22,23}$ | 1-3, 24-279 | 4-23 | −[1,2,3] | +[1,3] | +[1] | −[3] | |
| 4 | B, C, D E, F | 1-35 | 36-282 | +[1,2,3] | −[3] | | +[3] | |
| 5 | $A_{4,14,17,18}$ | 19-279 | 1-18 | −[2] | | | | |
| 6 | $A_{20-23}$ | 1-19, 24-279 | 20-23 | −[2] | | | | |
| 7 | $A_4$ | 1-3, 5-279 | 4 | +[2w,3w] | +[3] | | +[3w] | |
| 8 | none | 1-3, 5-279 | 0 | +[2,3] | +[3] | | +[3] | |
| 9 | F, CR1, CR2 | 1-128 | 129-282 | +[1,2,3] | +[1,3] | −[1,3] | +[3] | |
| 10 | CR1, CR2 | 1-177 | 178-282 | +[1,2,3] | +[1,3] | +[1,3] | +[3] | |
| 11 | CR1, CR2 | 1-156 | 157-282 | +[2] | +[2] | −[2] | | |
| 12 | $A_{14}$ | 1-13, 15-279 | 14 | −[2] | | | | |
| 13 | $A_{17}$ | 1-16, 18-279 | 17 | −[2] | | | | |
| 14 | $A_{18}$ | 1-17, 19-279 | 18 | +[2] | | | | |
| 15 | $A_{20}$ | 1-19, 21-279 | 20 | +[2] | | | | |
| 16 | $A_{21}$ | 1-20, 22-279 | 21 | +[2w] | | | | |
| 17 | $A_{22}$ | 1-21, 23-279 | 22 | −[2] | | | | |
| 18 | $A_{23}$ | 1-22, 24-270 | 23 | +[2] | | | | |
| 19 | C2, E2, C3, F, CR1, CR2 | 1-97 | 98-282 | +[2,3] | −[3] | | +[3] | |
| 20 | B, C, D E, F | 1-35 H/M hybrid | 36-282 | +[2,3] | −[2,3] | | +[3] | +[2] |
| 21 | B, CR1, CR2 | 1-35, 43-156 | 36-42, 157-282 | +[3] | +[3] | −[3] | | |
| 22 | B | 1-35, 43-279 | 36-42 | +[3] | +[3] | +[3] | | |
| 23 | C1, C2, C3, CR1, CR2 | 1-43, 47-97, 99-113, 115-156 | 44-46, 98, 114, 157-282 | +[3] | −[3] | −[3] | | |
| 24 | C1, C2, C3 | 1-43, 47-97, 99-113, 115-279 | 44-46, 98, 114 | | −[3] | +[3] | | |
| 25 | D, CR1, CR2 | 1-55, 72-156 | 56-71, 157-282 | +[3] | +[3] | | | |
| 26 | D | 1-55, 72-279 | 56-71 | +[3] | +[3] | +[3] | | |
| 27 | E1, E2, CR1, CR2 | 1-84, 89-107, 113-156 | 85-88, 108-112, 157-282 | +[3] | +[3] | | | |
| 28 | E1, E2 | 1-84, 89-107, 113-279 | 85-88, 108-112 | | +[3] | +[3] | | |
| 29 | F | 1-128, 140-279 | 129-139 | | +[3] | +[3] | | |
| | | | Critical Amino Acid Positions: | A (4, 14, 17, 21, 22) | C | First part of CR1 (157-164) | A(4, 14, 17, 21, 22) | A (4, 14, 17, 21, 22) |

[1] By FACS,
[2] By BIACORE 1-step,
[3] By BIACORE 2-step,
[w] Weak binding

One-Step Surface Plasmon Resonance (BIACORE)

To further investigate the importance of the cluster A domain (amino acids 4-23) to the binding of G1 antibody to P-selectin, several chimeric constructs were made in which single or multiple mouse amino acids were inserted into the human P-selectin sequence and binding to G1 was analyzed using the surface plasmon resonance ("one-step" BIACORE) methods disclosed herein. The one-step BIACORE binding results are presented in Table 1. The G1 test antibody was captured on a BIACORE chip and the binding of various chimeras was measured as response units. A representative sensogram showing binding of G1 to constructs of human P-selectin (SEQ ID NO:1), mouse P-selectin with human cluster A (SEQ ID NO:4) and mouse P-selectin (SEQ ID NO:2) is shown in FIG. 2. Using this method, it was shown that G1 bound to human P-selectin and to SEQ ID NO:4 (where human amino acids were substituted in cluster A of mouse P-selectin), but did not bind to mouse P-selectin (SEQ ID NO:2), which showed this method to be consistent with previous results.

Mouse P-selectin (SEQ ID NO:2) has a putative glycosylation site (N) at position 4 whereas human P-selectin (SEQ ID NO:1) does not. To test the importance of this difference, SEQ ID NO:1 was substituted at position 4 with N (forming SEQ ID NO:7) and Q (forming SEQ ID NO:8) were made in the human chimera and its effect on G1 antibody binding measured. Inserting N into human P-selectin at position 4 diminished G1 binding suggesting that glycosylation at this site in human P-selectin would interfere with antibody binding. Substitution of glutamine (Q) at this position did not prevent G1 binding.

To further identify amino positions in cluster A that are optimal or essential for G1 antibody binding, single amino acid substitutions of mouse sequence amino acids into the human P-selectin (SEQ ID NO:1) were made, and binding of the resulting chimeras to G1 was measured using the one-step BIACORE method disclosed herein. The chimeras tested (and substitution) were: SEQ ID NO:7 ($H_4N$); SEQ ID NO:12 ($I_{14}N$); SEQ ID NO:13 ($K_{17}V$); SEQ ID NO:14 ($Y_{18}F$); SEQ ID NO:15 ($Q_{20}R$); SEQ ID NO:16 ($N_{21}R$); SEQ ID NO:17 ($R_{22}H$); and SEQ ID NO:18 ($Y_{23}F$). The G1 antibody bound to SEQ ID NO:14, 15 and 18, but did not bind SEQ ID NO:12, 13, and 17 and only weakly to SEQ ID NO:7 and SEQ ID NO:16. This result confirmed the results, shown with SEQ ID NO:20, that amino acid positions 4, 14, 17, 21, and 22 are each individually required positions for G1 binding. In a preferred embodiment, these amino acids are $H_4$, $I_{14}$, $K_{17}$, $N_{21}$ and $R_{22}$, respectively.

Two-Step Surface Plasmon Resonance (BIACORE)

Figure 3:
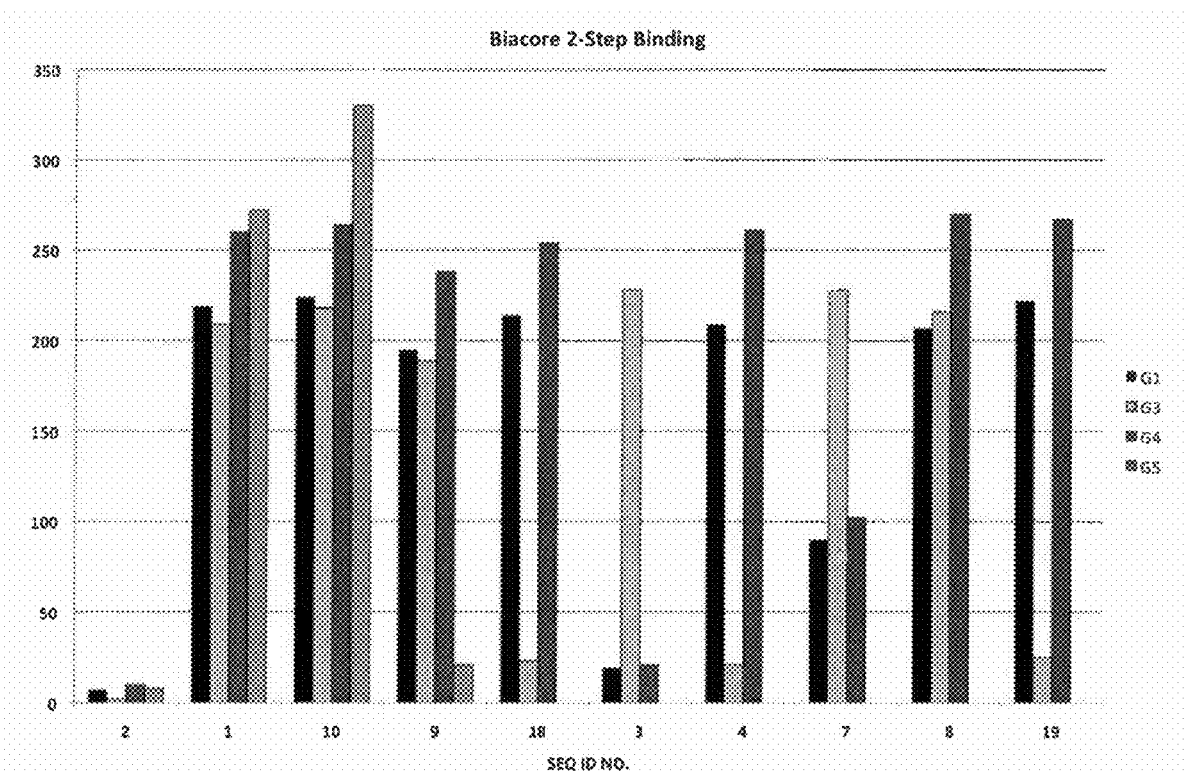
FIG. 3 shows representative two-step BIACORE P-selectin chimera binding data for G1, G3, G4 and G5 anti-P-selectin antibodies binding to SEQ ID NO:1-4, 7-10, 18 and 19. G4 was an uncharacterized anti-P-selectin antibody and demonstrated P-selectin binding properties similar to G1.

To assess G1 binding to additional chimeras and the binding of other anti-P-selectin test antibodies including G3 and G5 (non-blocking), the two-step surface plasmon resonance ("two-step" BIACORE) assay described herein was used. The results of the "two-step" assays for test antibodies G1, G3 and G5 are presented in Table 1, and in FIG. 3. Using this method, none of the test antibodies investigated bound to mouse P-selectin and all bound to human P-selectin demonstrating their specificity to human P-selectin. G1, G3 and G5 test antibodies all bound to SEQ ID NO:11 indicating they all bind to a region spanning the N-terminus through the lectin and EGF domains of human P-selectin. The G5 non-blocking antibody did not bind to SEQ ID NO:9, but did bind SEQ ID NO:10 confirming that G5 binds to the CR1 domain. G5 binding properties were not further evaluated.

Figure 4:
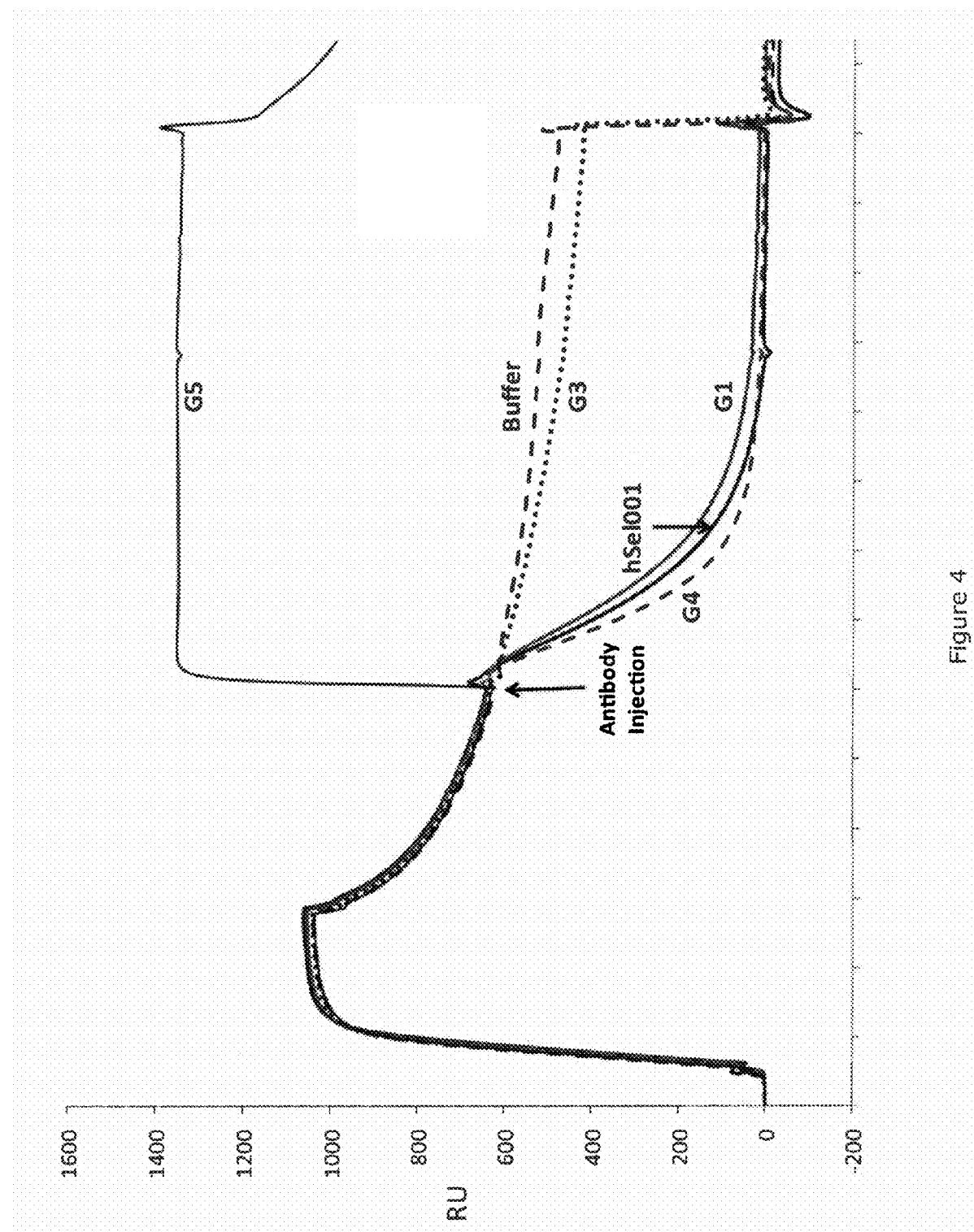
FIG. 4 shows BIACORE sensograms demonstrating dissociation of the preformed P-selectin/PSGL-1 complex upon exposure to dual function anti-P-selectin antibodies (G1, G4, hSEL001). PSGL-1 is represented by GSP-6 peptide, a PSGL-1 mimetic. Initial RU increase shows binding of P-selectin to biotin-GSP-6 coupled to a streptavidin coated BIACORE chip. Once steady state binding of the P-selectin/GSP-6 complex was reached (i.e., after normal dissociation of the complex had reached near-equilibrium), test antibodies G1, G3, and G5 were injected and assessed for dissociation properties. G1 caused dissociation of the preformed P-selectin/GSP-6 complex. G5 bound to the preformed complex, but did not cause its dissociation. G3 did not bind or dissociate the preformed P-selectin/PSGL-1 complex. A new anti-P-selectin antibody, G4, and a humanized anti-P-selectin antibody named hSEL001, also both bound and caused dissociation of the preformed P-selectin/PSGL-1 complex, indicating dual function capabilities.

Further analysis using this method showed that G3 did not bind SEQ ID NO:23, which has mouse amino acids inserted in cluster C1, C2, C3, CR1, and CR2, nor did it bind SEQ ID NO:24 which has mouse amino acids in C1, C2, and C3. G3 also did not bind to other chimeras that had mouse sequence in cluster C, that is SEQ ID NO:19 and SEQ ID NO:20. These results indicate that the blocking test antibody G3 requires cluster C for binding and demonstrates the novel finding that conformational clusters of amino acids brought into proximity by protein folding can serve as binding domains (conformational epitopes) for anti-P-selectin antibodies. The method also confirmed that G3 can block binding of PSGL-1 and P-selectin and thus has function-blocking properties (FIG. 4). However, the method also showed that G3 did not bind to or dissociate (reverse) the binding of P-selectin/PSGL-1 complex (FIG. 4) and thus does not have the dual function properties of the preferred antibodies of the presently disclosed and claimed inventive concepts.

Figure 5:
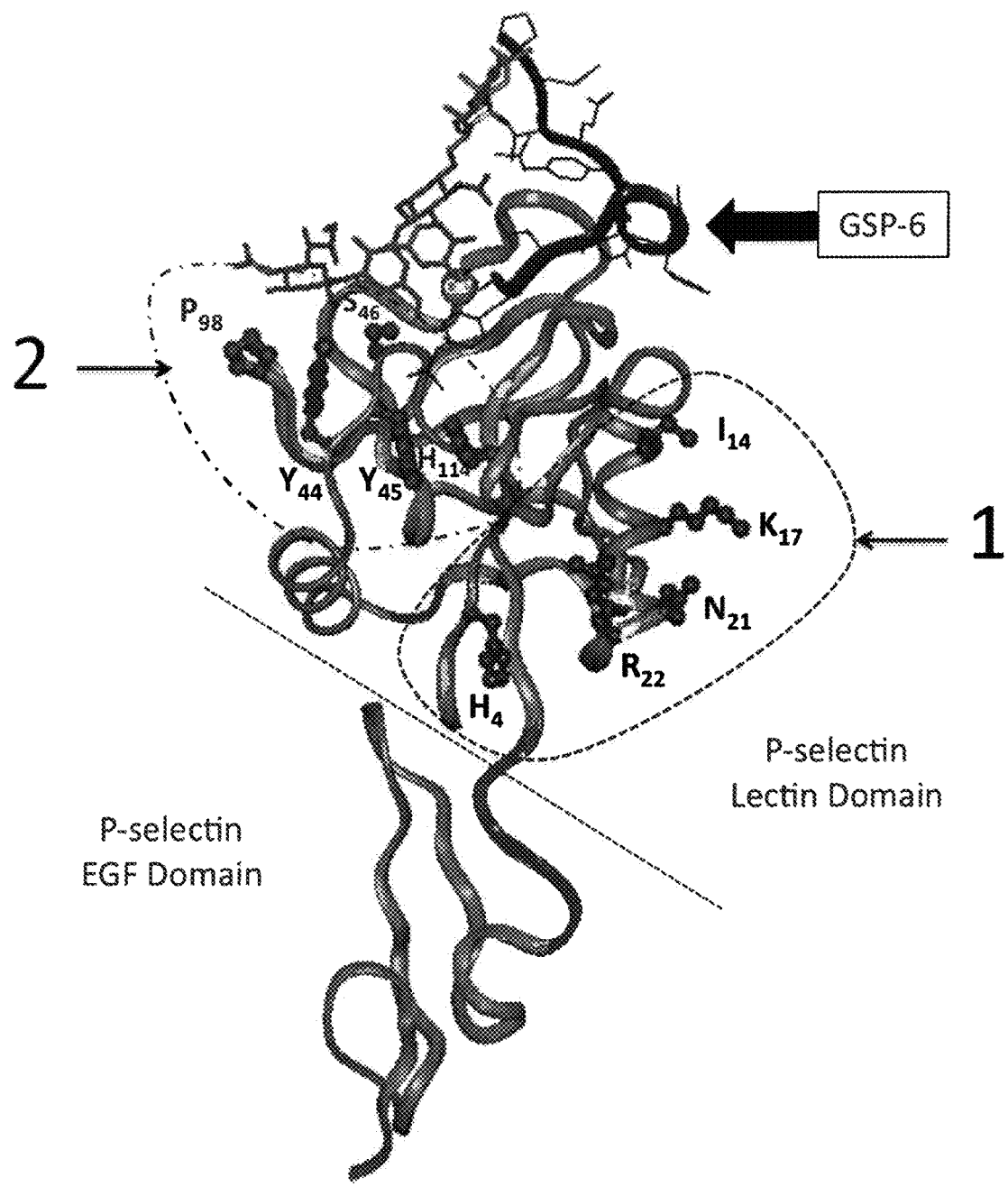
FIG. 5 shows a 3-D representation of a human P-selectin molecule with GSP-6 binding thereto. Lectin and EGF domains are demarcated by a dashed line. Binding region 1 identifies a Cluster A conformational epitope that is distal to the lectin/ligand binding domain. Test antibody G1 bound to region 1, Cluster A. G4, and a humanized anti-P-selectin antibody, hSEL001, also bound region 1, Cluster A.

Amino acid positions which optimize binding of G1 were identified by generating a human/mouse hybrid in cluster A. The hybrid cluster A chimera (SEQ ID NO:20) contains human P-selectin amino acids at positions 4, 14, 17, 21 and 22 (H, I, K, N, and R, respectively) and mouse P-selectin amino acids at positions 18, 20, and 23 (Y, Q, and Y, respectively). As indicated in Table 1, G1 bound SEQ ID NO:20. This result when taken with the previous data indicates that amino acid positions 4, 14, 17, 21, and 22 comprise positions which are each required for optimal binding to P-selectin. These results comprise a novel finding that G1 binds an epitope in the helix structure of cluster A that is distal to the lectin-ligand binding domain contact residues previously identified for P-selectin (71). In a preferred embodiment the amino acids at positions 4, 14, 17, 21, and 22 are H, I, K, N, and R, respectively. 3-D analysis of this epitope revealed a rigid helical structure with the required amino acids occupying sites on the same face of the helix; thus cluster A is designated as comprising a conformational epitope (FIG. 5). BIACORE analysis shown in FIG. 4 confirmed that G1 can block and also dissociate the binding of P-selectin and PSGL-1 and thus this antibody has the dual function properties of the preferred embodiments of the presently disclosed and claimed inventive concepts.

These results indicate that antibodies that bind to a conformational epitope located within amino acids 1-35, and more particularly within amino acids 4-23, of SEQ ID NO:1 which is distal to the lectin-ligand binding domain in human P-selectin, will have unique dual function properties. Without wanting to be bound by theory, it is contemplated that the antibodies which bind to this epitope act by contributing allosteric forces that exert on the lectin-ligand binding interface to induce a conformational change that dissociates P-selectin binding to PSGL-1. Thus G1 is able to bind the distal epitope at cluster A and block and dissociate the complex by binding and disrupting the molecular interactions at the lectin-ligand binding site on P-selectin. In contrast, antibodies such as G3, that bind to an epitope in the lectin-ligand binding domain of P-selectin can block P-selectin binding to PSGL-1 by allosteric hindrance, but cannot cause dissociation of the P-selectin/PSGL-1 complex since the antibody cannot bind to the conformational epitope of Cluster C when it is occupied by the ligand. The test antibody G5 bound to the cluster of P-selectin CR1 and was shown to be non-blocking (FIG. 4).

In summary, antibodies which bind to P-selectin have been characterized as having three possible activities in regard to the interaction of P-selectin, and its ligand, PSGL-1. First, P-selectin antibodies can bind to P-selectin but not interfere with the binding of PSGL-1 to P-selectin ("non-blocking"). For example, as shown herein, the non-blocking antibody G5 binds amino acids 157-164 of SEQ ID NO:1 and requires $R_{157}$, $E_{161}$, $L_{162}$, $E_{163}$ and $L_{164}$ of CR1 for binding. Second, P-selectin antibodies can bind to P-selectin and interfere with the binding of PSGL-1 to P-selectin ("function-blocking"), but not interfere with a preformed P-selectin/PSGL-1 complex. For example, the results described herein also showed that antibody G3 binds to conformational clusters in a different part of P-selectin that span the lectin-ligand binding domain. G3 binds cluster C and requires C1 amino acids $Y_{44}$, $Y_{45}$, $S_{46}$ and C2 amino acid $P_{98}$ and C3 amino acid $H_{114}$ of SEQ ID NO:1 and thus requires a conformational epitope. Third, P-selectin antibodies can bind to P-selectin and block the binding of PSGL-1 to P-selectin (function-blocking antibody) and furthermore can cause reversal of preformed P-selectin/PSGL-1 binding (dissociative binding). Such antibodies are referred to herein as "dual function" antibodies. The results disclosed herein demonstrate, for example, that the test antibody G1 binds a conformational epitope in cluster A of SEQ ID NO:1, and that G1 binding had an absolute requirement for a conformational epitope comprising amino acid positions 4, 14, 17, 21, and 22 of SEQ ID NO:1, preferably wherein those amino acids are H, I, K, N, and R, respectively. As discussed elsewhere herein, substitution of the "human" amino acid (H, I, K, N, and R) at any one of these positions, respectively, with the corresponding "mouse" amino acid (N,N, V, R, and H) will result in the abrogation of binding by the dual function antibodies described and claimed herein.

In another embodiment of the presently disclosed and claimed inventive concepts, a previously uncharacterized mouse monoclonal anti-P-selectin antibody clone designated G4, generated using standard hybridoma methods, was tested for binding to the conformational epitope of cluster A, and was tested for dual function capabilities using the methods described herein. G4 was tested for binding to human/mouse chimeras SEQ ID NOs.:1-4, 7-10, 19 and 20. G4 was shown to bind SEQ ID NO:20 and had similar binding specificity as described for G1 (see Table 1 and FIG. 3). G4 was then shown to block binding of P-selectin to PSGL-1 (FIG. 4) and also to cause dissociation of preformed P-selectin/PSGL-1 complex, thus characterizing G4 as a dual function P-selectin antibody which binds an epitope (in cluster A) which is distal to the lectin-ligand binding domain of P-selectin and blocks and dissociates binding of P-selectin to PSGL-1. The G1 and G4 antibodies thus both bound to an epitope in cluster A and both demonstrated dual function properties. This result demonstrates the use of cluster A or specific binding positions or amino acids thereof as an epitope able to be used to screen anti-P-selectin antibodies for dual function capabilities (as well as for function-blocking activity alone). Such dual function antibodies possess unique properties for therapeutic applications where initiation of P-selectin-mediated adhesion and/or ongoing P-selectin-mediated adhesion in acute or chronic settings may be treated. Using the methods described herein, other antibodies having dual function properties (as well as for function-blocking activity alone) can be identified using the method of screening using the cluster A epitope or specific positions or amino acids thereof.

In another embodiment of the presently disclosed and claimed inventive concepts, a humanized IgG2 anti-P-selectin antibody lacking effector function called hSel001 (a humanized P-selectin binding antibody comprising CDRs of mouse antibody G1 grafted into human framework regions and previously characterized in U.S. patent application Ser. No. 12/516,987) was also screened using the screening method described herein. A summary of the data (Table 1) shows that hSel001 antibody bound to the same chimeras (SEQ ID NO:4, 7, 8, 9, 10, 19 and 20) as antibody G1. hSel001 binding was specific to the conformational epitope described herein located within cluster A. Results showed that antibody hSel001 possesses dual function properties enabling it to both block binding of P-selectin to PSGL-1 and dissociate preformed P-selectin/PSGL-1 complexes (FIG. 4). Thus hSel001 is another antibody encompassed by the presently disclosed and claimed inventive concepts and can be used as a therapeutic treatment for inflammatory and thrombotic diseases as described herein, and wherein P-selectin binding to PSGL-1 is blocked, and dissociation of preformed P-selectin/PSGL-1 complex is promoted.

Cell-Based In Vitro Rolling Assays Under Flow with Human Neutrophils

To further evaluate the blocking and dissociative properties of antibodies G1, G3 and hSel001, cell-based in vitro rolling assays were performed with freshly isolated human neutrophils that were introduced under a flow of 1.0 dyn/cm$^2$ in a flow chamber coated with low and high levels of membrane P-selectin. The low density P-selectin was coated at 0.25 ug/ml and the high density P-selectin was coated at 2 ug/ml. Site densities were determined using $I^{125}$-labeled G1 mAb to be 50 sites/mm$^2$ (low) and 380 sites/mm$^2$ (high). On low density P-selectin, neutrophils rolled at an average velocity of 5 μm/s. On high density P-selectin, neutrophils rolled at an average velocity of 1 μm/s. Neutrophils are introduced in buffer under flow and allowed to begin rolling and tethering. Once equilibrated, test antibodies (G1, G3, hSel001) were introduced in cell-free buffer under flow. There is a dead volume of about 1 minute interval before the antibody reaches the chamber. At 1 minute intervals thereafter, cells remaining bound are counted and expressed as % cells bound. Results were recorded on video microscopy for approximately 0-20 minutes and the data analyzed post run.

Figure 6:
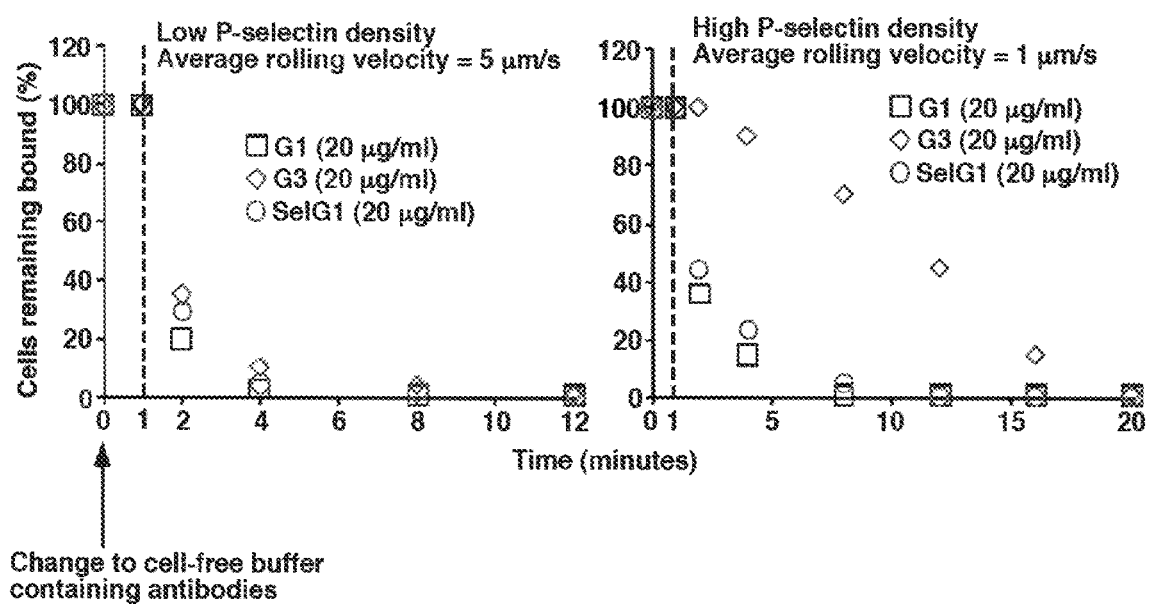
FIG. 6 shows graphs of results of cell-based in vitro rolling assays under flow of human neutrophils on low (A) and high (B) density P-selectin. Results demonstrate blocking and/or dissociation of the preformed P-selectin/PSGL-1 complex and subsequent release of neutrophils upon exposure to antibodies G1, G3 and hSel001. Antibodies were introduced at equivalent concentrations of 20 µg/ml for the duration of the study. There is a lag time of about 1 minute before the antibody reaches the chamber due to the dead volume of the system. At 1-minute intervals thereafter, cells remaining bound were counted and expressed as % cells bound. Panel (A) shows neutrophils rolling at average velocity of 5 µm/s on low density (50 sites/µm$^2$) membrane P-selectin. Panel (B) shows neutrophils rolling at an average velocity of 1 µm/s on high density P-selectin (380 sites/µm$^2$).

Results in FIG. 6 panel (A) showed that neutrophils rolled at a higher velocity on low density P-selectin. Thus as the P-selectin/PSGL-1 complex released due to normal on/off kinetics of the lectin/ligand binding, neutrophils traveled greater distances at higher velocity to the next P-selectin binding site. As the complex releases, the previously occupied P-selectin becomes available for binding by anti-P-selectin antibodies. Thus all three antibodies, G1, G3, and hSel01, showed equivalent blocking functionality over the course of 1-4 minutes.

Results in FIG. 6 panel (B) on high density P-selectin showed that neutrophils roll much slower (1 μm/s) as a greater number of P-selectin binding sites are available. Many neutrophils come to a rolling stop on P-selectin at this density. Under these conditions the murine antibody G1 and the humanized antibody hSel001 were able to release rolling and tethering neutrophils by dissociating the P-selectin/PSGL-1 complex immediately and over the course of 1-8 minutes. In contrast the G3 anti-P-selectin antibody required up to 20 minutes to block rolling neutrophils. This indicated that the G3 antibody was only able to bind unoccupied P-selectin sites and thus block P-selectin/PSGL-1 complexes, but was not able to bind and dissociate the pre-formed complex. These cell-binding assays under flow confirm the BIACORE results reported previously herein which demonstrate that murine antibody G1 and humanized antibody hSel001 both have dual function properties causing both blockage and dissociation of preformed P-selectin/PSGL-1 complexes. Thus the hSel001 antibody has the dual function anti-P-selectin properties of the preferred embodiments of the presently disclosed and claimed inventive concepts.

The isolated dual function antibody claimed as an embodiment of the presently disclosed and claimed inventive concepts does not comprise the murine antibody G1.

Antibodies of the presently disclosed and claimed inventive concepts provided by any of the above described methods are preferably used in the manufacture of a pharmaceutical composition for the therapeutic treatment of a pathological condition, wherein such treatment comprises mitigating, reversion, or inhibiting an inflammatory response or thrombosis.

It is an important objective of the presently disclosed and claimed inventive concepts to use the antibodies, or functionally active fragments or variants of said antibodies for the manufacture of a pharmaceutical composition for prevention and/or treatment of inflammatory responses or diseases or thrombosis such as described herein.

The presently disclosed and claimed inventive concepts in particular are directed to using such single and dual function anti-P-selectin antibodies or antibody fragments as described and identified herein in treatments for inflammatory, thrombotic or other conditions or disorders in primates (including humans) which involve platelet, sickled red cell, leukocyte, lymphocyte, and/or endothelial cell adhesion, wherein the condition or disorder comprises or is associated with (but not limited to) at least one of sickle cell vasoocclusive pain crisis, inflammatory bowel disease (e.g., Crohn's Disease, ulcerative colitis, enteritis), arthritis (e.g., rheumatoid arthritis, osteoarthritis, psoriatic arthritis), graft rejection, graft versus host disease, asthma, chronic obstructive pulmonary disease, psoriasis, dermatitis, sepsis, nephritis, lupus erythematosis, scleroderma, rhinitis, anaphylaxis, diabetes, multiple sclerosis, atherosclerosis, thrombosis, tumor metastasis, allergic reactions, thyroiditis, ischemic reperfusion injury (e.g., due to myocardial infarction, stroke, or organ transplantation), and conditions associated with extensive trauma, or chronic inflammation, such as for example, type IV delayed hypersensitivity, associated for example with infection by Tubercle bacilli, or systematic inflammatory response syndrome, or multiple organ failure. The term "primate" as used herein refers to humans, monkeys, including baboons and cynomolgus monkeys, and apes, the latter including chimpanzees, gorillas, gibbons and orangutans, for example.

In the pharmaceutical composition of a medicament according to the presently disclosed and claimed inventive concepts, the antibodies may be formulated by any of the established methods of formulating pharmaceutical compositions, e.g. as described in the latest edition of Remington's Pharmaceutical Sciences or described elsewhere herein. The composition may typically be in a form suited for local or systemic injection or infusion and may, as such, be formulated with sterile water or an isotonic saline or glucose solution. The compositions may be sterilized by conventional sterilization techniques, which are well known in the art. The resulting aqueous solutions may be packaged for use or filtered under aseptic conditions and lyophilized, the lyophilized preparation being combined with the sterile aqueous solution prior to administration. The composition may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc. The concentration of proteins may vary widely, for example, from less than about 0.01% to as much as 15-20% or more by weight. A unit dosage of the composition may contain for example from about 1 µg to about 1000 mg of an antibody or antibody fragment.

The antibodies or antibody fragments of the presently disclosed and claimed inventive concepts may be administered topically or by injection. Dosages will be prescribed by the physician according to the particular condition and the particular individual to be treated. Dosages and frequency is carefully adapted and adjusted according to parameters determined by the physician in charge. Preferred administration routes may be oral, via inhalation, subcutaneous, intravenous, intramuscular, intratracheal, intravesical, or intraperitoneal injections and may be given per 24 to 48 hours, or per week, every 14 days, every 4 weeks for example in the range of from 0.01-1000 mg, especially 0.1 mg to 100 mg, in particular 1-10 mg per kg body weight. The dose may be administered continuously through a catheter or in individual boluses. The antibody of the invention may be administered in an efficacious quantity such as, but not limited to, the ranges between 1 ng/kg to 1 µg/kg, 0.01 µg/kg to 50 µg/kg, 0.1 µg/kg to 1 µg/kg, 1 µg/kg to 5 µg/kg, 5 µg/kg to 10 µg/kg, 10 µg/kg to 50 µg/kg, 50 µg/kg to 100 µg/kg, 100 mg/kg to 1 mg/kg, 1 mg/kg to 10 mg/kg, or 10 mg/kg to 100 mg/kg body weight.

Pharmaceutical compositions used in the presently disclosed and claimed inventive concepts comprising antibodies described herein may additionally be supplemented by other therapeutic compounds which are routinely prescribed by the physician according to the particular condition and the particular individual to be treated such as an anti-inflammatory drug, wherein said drugs are prescribed by the physician according to the particular condition and the particular individual to be treated.

As noted elsewhere herein, the phenomenon of P-selectin/PSGL-1 binding has functional importance in sickled red cell, endothelial cell leukocyte and platelet interactions, and/or microvesicle adhesion, leukocyte rolling, recruitment, aggregation; leukocyte secretion of cytokines; promotion of coagulation; and other aspects of inflammation, thrombosis, coagulation, immune response, and signal transduction including, but not limited to, sickle cell vasoocclusive pain crisis, inflammatory bowel disease (e.g., Crohn's Disease, ulcerative colitis, enteritis), arthritis (e.g., rheumatoid arthritis, osteoarthritis, psoriatic arthritis), graft rejection, graft versus host disease, asthma, chronic obstructive pulmonary disease, psoriasis, dermatitis, sepsis, nephritis, lupus erythematosis, scleroderma, rhinitis, anaphylaxis, diabetes, multiple sclerosis, atherosclerosis, thrombosis, tumor metastasis, allergic reactions, thyroiditis, ischemic reperfusion injury (e.g., due to myocardial infarction, stroke, or organ transplantation), and conditions associated with extensive trauma, or chronic inflammation, such as for example, type IV delayed hypersensitivity, associated for example with infection by Tubercle bacilli, or systematic inflammatory response syndrome, or multiple organ failure. A neutralizing antibody to P-selectin as described herein will inhibit one or more of these activities in a patient as mediated through P-selectin/PSGL-1 receptor binding (or in the case of sickled red cells, P-selectin/PSGL-1 like receptor binding), in vivo or in vitro, for example. Thus, the inhibition of P-selectin/PSGL-1 binding with a neutralizing antibody described herein is useful in the treatment in a patient of various conditions and disorders including but not limited to, those described herein.

The P-selectin specific antibodies or binding fragments described herein can be linked to another molecule. For example, antibodies may be linked to another peptide or protein, toxin, radioisotope, cytotoxic or cytostatic agents. The antibodies can be linked covalently by chemical crosslinking or by recombinant methods. The antibodies may also be linked to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192; or 4,179,337. The antibodies can be chemically modified by covalent conjugation to a polymer, for example, to increase their stability or half-life. Exemplary polymers and methods to attach them are also shown in U.S. Pat. Nos. 4,766,106; 4,179,337; 4,495,285; and 4,609,546.

The antibodies may also be tagged with a detectable label. A detectable label is a molecule which, by its chemical nature, provides an analytically identifiable signal which allows the detection of a molecular interaction. A protein, including an antibody, has a detectable label if it is covalently or non-covalently bound to a molecule that can be detected directly (e.g., by means of a chromophore, fluorophore, or radioisotope) or indirectly (e.g., by means of catalyzing a reaction producing a colored, luminescent, or fluorescent product). Detectable labels include a radiolabel such as 131I or 99Tc, a heavy metal, or a fluorescent substrate, such as Europium, for example, which may also be attached to antibodies using conventional chemistry. Detectable labels also include enzyme labels such as horseradish peroxidase or alkaline phosphatase. Detectable labels further include chemical moieties such as biotin, which may be detected via binding to a specific cognate detectable moiety, e.g., labeled avidin.

The presently disclosed and claimed inventive concepts are also directed to methods of screening for anti-P-selectin antibodies and binding fragments thereof which block both P-selectin/PSGL-1 binding and/or which cause dissociation of preformed P-selectin/PSGL-1 complexes.

As noted above, the presently disclosed and claimed inventive concepts are directed to antibodies against P-selectin, host cells that produce such anti-P-selectin antibodies, vectors that contain DNA which encode such anti-P-selectin antibody expression and screening methods to identify anti-P-selectin antibodies which block P-selectin/PSGL-1 binding and in a further embodiment has a "dual function" in also causing dissociation of preformed P-selectin/PSGL-1 complex. Thus, in one embodiment the presently disclosed and claimed inventive concepts is directed to methods of identifying anti-P-selectin antibodies that specifically bind to a conformational epitope in amino acids 1-35, and more preferably in amino acids 4-23, of human P-selectin (SEQ ID NO:1) (such as the conformational epitope described herein) and which block PSGL-1, or mimetics thereof, from binding to P-selectin, and which can reverse such binding thereto, thus exhibiting a dual function in blocking selectin-mediated adhesion due to P-selectin/PSGL-1 binding and in causing dissociation of preformed P-selectin/PSGL-1 complexes.

The screening method in a preferred embodiment comprises in vitro assays that can be used to identify anti-P-selectin antibodies that abolish P-selectin/PSGL-1 binding and preferably cause dissociation of preformed P-selectin/PSGL-1 complexes. Test anti-P-selectin antibodies can be screened for dual function capability with a series of assays such as, but not limited to, those described herein which will identify those antibodies that bind to a conformational epitope within amino acids 1-35, and more particularly within amino acids 4-23, of P-selectin, and that block the binding of the PSGL-1 ligand to P-selectin, and which preferably cause dissociation of preformed P-selectin/PSGL-1 complexes. No anti-P-selectin antibodies have heretofore been shown to have the ability to both block PSGL-1 binding to P-selectin and to cause dissociation of preformed P-selectin/PSGL-1 complexes.

In a first step of the screening method, for example, test antibodies generated against P-selectin are assayed for the ability to block binding of PSGL-1 to P-selectin. Test antibodies which block binding of PSGL-1 to P-selectin are screened to determine their ability to cause dissociation of preformed P-selectin/PSGL-1 complexes. Test antibodies identified as having dual function of blocking both PSGL-1 binding to P-selectin, and causing dissociation of P-selectin/PSGL-1 complex comprise particularly preferred embodiments of the presently disclosed and claimed inventive concepts and can be used in the methods of the presently disclosed and claimed inventive concepts.

In one embodiment of the method, test antibodies which block binding of PSGL-1 to P-selectin are first identified using a first screening assay. For example, in a preferred embodiment of the first screening assay, PSGL-1 or a synthetic PSGL-1 mimetic such as GSP-6, or a terminal epitope portion of PSGL-1 able to bind to P-selectin, is bound to a substrate, such as a BIACORE chip, in a method known to persons having ordinary skill in the art. The substrate having the PSGL-1 (or the PSGL-1 mimetic) bound thereto is then exposed to an anti-P-selectin test antibody/P-selectin complex. The binding of the complex to the PSGL-1-substrate is then evaluated. If the test antibody/P-selectin complex does not bind to the PSGL-1 on the substrate, the test antibody is identified as a "function-blocking" antibody.

In an alternative embodiment of the first screening assay, P-selectin, or a portion thereof which maintains the integrity of the conformational epitope, is bound to the substrate. For example, the minimum portion of P-selectin which maintains the conformational epitope comprises the lectin and EGF binding domains of P-selectin. In this embodiment, the P-selectin-substrate is exposed to the test antibody, which binds to form the P-selectin-antibody complex. Then PSGL-1, or a high molecular weight mimetic thereof such as a GSP-6/biotin/avidin complex, is exposed to the P-selectin/test antibody complex and the binding thereto of PSGL-1 (or the mimetic) is evaluated. An antibody which prevents or inhibits the binding of PSGL-1 to P-selectin is identified as a "function-blocking" antibody. When the GSP-6 or PSGL-1 mimetic is bound to the substrate, in a preferred embodiment, it is bound to biotin, and the mimetic-biotin complex is bound to a streptavidin coating on the substrate.

In a preferred embodiment of the second screening assay, either PSGL-1 or a mimetic thereof is bound, as described above, to the substrate (such as a BIACORE chip). P-selectin is then applied to the PSGL-1/substrate to form the P-selectin/PSGL-1 (or mimetic) complex. The test antibody is then applied and dissociation of the complex is measured as a decrease in mass or as Response Units (RU) since P-selectin is being dissociated away. A function-blocking anti-P-selectin antibody, which induces dissociation of the P-selectin/PSGL-1 complex, is designated as a dual function anti-P-selectin antibody. In yet another embodiment of the second assay, the anti-P-selectin antibody itself is bound to the substrate, and a P-selectin/PSGL-1 complex is exposed to it, and dissociation thereof is measured.

In an alternate embodiment of the second screening assay, P-selectin may be bound to a substrate rather than the PSGL-1. PSGL-1 or a high molecular weight mimetic thereof such as a GSP-6/biotin/avidin complex is then exposed to the P-selectin on the substrate and allowed to form a PSGL-1/P-selectin complex. The PSGL-1/P-selectin complex is then exposed to a function-blocking anti-P-selectin antibody and dissociation of the complex is evaluated, for example using a BIACORE method as described elsewhere herein.

Although the presently disclosed and claimed inventive concepts and its advantages have been described in detail, it should be understood that various changes, substitutions and alterations can be made herein without departing from the spirit and scope of the presently disclosed and claimed inventive concepts as defined by the appended claims. Moreover, the scope of the present application is not intended to be limited to the particular embodiments of the process, machine, items of manufacture, compositions of matter, means, methods and steps described in the specification. As one having ordinary skill in the art will readily appreciate from the present disclosure, processes, machines, items of manufacture, compositions of matter, means, methods, or steps, presently existing or later to be developed that perform substantially the same function or achieve substantially the same result as the corresponding embodiments described herein may be utilized according to the presently disclosed and claimed inventive concepts. Accordingly, the appended claims are intended to include within their scope such processes, machines, items of manufacture, compositions of matter, means, methods, or steps.

Each of the references, patents or publications cited herein is expressly incorporated herein by reference in its entirety.

EXAMPLES

Example 1

Preparation of Chimeric or Humanized Antibodies of the Invention

Anti-P-selectin antibodies of the invention can be prepared by replacing one or more of the CDRs of a human antibody sequence with the CDRs from murine mAb G1. Alternatively, all or a part of the heavy and light chain variable regions from the murine mAb G1 can be used to replace the corresponding sequence in a human FR immunoglobulin. The light chain CDR sequences of the murine mAb G1 are set forth in SEQ ID NOs:83 and 33-34, while the heavy chain CDR sequences of the murine mAb G1 are set forth in SEQ ID NOs:35-37.

Figure 7:
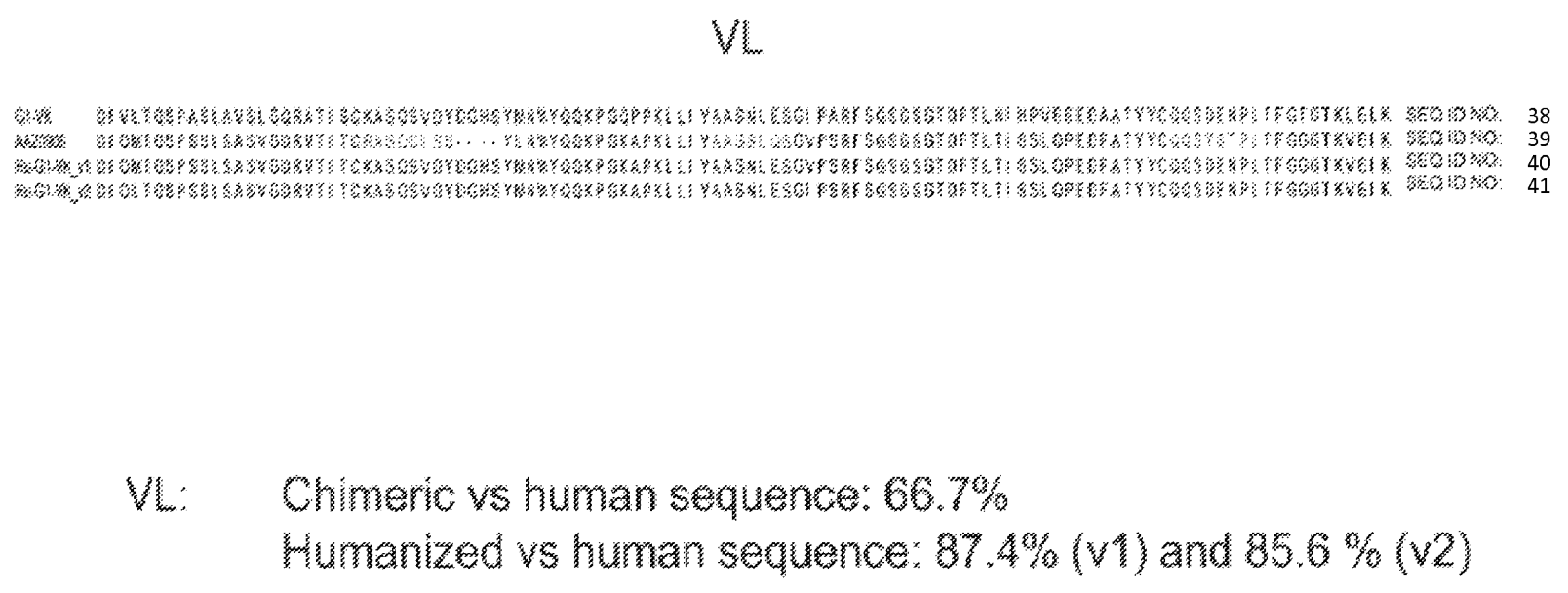

To design the Fv region of the humanized antibody which includes a light chain variable region VL and a heavy chain variable region VH, the human VL and VH sequences that are frequently expressed in the human body and that have a significant sequence identity with the mouse VL and VH sequences respectively are first identified. The human VL sequence indicated by Genbank Accession No. AAZ09096 and the human VH sequence indicated by Genbank Accession No. AAC18323 were selected on the basis of these two factors. Next, as is shown in FIGS. 7 and 8, the complementarity determining regions (CDRs) of the human VL and of VH sequences were replaced by the corresponding CDRs of the anti-P-selectin mouse antibody: amino acids 24-34, 50-56, and 89-97 of SEQ ID NO:39 of the human VL ("AAZ09096") were substituted with amino acids 24-38, 54-60, and 93-101 of SEQ ID NO:38 of the mouse VL ("G1-VK") respectively yielding an "aggressively" humanized antibody VL ("Hu-G1-VK_v1") having the amino acid sequence SEQ ID NO:40; and amino acids 31-35, 50-66, and 99-111 of SEQ ID NO:43 of the human VH (the cleaved form of "AAC18323") were substituted with amino acids 31-35, 50-66, and 99-111 of SEQ ID NO:42 of the mouse VH ("G1-VH") respectively. Additional amino acids of the human VL and VH regions near the CDRs were substituted with corresponding amino acids present in the anti-P-selectin mouse antibody in order to better preserve the P-selectin binding affinity of the humanized antibodies. To identify residues proximal to the CDRs, the human sequences of the light chain ("AAZ09096") and the heavy chain ("AAC18323") were aligned to similar murine sequences 1IQW (a murine VL) and 1NMC (a murine VH) with known three dimensional structures in the Protein Data Bank (PDB). By superimposing the human VL and VH sequences onto the murine VL and VH sequences and then energy minimizing the resulting structure using SPDBV software, amino acids in the human VL and VH proximal to the CDRs were identified: such proximal amino acids may be adjacent to the CDRs or positioned near the CDRs, e.g., within 4-6 Å of amino acids in a CDR, by virtue of the antibody's three-dimensional structure. Four amino acids of the human VL were identified as proximal to the CDRs, including amino acids 3, 4, 30, 58, and 60 of SEQ ID NO:39 and ten amino acids of the human VH were identified as proximal to the CDRs, including amino acids 29, 38, 43, 48, 67, 68, 70, 72, 74, and 98 of SEQ ID NO:43, all of which differed between the respective mouse and human antibody sequences: substitution of the corresponding amino acids in the murine VL and VH were performed at many of these regions, depending on how "conservative" (having fewer human amino acids) or "aggressive" (having more human amino acids) the resulting humanized antibody was desired to be. In a more "conservative" version of the humanized antibody VL (having fewer human residues), amino acids 4 (methionine) and 58 (valine) of SEQ ID NO:39 of the human VL ("AAZ09096") were substituted with amino acids 4 (leucine) and 62 (isoleucine) of SEQ ID NO:38 of the mouse VL ("G1-VK") respectively yielding the "conservatively" humanized antibody VL ("Hu-G1-VK_v2") having the amino acid sequence SEQ ID NO:41. In an "aggressive" version of the humanized antibody VH (having more human amino acids), only amino acids 29 (leucine), 72 (glutamate), 74 (threonine), and 98 (threonine) of SEQ ID NO:43 of the human VH (the cleaved form of "AAC18323") were substituted with amino acids 29 (phenylalanine), 72 (valine), 74 (lysine), and 98 (arginine) of SEQ ID NO:42 of the mouse VH ("G1-VH") respectively, yielding the "aggressively" humanized antibody VH ("Hu-G1-VH_v1") having amino acid sequence SEQ ID NO:44. Similarly, in a "conservative" version of the humanized antibody VH, amino acids 29 (leucine), 48 (methionine), 67 (arginine), 68 (valine), 70 (methionine), 72 (glutamate), 74 (threonine), and 98 (threonine) of SEQ ID NO:43 of the human VH (the cleaved form of "AAC18323") were substituted with amino acids 29 (phenylalanine), 48 (isoleucine), 67 (lysine), 68 (alanine), 70 (leucine), 72 (valine), 74 (lysine), and 98 (arginine) of SEQ ID NO:48 of the mouse VH ("G1-VH") respectively, yielding the "conservatively" humanized antibody VH ("Hu-G1-VH_v2") having amino acid sequence SEQ ID NO:45. Using this procedure, any anti-P-selectin humanized or chimeric antibody, antibody fragment, bifunctional antibody, or antibody derivative having a variable Fv region with CDRs having, e.g., 90%, 95%, 99%, or more sequence identity to amino acids 24-38, 54-60, or 93-101 of SEQ ID NO:38 of the mouse VL ("G1-VK") or amino acids 31-35, 50-66, or 99-111 of SEQ ID NO:42 of the mouse VH ("G1-VH"), which binds P-selectin, may be designed and synthesized using techniques known in the art. Preferably, any anti-P-selectin humanized or chimeric antibody, antibody fragment, bifunctional antibody, or antibody derivative will have valine at the 3rd position, leucine at the 4th position, isoleucine at the 58th position, or alanine at the 60th position of one or more of its VL regions or a phenylalanine at the 29th position, lysine at the 38th position, glutamine at the 43rd position, isoleucine at the 48th position, lysine at the 67th position, alanine at the 68th position, leucine at the 70th position, valine at the 72nd position, lysine at the 74th position, or arginine at the 98th position of one or more of its VH regions.

Example 2

Figure 9:
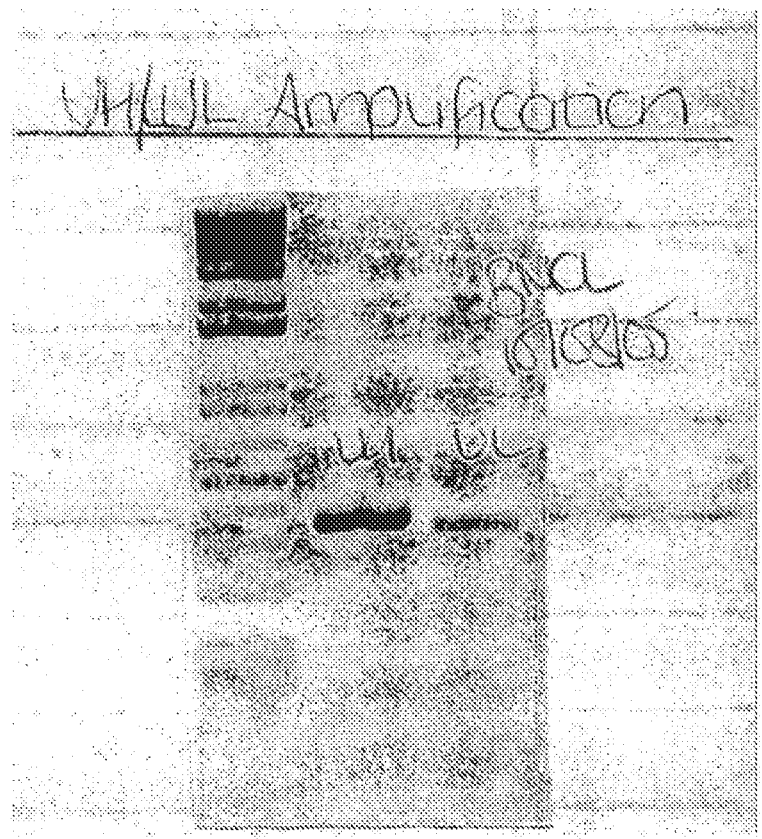
FIG. 9 is a photograph showing the purified variable light (VL) and variable heavy (VH) products that resulted following reverse transcriptase polymerase-chain reaction (RT-PCR) of RNA isolated from the hybridoma cells that express the murine mAbG1.

Cloning of Murine Antibody mRNA was extracted from the hybridoma cell pellets, and agarose gel analysis showed a high yield of the extracted RNA from the pellet. cDNA was created from the RNA by reverse-transcription with an oligo(dT) primer. PCR reactions using variable domain degenerate primers to amplify the VH and VL regions of the monoclonal antibody DNA gave the bands shown in FIG. 9. The purified VH and VL PCR products from RT-PCR were cloned into a sequencing vector and positive transformants were determined by colony PCR. From the RT-PCR, 6 VL and 6 VH clones were identified and the DNA was sequenced. The amino acid sequence was derived from the sequence of the DNA open reading frame. There was a single consensus sequence for both the variable light chain and the variable heavy chain (see Tables 1 and 2).

Table 1: CDR sequences from murine mAb G1

Amino Acid Sequences

VL CDR1: KASQSVDYDGHSYMN (SEQ ID NO:83)

VL CDR2: AASNLES (SEQ ID NO:33)

VL CDR3: QQSDENPLT (SEQ ID NO:34).

VH CDR1: SYDIN (SEQ ID NO:35)

VH CDR2: WIYPGDGSIKYNEKFKG (SEQ ID NO:36)

VH CDR3: RGEYGNYEGAMDY (SEQ ID NO:37)

Table 2: VL and VH Sequences from cloned RT-PCR products from hybridoma cells expressing murine mAb G1. 6 VL clones were identified and sequenced and 6 VH clones were identified and sequenced.

```
Clone VL1
DNA sequence (SEQ ID NO: 46):
GACATTGTGCTAACCCAATCTCCAGCTTCTTTGGCTGTGTCTCTAGGGCA

GAGGGCCACCATCTCCTGCAAGGCCAGCCAAAGTGTTGATTATGATGGTC

ATAGTTATATGAACTGGTACCAACAGAAACCAGGACAGCCACCCAAACTC

CTCATCTATGCTGCATCCAATCTAGAATCTGGGATCCCAGCCAGGTTTAG

TGGCAGTGGGTCTGGGACAGACTTCACCCTCAACATCCATCCTGTGGAGG

AGGAGGATGCTGCAACCTATTACTGTCAGCAAAGTGATGAAAATCCCCTC

ACGTTCGGTACTGGGACCAAGCTGGAGCTGAAACGG

Amino acid sequence (SEQ ID NO: 47):
DIVLTQSPASLAVSLGQRATISCKASQSVDYDGHSYMNWYQQKPGQPPKL

LIYAASNLESGIPARFSGSGSGTDFTLNIHPVEEEDAATYYCQQSDENPL

TFGTGTKLELKR

Clone VL2
DNA sequence (SEQ ID NO: 48):
GACATTGTGCTGACCCAATCTCCAGCTTCTTTGGCTGTGTCTCTAGGGCA

GAGGGCCACCATCTCCTGCAAGGCCAGCCAAAGTGTTGATTATGATGGTC

ATAGTTATATGAACTGGTACCAACAGAAACCAGGACAGCCACCCAAACTC

CTCATCTATGCTGCATCCAATCTAGAATCTGGGATCCCAGCCAGGTTTAG

TGGCAGTGGGTCTGGGACAGACTTCACCCTCAACATCCATCCTGTGGAGG

AGGAGGATGCTGCAACCTATTACTGTCAGCAAAGTGATGAAAATCCCCTC

ACGTTCGGTACTGGGACCAAGCTGGAGCTGAAACGG

Amino acid sequence (SEQ ID NO: 49):
DIVLTQSPASLAVSLGQRATISCKASQSVDYDGHSYMNWYQQKPGQPPKL

LIYAASNLESGIPARFSGSGSGTDFTLNIHPVEEEDAATYYCQQSDENPL

TFGTGTKLELKR

Clone VL3
DNA sequence (SEQ ID NO: 50):
GACATCCAGATGACACAGTCTCCAGCTTCTTTGGCTGTGTCTCTAGGGCA

GAGGGCCACCATCTCCTGCAAGGCCAGCCAAAGTGTTGATTATGATGGTC

ATAGTTATATGAACTGGTACCAACAGAAACCAGGACAGCCACCCAAACTC

CTCATCTATGCTGCATCCAATCTAGAATCTGGGATCCCAGCCAGGTTTAG

TGGCAGTGGGTCTGGGACAGACTTCACCCTCAACATCCATCCTGTGGAGG

AGGAGGATGCTGCAACCTATTACTGTCAGCAAAGTGATGAAAATCCCCTC

ACGTTCGGTACTGGGACCAAGCTGGAGCTGAAACGG

Amino acid sequence (SEQ ID NO: 51):
DIQMTQSPASLAVSLGQRATISCKASQSVDYDGHSYMNWYQQKPGQPPKL

LIYAASNLESGIPARFSGSGSGTDFTLNIHPVEEEDAATYYCQQSDENPL

TFGTGTKLELKR

Clone VL4
DNA sequence (SEQ ID NO: 52):
GACATTGTGCTGACCCAGTCTCCAGCTTCTTTGGCTGTGTCTCTAGGGCA

GAGGGCCACCATCTCCTGCAAGGCCAGCCAAAGTGTTGATTATGATGGTC

ATAGTTATATGAACTGGTACCAACAGAAACCAGGACAGCCACCCAAACTC

CTCATCTATGCTGCATCCAATCTAGAATCTGGGATCCCAGCCAGGTTTAG

TGGCAGTGGGTCTGGGACAGACTTCACCCTCAACATCCATCCTGTGGAGG

AGGAGGATGCTGCAACCTATTACTGTCAGCAAAGTGATGAAAATCCCCTC

ACGTTCGGTACTGGGACCAAGCTGGAGCTGA

Amino acid sequence (SEQ ID NO: 53):
DIVLTQSPASLAVSLGQRATISCKASQSVDYDGHSYMNWYQQKPGQPPKL

LIYAASNLESGIPARFSGSGSGTDFTLNIHPVEEEDAATYYCQQSDENPL

TFGTGTKLEL

Clone VL6
DNA sequence (SEQ ID NO: 54):
GACATTGTGCTAACCCAGTCTCCAGCTTCTTTGGCTGTGTCTCTAGGGCA

GAGGGCCACCATCTCCTGCAAGGCCAGCCAAAGTGTTGATTATGATGGTC

ATAGTTATATGAACTGGTACCAACAGAAACCAGGACAGCCACCCAAACTC

CTCATCTATGCTGCATCCAATCTAGAATCTGGGATCCCAGCCAGGTTTAG

TGGCAGTGGGTCTGGGACAGACTTCACCCTCAACATCCATCCTGTGGAGG

AGGAGGATGCTGCAACCTATTACTGTCAGCAAAGTGATGAAAATCCCCTC

ACGTTCGGTACTGGGACCAAGCTGGAGCTGAAACGG

Amino acid sequence (SEQ ID NO: 55):
DIVLTQSPASLAVSLGQRATISCKASQSVDYDGHSYMNWYQQKPGQPPKL

LIYAASNLESGIPARFSGSGSGTDFTLNIHPVEEEDAATYYCQQSDENPL

TFGTGTKLELKR

Clone VH2
DNA sequence (SEQ ID NO: 56):
AGGTGAAGCTGCAGCAGTCAGGACCTGAGCTGGTGAAGCCTGGGGCTTTA

GTGAAGATATCCTGCAAGGCTTCTGGTTACACCTTCACAAGCTACGATAT

AAATTGGGTGAAGCAGAGGCCTGGACAGGGACTTGAGTGGATTGGATGGA

TTTATCCTGGAGATGGTAGTATTAAGTACAATGAGAAATTCAAGGGCAAG

GCCACACTGACTGTAGACAAATCCTCCAGCACAGCCTACATGCAGGTCAG
```

-continued
```
CAGCCTGACTTCTGAGAATTCTGCAGTCTATTTCTGTGCAAGACGGGGGG
AGTATGGTAACTACGAGGGGGCTATGGACTACTGGGGCCAAGGGACCACG
GTCACCGTCTCCTCA
```

Amino acid sequence (SEQ ID NO: 57)
```
VKLQQSGPELVKPGALVKISCKASGYTFTSYDINWVKQRPGQGLEWIGWI
YPGDGSIKYNEKFKGKATLTVDKSSSTAYMQVSSLTSENSAVYFCARRGE
YGNYEGAMDYWGQGTTVTVSS
```

Clone VH3
DNA sequence (SEQ ID NO: 58):
```
AGGTCAAGCTGCAGCAGTCTGGACCTGAGCTGGTGAAGCCTGGGGCTTTA
GTGAAGATATCCTGCAAGGCTTCTGGTTACACCTTCACAAGCTACGATAT
AAATTGGGTGAAGCAGAGGCCTGGACAGGGACTTGAGTGGATTGGATGGA
TTTATCCTGGAGATGGTAGTATTAAGTACAATGAGAAATTCAAGGGCAAG
GCCACACTGACTGTAGACAAATCCTCCAGCACAGCCTACATGCAGGTCAG
CAGCCTGACTTCTGAGAATTCTGCAGTCTATTTCTGTGCAAGACGGGGGG
AGTATGGTAACTACGAGGGGGCTATGGACTACTGGGGCCAAGGGACCACG
GTCACCGTCTCCTCA
```

Amino acid sequence (SEQ ID NO: 59):
```
VKLQQSGPELVKPGALVKISCKASGYTFTSYDINWVKQRPGQGLEWIGWI
YPGDGSIKYNEKFKGKATLTVDKSSSTAYMQVSSLTSENSAVYFCARRGE
YGNYEGAMDYWGQGTTVTVSS
```

Clone VH4
DNA sequence (SEQ ID NO: 60):
```
AGGTGCAGCTGCAGGAGTCTGGACCTGAGCTGGTGAAGCCTGGGGCTTTA
GTGAAGATATCCTGCAAGGCTTCTGGTTACACCTTCACAAGCTACGATAT
AAATTGGGTGAAGCAGAGGCCTGGACAGGGACTTGAGTGGATTGGATGGA
TTTATCCTGGAGATGGTAGTATTAAGTACAATGAGAAATTCAAGGGCAAG
GCCACACTGACTGTAGACAAATCCTCCAGCACAGCCTACATGCAGGTCAG
CAGCCTGACTTCTGAGAATTCTGCAGTCTATTTCTGTGCAAGACGGGGGG
AGTATGGTAACTACGAGGGGGCTATGGACTACTGGGGCCAAGGGACCACG
GTCACCGTCTCCTCA
```

Amino acid sequence (SEQ ID NO: 61):
```
VQLQESGPELVKPGALVKISCKASGYTFTSYDINWVKQRPGQGLEWIGWI
YPGDGSIKYNEKFKGKATLTVDKSSSTAYMQVSSLTSENSAVYFCARRGE
YGNYEGAMDYWGQGTTVTVSS
```

Clone VH5
DNA sequence (SEQ ID NO: 62):
```
AGGTGAAGCTGCAGCAGTCTGGACCTGAGCTGGTGAAGCCTGGGGCTTTA
GTGAAGATATCCTGCAAGGCTTCTGGTTACACCTTCACAAGCTACGATAT
AAATTGGGTGAAGCAGAGGCCTGGACAGGGACTTGAGTGGATTGGATGGA
TTTATCCTGGAGATGGTAGTATTAAGTACAATGAGAAATTCAAGGGCAAG
GCCACACTGACTGTAGACAAATCCTCCAGCACAGCCTACATGCAGGTCAG
CAGCCTGACTTCTGAGAATTCTGCAGTCTATTTCTGTGCAAGACGGGGGG
AGTATGGTAACTACGAGGGGGCTATGGACTACTGGGGCCAAGGGACCACG
GTCACCGTCTCCTCA
```

Amino acid sequence (SEQ ID NO: 63):
```
VKLQQSGPELVKPGALVKISCKASGYTFTSYDINWVKQRPGQGLEWIGWI
YPGDGSIKYNEKFKGKATLTVDKSSSTAYMQVSSLTSENSAVYFCARRGE
YGNYEGAMDYWGQGTTVTVSS
```

Clone VH6
DNA sequence (SEQ ID NO: 64):
```
AGGTGCAGCTGCAGCAGTCAGGACCTGAACTGGTGAAGCCTGGGGCTTTA
GTGAAGATATCCTGCAAGGCTTCTGGTTACACCTTCACAAGCTACGATAT
AAATTGGGTGAAGCAGAGGCCTGGACAGGGACTTGAGTGGATTGGATGGA
TTTATCCTGGAGATGGTAGTATTAAGTACAATGAGAAATTCAAGGGCAAG
GCCACACTGACTGTAGACAAATCCTCCAGCACAGCCTACATGCAGGTCAG
CAGCCTGACTTCTGAGAATTCTGCAGTCTATTTCTGTGCAAGACGGGGGG
AGTATGGTAACTACGAGGGGGCTATGGACTACTGGGGCCAAGGGACCACG
GTCACCGTCTCCTCA
```

Amino acid sequence (SEQ ID NO: 65):
```
VQLQQSGPELVKPGALVKISCKASGYTFTSYDINWVKQRPGQGLEWIGWI
YPGDGSIKYNEKFKGKATLTVDKSSSTAYMQVSSLTSENSAVYFCARRGE
YGNYEGAMDYWGQGTTVTVSS
```

Consensus Sequences from the Murine mAb VL and VH Clones Sequenced:

Light Chain Variable Domain:

DNA sequence (SEQ ID NO: 66):
```
GACATTGTGCTGACCCAGTCTCCAGCTTCTTTGGCTGTGTCTCTAGGGCA
GAGGGCCACCATCTCCTGCAAGGCCAGCCAAAGTGTTGATTATGATGGTC
ATAGTTATATGAACTGGTACCAACAGAAACCAGGACAGCCACCCAAACTC
CTCATCTATGCTGCATCCAATCTAGAATCTGGGATCCCAGCCAGGTTTAG
TGGCAGTGGGTCTGGGACAGACTTCACCCTCAACATCCATCCTGTGGAGG
AGGAGGATGCTGCAACCTATTACTGTCAGCAAAGTGATGAAAATCCCCTC
ACGTTCGGTACTGGGACCAAGCTGGAGCTGAAACGG
```

Amino acid sequence (SEQ ID NO: 67):
```
DIVLTQSPASLAVSLGQRATISCKASQSVDYDGHSYMNWYQQKPGQPPKL
LIYAASNLESGIPARFSGSGSGTDFTLNIHPVEEEDAATYYCQQSDENPL
TFGTGTKLELKR
```

Heavy chain variable domain:
DNA sequence (SEQ ID NO: 68):*
```
AGGTGAAGCTGCAGCAGTCTGGACCTGAGCTGGTGAAGCCTGGGGCTTTA
GTGAAGATATCCTGCAAGGCTTCTGGTTACACCTTCACAAGCTACGATAT
AAATTGGGTGAAGCAGAGGCCTGGACAGGGACTTGAGTGGATTGGATGGA
TTTATCCTGGAGATGGTAGTATTAAGTACAATGAGAAATTCAAGGGCAAG
GCCACACTGACTGTAGACAAATCCTCCAGCACAGCCTACATGCAGGTCAG
CAGCCTGACTTCTGAGAATTCTGCAGTCTATTTCTGTGCAAGACGGGGGG
AGTATGGTAACTACGAGGGGGCTATGGACTACTGGGGCCAAGGGACCACG
GTCACCGTCTCCTCA
```

-continued

Amino acid sequence (SEQ ID NO: 69):*
VKLQQSGPELVKPGALVKISCKASGYTFTSYDINWVKQRPGQGLEWIGWI

YPGDGSIKYNEKFKGKATLTVDKSSSTAYMQVSSLTSENSAVYFCARRGE

YGNYEGAMDYWGQGTTVTVSS

*The Kin position 2 of this sequence does not match the information from direct N-terminal protein sequencing of the antibody. That sequencing determined that a Q residue is present in that position; a Q residue is also present in the translation of cDNA clones VH4 and VH6 of this report. Therefore, the DNA/translated protein sequences of clones VH4 and VH6 should be regarded as the correct sequence of the heavy chain:

DNA sequence (SEQ ID NO: 70):
AGGTGCAGCTGCAGCAGTCAGGACCTGAACTGGTGAAGCCTGGGCTTTA

GTGAAGATATCCTGCAAGGCTTCTGGTTACACCTTCACAAGCTACGATAT

AAATTGGGTGAAGCAGAGGCCTGGACAGGGACTTGAGTGGATTGGATGGA

TTTATCCTGGAGATGGTAGTATTAAGTACAATGAGAAATTCAAGGGCAAG

GCCACACTGACTGTAGACAAATCCTCCAGCACAGCCTACATGCAGGTCAG

CAGCCTGACTTCTGAGAATTCTGCAGTCTATTTCTGTGCAAGACGGGGGG

AGTATGGTAACTACGAGGGGGCTATGGACTACTGGGGCCAAGGGACCACG

GTCACCGTCTCCTCA

Amino acid sequence (SEQ ID NO: 71):
VQLQQSGPELVKPGALVKISCKASGYTFTSYDINWVKQRPGQGLEWIGWI

YPGDGSIKYNEKFKGKATLTVDKSSSTAYMQVSSLTSENSAVYFCARRGE

YGNYEGAMDYWGQGTTVTVSS

In addition, according to comparison with other antibody sequences, there is likely one more amino acid residue N-terminal to the V residue in the heavy chain. This is supported by the fact that the N-terminus of the heavy-chain had to be "unblocked" prior to direct protein N-terminal sequencing. Sequence comparisons with other antibodies suggest that the missing residue is a Q. Thus, the sequence of the VH would be:

(SEQ ID NO: 72)
QVQLQQSGPELVKPGALVKISCKASGYTFTSYDINWVKQRPGQGLEWIGW

IYPGDGSIKYNEKFKGKATLTVDKSSSTAYMQVSSLTSENSAVYFCARRG

EYGNYEGAMDYWGQGTTVTVSS

G1 N-terminal amino acid sequence Light: Sequencing is taking place at an initial difference level of about 750 pmol. The sequence is: DIVLTQSPASLAVSLGQRATISS(?)KA (SEQ ID NO:73)

Heavy: Sequencing is taking place at an initial difference level of about 165 pmol. The sequence is VQLQQSGPELVKPGALVKISOKASG (SEQ ID NO:74)

Example 3

Sequences for the Humanized P-Selectin Immunoglobulin Based on G1

(SEQ ID NO: 75)
1   D I Q M T Q S P S S L S A S V G D R V T
21  I T C K A S Q S V D Y D G H S Y M N W Y
41  Q Q K P G K A P K L L I Y A A S N L E S
61  G V P S R F S G S G S G T D F T L T I S
81  S L Q P E D F A T Y Y C Q Q S D E N P L
101 T F G G G T K V E I K (SEQ ID NO: 76)
1   D I Q M T Q S P S S L S A S V G D R V T
21  I T C K A S Q S V D Y D G H S Y M N W Y
41  Q Q K P G K A P K L L I Y A A S N L E S
61  G V P S R F S G S G S G T D F T L T I S
81  S L Q P E D F A T Y Y C Q Q S D E N P L
101 T F G G G T K V E I K (SEQ ID NO: 77)
1   D I Q L T Q S P S S L S A S V G D R V T
21  I T C K A S Q S V D Y D G H S Y M N W Y
41  Q Q K P G K A P K L L I Y A A S N L E S
61  G I P S R F S G S G S G T D F T L T I S
81  S L Q P E D F A T Y Y C Q Q S D E N P L
101 T F G G G T K V E I K (SEQ ID NO: 78)
1   D I Q L T Q S P S S L S A S V G D R V T
21  I T C K A S Q A V D Y D G H S Y M N W Y
41  Q Q K P G K A P K L L I Y A A S N L E S
61  G I P S R F S G S G S G T D F T L T I S
81  S L Q P E D F A T Y Y C Q Q S D E N P L
101 T F G G G T K V E I K (SEQ ID NO: 79)
1   Q V Q L V Q S G A E V K K P G A S V K V
21  S C K V S G Y T F T S Y D I N W V R Q A
41  P G K G L E W M G W I Y P G D G S I K Y
61  N E K F K G R V T M T V D K S T D T A Y
81  M E L S S L R S E D T A V Y Y C A R G
101 E Y G N Y E G A M D Y W G Q G T L V T V
121 S S

-continued (SEQ ID NO: 80)
```
  1  Q V Q L V Q S G A E V K K P G A S V K V
 21  S C K V S G Y T F T S Y D I N W V R Q A
 41  P G K G L E W M G W I Y P G D G S I K Y
 61  N E K F K G R V T M T V D K S T D T A Y
 81  M E L S S L R S E D T A V Y Y C A R R G
101  E Y G N Y E G A M D Y W G Q G T L V T V
121  S S
```

(SEQ ID NO: 81)
```
  1  Q V Q L V Q S G A E V K K P G A S V K V
 21  S C K V S G Y T F T S Y D I N W V R Q A
 41  P G K G L E W I G W I Y P G D G S I K Y
 61  N E K F K G K A T L T V D K S T D T A Y
 81  M E L S S L R S E D T A V Y Y C A R R G
101  E Y G N Y E G A M D Y W G Q G T L V T V
121  S S
```

(SEQ ID NO: 82)
```
  1  Q V Q L V Q S G A E V K K P G A S V K V
 21  S C K V S G Y T F T S Y D I N W V R Q A
 41  P G K G L E W I G W I Y P G D G S I K Y
 61  N E K F K G K A T L T V D K S T D T A Y
 81  M E L S S L R S E D T A V Y Y C A R R G
101  E Y G N Y E G A M D Y W G Q G T L V T V
121  S S
```

CDR amino acids are indicated in italics and in bold; mouse framework substitutions are marked in bold and underlined.

Example 4

Determination of the Binding Affinity and Specificity of a Humanized G1 Anti-P-Selectin Antibody Method All experiments were performed on a Biacore 3000, at 25° C., using 20 mM MOPS, pH 7.5, 150 mM NaCl, 1.5 mM CaCl$_2$ and 0.005% Tween-20 as running buffer. Low densities of soluble P-selectin or soluble E-selectin (control protein) were covalently coupled on two different surfaces of a CM-5 chip according to the manufacturer's instructions. The coating density was selected with the aim of achieving a maximum binding response of 100-200 RUs.

Figure 10:
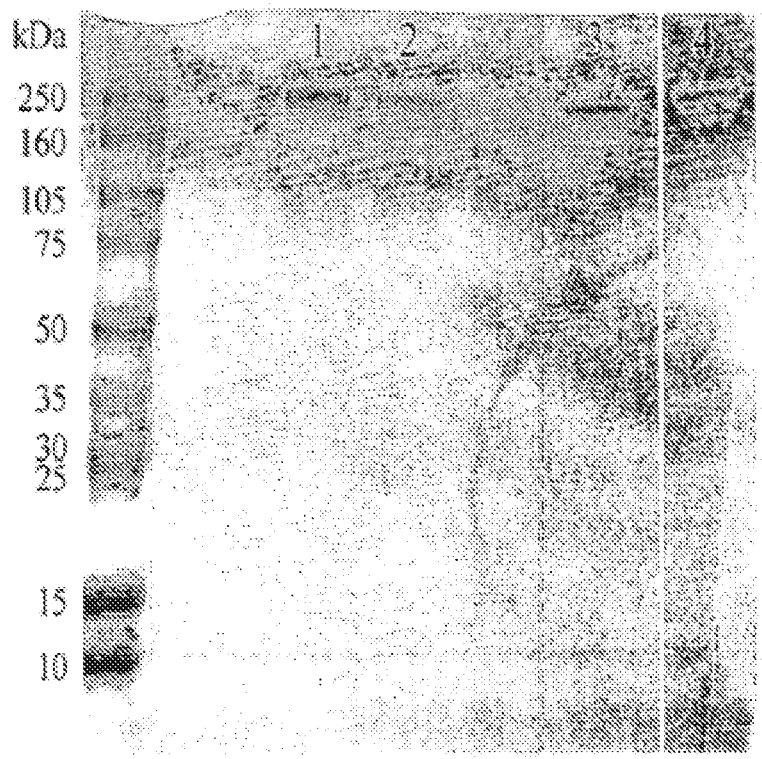
FIG. 10 is a photograph showing the results following expression of a humanized G1 antibody (G1aggr) in stable CHO dhfr$^-$ cells and purification of the G1aggr antibody using one step purification on a protein A column. The photograph shows the purified G1aggr antibody (lane 3) in comparison with the G1 mouse parental monoclonal antibody from which it was derived (lane 4). Lane 1 shows 1.0 µg of human IgG. Lane 2 shows 0.5 µg of human IgG.

A humanized G1 antibody design labeled "aggressive" (G1aggr) was expressed in stable CHO dhfr⁻ cells grown to exhaustion and the media harvested. This design refers to humanized antibody VL sequence "Hu-01-VK_v1" (SEQ ID NO:40) and VH sequence "Hu-G1-VH_v1" (SEQ ID NO:44). The antibody was subjected to one step purification on a protein A column, eluted with 0.1M glycine pH 2.8, immediately neutralized by addition of 0.5M NaPO$_4$, and the yield and concentration determined by A280 protein determination. An aliquot of each antibody (the humanized antibody G1aggr, a G1 mouse parental monoclonal antibody, and two concentrations (1.0 µg and 0.5 µg of human IgG) was run on a 4-20% gradient nonreducing SDS-PAGE and stained with Coomassie blue. The humanized antibody G1aggr was compared with the G1 mouse parental monoclonal antibody from which it was derived. The gel (FIG. 10) shows there was no contamination or breakdown products for the antibodies and all ran as dimers of approximately the same apparent molecular weight.

Figure 11:
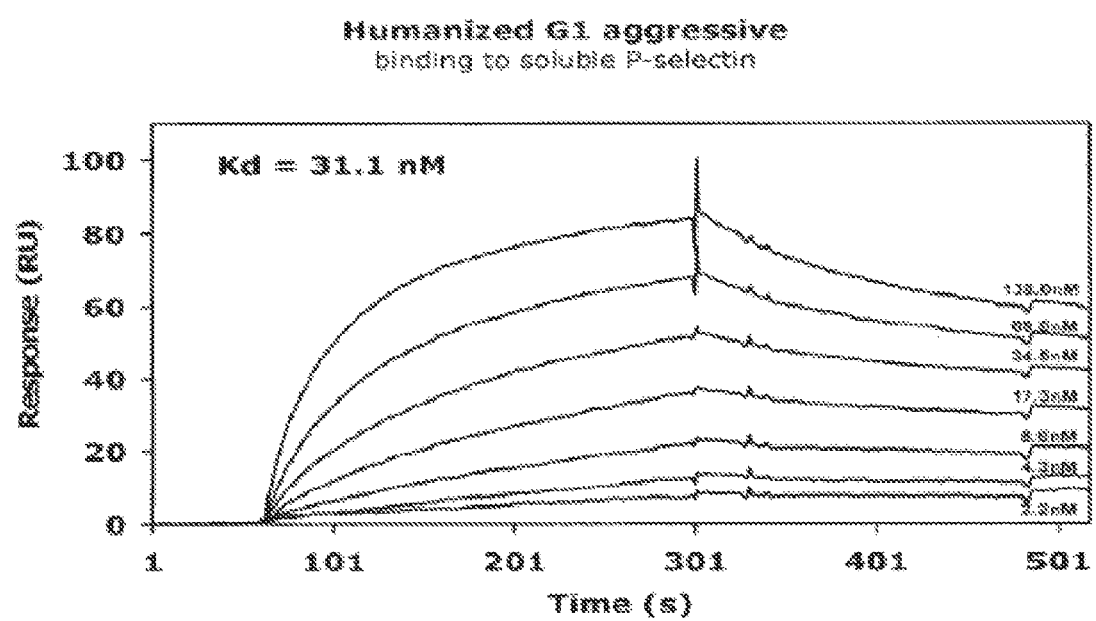
FIG. 11 is a graph showing the equilibrium affinity of the indicated concentrations of humanized antibody G1aggr for soluble P-selectin.

Solutions containing G1aggr and the G1 mouse parental monoclonal antibody were diluted and injected onto the CM-5 chip at a flow rate of 30 µl/min for 4 minutes, followed by 3 min to allow for dissociation, at which time the bound antibody was eluted with a 10 µl injection of 10 mM Acetate pH 4.5, 100 mM NaCl at a flow rate of 10 µl/min. A series of concentrations of both antibodies were injected over the soluble P-selectin and the soluble E-selectin surfaces until saturating binding was observed. The data were analyzed using the Biaevaluation software v 4.1. Sensorgrams from the different cycles were overlaid and the data for all curves of one antibody were simultaneously fitted to a Bivalent analyte model (see FIG. 11). The equilibrium affinity was calculated from the on-rates and off-rates obtained from this analysis.

Based on these analyses, the apparent $K_d$ for the humanized G1aggr was calculated to be 31.1 nM. This compared favorably to a calculated $K_d$ for the parental G1 murine antibody of 24.4 nM. There was no binding observed for either antibody to E-selectin. These results indicate that the humanized G1aggr antibody exhibits specificity for P-selectin and can be used as a P-selectin antagonist.

REFERENCES CITED

1. Springer T A. Traffic signals for lymphocyte recirculation and leukocyte emigration: the multistep paradigm. Cell, 1994. 76:301-314. PubMed: 7507411.
2. McEver R P, Moore K L, Cummings R D. Leukocyte trafficking mediated by selectin-carbohydrate interactions. J Biol. Chem., 1995. 12; 270(19):11025-8. Review. PMID: 7538108.
3. Zimmerman G A, McIntyre T M, Prescott S M. Adhesion and signaling in vascular cell-cell interactions. J Clin Invest., 1996. 15; 98(8):1699-702. No abstract available. PMID: 8878418.
4. Frenette P S. Sickle cell vasoocclusion: heterotypic, multicellular aggregations driven by leukocyte adhesion. Microcirculation, 2004. 11(2):167-77. Review. PMID: 15280090.
5. Weyrich A S, Ma X Y, Lefer D J, Albertine K H, Lefer A M. In vivo neutralization of P-selectin protects feline heart and endothelium in myocardial ischemia and reperfusion injury. J Clin Invest., 1993. 91(6):2620-9. PMID: 7685773.
6. Lefer D J. Pharmacology of selectin inhibitors in ischemia/reperfusion states. Annu Rev Pharmacol Toxicol., 2000. 40:283-94. Review. PMID: 10836137.
7. Singbartl K, Green S A, Ley K. Blocking P-selectin protects from ischemia/reperfusion-induced acute renal failure. FASEB J., 2000. 14(1):48-54. PMID: 10627279.
8. Palabrica T, Lobb R, Furie B C, Aronovitz M, Benjamin C, Hsu Y M, Sajer S A, Furie B. Leukocyte accumulation promoting fibrin deposition is mediated in vivo by P-selectin on adherent platelets. Nature, 1992. 29; 359(6398):848-51. PMID: 1279433.
9. Burger P C, Wagner D D. Platelet P-selectin facilitates atherosclerotic lesion development. Blood, 2003. 1; 101 (7):2661-6. Epub 2002 Dec. 12. PMID: 12480714.
10. Théorêt J F, Bienvenu J G, Kumar A, Merhi Y. P-selectin antagonism with recombinant p-selectin glycoprotein ligand-1 (rPSGL-Ig) inhibits circulating activated platelet binding to neutrophils induced by damaged arterial surfaces. J Pharmacol Exp Ther., 2001. 298(2):658-64. PMID: 11454928.
11. Kumar A, Villani M P, Patel U K, Keith J C Jr, Schaub R G. Recombinant soluble form of PSGL-1 accelerates thrombolysis and prevents reocclusion in a porcine model. Circulation, 1999. 16; 99(10):1363-9. PMID: 10077522.
12. Romano S J. Selectin antagonists: therapeutic potential in asthma and COPD. Treat Respir Med., 2005. 4(2):85-94. Review. PMID: 15813660.
13. Grober J S, Bowen B L, Ebling H, Athey B, Thompson C B, Fox D A, Stoolman L M. Monocyte-endothelial adhesion in chronic rheumatoid arthritis. In situ detection of selectin and integrin-dependent interactions. J Clin Invest., 1993. 91(6):2609-19. PMID: 7685772.
14. Friedrich M, Bock D, Philipp S, Ludwig N, Sabat R, Wolk K, Schroeter-Maas S, Aydt E, Kang S, Dam T N, Zahlten R, Sterry W, Wolff G. Pan-selectin antagonism improves psoriasis manifestation in mice and man. Arch Dermatol Res., 2006. 297(8):345-51. Epub 2005 Dec. 16. PMID: 16362415.
15. Johnson B A, Haines G K, Harlow L A, Koch A E. Adhesion molecule expression in human synovial tissue. Arthritis Rheum, 1993. 36(2):137-46. PMID: 7679271.
16. Bevilacqua M P, Nelson R M. Selectins. J Clin Invest., 1993. 91(2):379-87. Review. PMID: 7679406.
17. McEver R P, Beckstead J H, Moore K L, Marshall-Carlson L, Bainton D F. GMP-140, a platelet alpha-granule membrane protein, is also synthesized by vascular endothelial cells and is localized in Weibel-Palade bodies. J Clin Invest., 1989. 84(1):92-9. PMID: 2472431.
18. Sickle cell disease: screening, diagnosis, management, and counseling in newborns and infants. Clinical Practice Guideline No. 6. AHCPR Pub. No. 93-0562. Rockville, Md.: Agency for Health Care Policy and Research, Public Health Service, U.S. Department of Health and Human Services. April 1993 [cited; Available from: www.ncbi.nlm.nih.gov/books/bv.fcgi?rid=hstat6.chapter.16946.
19. Nietert, P J, Silverstein M D, Abboud M R. Sickle cell anaemia: epidemiology and cost of illness. Pharmacoeconomics, 2002. 20(6): p. 357-66. PMID: 12052095.
20. Bookchin, R M and Lew V L. Pathophysiology of sickle cell anemia. Hematol Oncol Clin North Am, 1996. 10(6): p. 1241-53. PMID: 8956013.
21. NHBLI. [cited; Available from: www.nhlbi.nih.gov/health/dci/Diseases/Sca/SCA_WhatIs.html.
22. NHLBI, The Management of Sickle Cell Disease. NIH Publication No. 022117.
23. FDA Approves Droxia for Sickle Cell Anemia, in FDA Talk Paper. 1998. p. T98-11.
24. NIH, Hydroxurea Treatment for Sickle Cell Disease Feb. 25-27, 2008. National Institutes of Health Consensus Development Conference Statement, Feb. 27, 2008.
25. Gill F M, Sleeper L A, Weiner S J, Brown A K, Bellevue R, Grover R, Pegelow C H, Vichinsky E. Clinical events in the first decade in a cohort of infants with sickle cell disease. Cooperative Study of Sickle Cell Disease. Blood, 1995. 86(2): p. 776-83. PMID: 7921116.
26. Ashley-Koch A, Yang Q, and Olney R S. Sickle hemoglobin (HbS) allele and sickle cell disease: a HuGE review. Am J Epidemiol, 2000. 151(9): p. 839-45. PMID: 10797557.
27. Thomas P W, Higgs D R, and Serjeant G R. Benign clinical course in homozygous sickle cell disease: a search for predictors. J Clin Epidemiol, 1997. February; 50(2): p. 121-6. PMID: 9120504.
28. National Newborn Screening Status Report Updated Mar. 4, 2008.
29. Rice-Evans C, Omorphos S C, and Baysal E. Sickle cell membranes and oxidative damage. Biochem J, 1986. 237 (1): p. 265-9. PMID: 3800879.
30. Wethers, D. L., Sickle cell disease in childhood: Part II. Diagnosis and treatment of major complications and recent advances in treatment. Am Fam Physician. 2000 Sep. 15; 62(6):1309-14. PMID: 11011859.
31. Gladwin M T, Sachev V, Jison M L, Shizukuda Y, Plehn J F, Minter K, Brown B, Coles W A, Nichols J S, Ernst I, Hunter L A, Blackwelder W C, Schechter A N, Rodgers G P, Castro O, Ognibene F P, Pulmonary hypertension as a risk factor for death in patients with sickle cell disease. N Engl J Med, 2004. 350(9): p. 886-95. PMID: 14985486.
32. Saborio P and Scheinman J I, Sickle cell nephropathy. J Am Soc Nephrol, 1999. 10(1): p. 187-92. PMID: 9890326.
33. Charache 5, Eye disease in sickling disorders. Hematol Oncol Clin North Am, 1996. 10(6): p. 1357-62. PMID: 8956022.
34. Kaul, D K, Liu X D, Fabry M E, Nagel R L. Impaired nitric oxide-mediated vasodilation in transgenic sickle mouse. Am J Physiol Heart Circ Physiol, 2000. 278(6): p. H1799-806. PMID: 10843875.
35. Nolan, V G, Adewoye A, Baldwin C, Wang L, Ma Q, Wyszynski D F, Farrell 33, Sebastiani P, Parrer L A, Steinberg M H. Sickle cell leg ulcers: associations with haemolysis and SNPs in Klotho, TEK and genes of the TGF-beta/BMP pathway. Br J Haematol, 2006. 133(5): p. 570-8. PMID: 1661647.
36. Nolan, V G, Wyszynski D F, Farrer L A, Steinberg M H. Hemolysis-associated priapism in sickle cell disease. Blood, 2005. 106(9): p. 3264-7. PMID: 15985542.
37. Gladwin M T and Kato G J. Cardiopulmonary complications of sickle cell disease: role of nitric oxide and hemolytic anemia. Hematology Am Soc Hematol Educ Program, 2005: p. 51-7. PMID: 16304359.
38. Yale, S H, Nagib N, and Guthrie T. Approach to the vasoocclusive crisis in adults with sickle cell disease. Am Fam Physician, 2000. 61(5): p. 1349-56, 1363-4. PMID: 10735342.
39. Heegaard, E D and Brown K E. Human parvovirus B19. Clin Microbiol Rev, 2002. 15(3): p. 485-505. PMID: 12097253.
40. Ballas, S K and Mohandas N. Pathophysiology of vasoocclusion. Hematol Oncol Clin North Am, 1996. 10(6): p. 1221-39. PMID: 8956012.
41. Embury, S H. The not-so-simple process of sickle cell vasoocclusion. Microcirculation, 2004. 11(2): p. 101-13. PMID: 15280086.
42. Conran N and Costa F F. Hemoglobin disorders and endothelial cell interactions. Clin Biochem, 2009. 42(18): p. 1824-38. PMID: 19580799.
43. Chiang E Y and Frenette P S. Sickle cell vaso-occlusion. Hematol Oncol Clin North Am, 2005. 19(5): p. 771-84, Review. PMID: 16214643.
44. Turhan A, Weiss L A, Mohandas N, Collier B S, Freette P S. Primary role for adherent leukocytes in sickle cell vascular occlusion: a new paradigm. Proc Natl Acad Sci USA, 2002. 99(5): p. 3047-51. PMID: 1180644.
45. Hebbel R P, Osarogiagbon R, and Kaul D. The endothelial biology of sickle cell disease: inflammation and a chronic vasculopathy. Microcirculation, 2004. 11(2): p. 129-51. Review. PMID: 15280088.
46. Okpala I, Leukocyte adhesion and the pathophysiology of sickle cell disease. Curr Opin Hematol, 2006. 13(1): p. 40-4. Review. PMID: 16319686.

47. Matsui N M, Borsig L, Rosen S D, Yaghmai M, Varki A, Embury S H P-selectin mediates the adhesion of sickle erythrocytes to the endothelium. Blood, 2001. 98(6): p. 1955-62. PMID: 11535535.
48. Platt O S, Brambilla D J, Rosse W F, Milner P F, Castro O, Steinberg M H, Klug P P. Mortality in sickle cell disease. Life expectancy and risk factors for early death. N Engl J Med, 1994. 330(23): p. 1639-44. PMID: 7993409.
49. Smith J A. Bone disorders in sickle cell disease. Hematol Oncol Clin North Am, 1996. 10(6): p. 1345-56. Review. PMID: 8956021.
50. Platt O S. Prevention and management of stroke in sickle cell anemia. Hematology Am Soc Hematol Educ Program, 2006: p. 54-7. Review. PMID: 17124040.
51. Maitre B, Habibi A, Roudot-Thoraval F, Bachir D, Belghiti D D, Galacteros F, Godeau B. Acute chest syndrome in adults with sickle cell disease. Chest, 2000. 117(5): p. 1386-92. PMID: 1087826.
52. Vichinsky E P, Neumayr L D, Earles A N, Williams R, Lennette E T, Dean D, Nickerson B, Orringer E, McKie V, Bellevue R, Daeschner C, Manci E A. Causes and outcomes of the acute chest syndrome in sickle cell disease. National Acute Chest Syndrome Study Group. N Engl J Med, 2000. 342(25): p. 1855-65. PMID: 10861320.
53. Serjeant G R, Ceulaer C D, Lethbridge R, Morris J, Singhal A, Thomas P W. The painful crisis of homozygous sickle cell disease: clinical features. Br J Haematol, 1994. 87(3): p. 586-91. PMID: 7993801.
54. Platt O S, Thorington B D, Brambilla D J, Milner P F, Rosse W F, Vichinsky E, Kinney T R. Pain in sickle cell disease. Rates and risk factors. N Engl J Med, 1991. 325 (1): p. 11-6. PMID: 1710777.
55. Health Advances, LLC. Application of Selexys Technologies to Inflammatory and Thrombotic Diseases. In Private Study. 2004.
56. McClish D K, Health related quality of life in sickle cell patients: the PiSCES project. Health Qual Life Outcomes, 2005. 3: p. 50. PMID: 16129027.
57. Charache S, Terrin M L, Moore R D, Dover G J, Barton F B, Eckert S V, McMahon R P, Bonds D R. Effect of hydroxyurea on the frequency of painful crises in sickle cell anemia. Investigators of the Multicenter Study of Hydroxyurea in Sickle Cell Anemia. N Engl J Med, 1995. 332(20): p. 1317-22. PMID: 7715639.
58. Patient Information Leaflet: Droxia. Bristol-Myers Squibb Company, 2006.
59. NIH. NIH State-of-the-Science Conference Statement on Hydroxyurea Treatment for Sickle Cell Disease. NIH Consensus and State-of-the Science Statements; Feb. 27-29, 2008. 25(1):1-30. PMID: 18309362.
60. Hydroxyurea for the Treatment of Sickle Cell Disease, Agency for Healthcare Research and Quality; AHRQ Publication No. 08-E007. February 2008.
61. Shet A S, Aras O, Gupta K, Hass M J, Rausch D J, Saba N, Koopmeiners L, Key N S, Hebbel R P. Sickle blood contains tissue factor-positive microparticles derived from endothelial cells and monocytes. Blood, 2003. 102(7): p. 2678-83. PMID: 12805058.
62. Solovey A, Gui L, Key N S, Hebbel R P. Tissue factor expression by endothelial cells in sickle cell anemia. J Clin Invest, 1998. 101(9): p. 1899-904. PMID: 9576754.
63. Solovey A, Lin Y, Browne P, Choong S, Wayner E, Hebbel R P. Circulating activated endothelial cells in sickle cell anemia. N Engl J Med, 1997. 337(22): p. 1584-90. PMID: 9371854.
64. Kaul D K and Hebbel R P. Hypoxia/reoxygenation causes inflammatory response in transgenic sickle mice but not in normal mice. J Clin Invest, 2000. 106(3): p. 411-20. PMID: 10930444.
65. Matsumoto S, Okabe Y, Setoyama H, Takayama K, Ohtsuka J, Funahashi H, Imaoka A, Okada Y, and Umesaki Y. Inflamatory bowel disease-like enteritis and caecitis in a senescence accelerated mouse P1/Yit strain. Gut, 1998. 43:71-78. PMID: 9771408.
66. Kosiewicz M M, Nast C C, Krishnan A, Rivera-Nieves J, Moskaluk C A, Matsumoto S, Kozaiwa K, and Cominelli F. Th1-type responses mediate spontaneous ileitis in a novel murine model of Crohn's disease. J. Clin. Invest., 2001 107:695-702. PMID: 11254669.
67. Rivera-Nieves J, Burcin T L, Olson T S, Morris M A, McDuffie M, Cominelli R and Ley K. Critical role of endothelial P-selectin glycoprotein ligand 1 in chronic murine ileitis. JEM, 2006. 203 (4): 907-917. PMID: 16567389.
68. Moore K L, Stults N L, Diaz S, Smith D F, Cummings R D, Varki A, McEver R P. Identification of a specific glycoprotein ligand for P-selectin (CD62) on myeloid cells. J Cell Biol, 1992; 118:445-456. PMID: 1378449.
69. McEver R P, Cummings R D. Role of PSGL-1 binding to selectins in leukocyte recruitment. J Clin Invest, 1997; 100:597-103. PMID: 9413410.
70. Kansas G S. Selectins and their ligands: current concepts and controversies. Blood, 1996; 88:3259-3287. PMID: 8896391.
71. Somers W S, Tang J, Shaw G D, Camphausen R T. Insights into the molecular basis of leukocyte tethering and rolling revealed by structures of P- and E-selectin bound to SLe(X) and PSGL-1. Cell, 2000. Oct. 27; 103(3):467-79. Erratum in: Cell, 2001. Jun. 29; 105(7):971. PMID: 11081633.
72. Mayadas T N, Johnson R C, Rayburn H, Hynes R O, Wagner D D. Leukocyte rolling and extravasation are severely compromised in P selectin-deficient mice. Cell, 1993. Aug. 13; 74(3):541-54. PMID: 7688665.
73. Xia L, Sperandio M, Yago T, McDaniel J M, Cummings R D, Pearson-White 5, Ley K, McEver R P. P-selectin glycoprotein ligand-1-deficient mice have impaired leukocyte tethering to E-selectin under flow. J Clin Invest, 2002. 109:939-950. PMID: 11927621.
74. Yang J, Hirata T, Croce K, Merrill-Skoloff G, Tchernychev B, Williams E, Flaumenhaft R, Furie B C, Furie B. Targeted gene disruption demonstrates that P-selectin glycoprotein ligand 1 (PSGL-1) is required for P-selectin-mediated but not E-selectin-mediated neutrophil rolling and migration. J Exp Med, 1999. Dec. 20; 190 (12):1769-82. PMID: 10601352
75. Walcheck B, Moore K L, McEver R P, and Kishimoto T K. Neutrophil-neutrophil interactions under hydrodynamic shear stress involve L-selectin and PSGL-1. A mechanism that amplifies initial leukocyte accumulation on P-selectin in vitro. J. Clin. Invest., 1996. 98:1081-1087. PMID: 8787668.
76. Bargatze R F, Kurk S, Butcher E C, Jutila M A. Neutrophils roll on adherent neutrophils bound to cytokine-induced endothelial cells via L-selectin on the rolling cells. J Exp Med., 1994. Nov. 1; 180(5):1785-92. PMID: 7525838.
77. Jung U and Ley K. Mice Lacking Two or All Three Selectins Demonstrate Overlapping and Distinct Functions for Each Selectin. J. Immunol., 1999. 162: 6755-6762. PMID: 10352295.
78. Antibody Engineering, $2^{nd}$ edition., Borrebaeck C A, Ed., Oxford University Press (1995).

79. Sambrook J and Russell D. Molecular Cloning: A Laboratory Manual, 2nd edition, Cold Spring Harbor Laboratory Press (1989).
80. Bodansky M and Bodansky A. The Practice of Peptide Synthesis, 2nd edition., Springer-Verlag, Berlin. 1995.
81. Altschul S F, Gish W, Miller W, Myers E W, Lipman D J. Basic local alignment search tool. J. Mol. Biol., 1990. 215:403-410 PMID: 2231712.
82. Needleman S B, Wunsch C D. A general method applicable to the search for similarities in the amino acid sequence of two proteins. J. Mol. Biol., 1970. 48(3):444-453 PMID: 5420325.
83. Meyers E W and Miller W. Optimal alignments in linear space. Comput. Appl. Biosci., 1988. 4(1):11-17. PMID: 3382986.
84. Tatusova T A and Madden T L. BLAST 2 Sequences, a new tool for comparing protein and nucleotide sequences. FEMS Microbiol. Lett., 1999. 174(2):247-250. PMID: 10339815.
85. Kohler G and Milstein C. Continuous cultures of fused cells secreting antibody of predefined specificity. Nature, 1975. 256(5517): 495-7. PMID: 1172191.
86. Ausubel F M. Current Protocols in Molecular Biology, Greene Publishing Associates and Wiley Interscience, N.Y., 1989).
87. Wigler M, Pellicer A, Silverstein S, Axel R. Biochemical transfer of single-copy eukaryotic genes using total cellular DNA as donor. Cell, 1978. 14(3):725-31. PMID: 210957.
88. Neumann E, Schaefer-Ridder M, Wang Y, Hofschneider P H. EMBO, 1982. J. 1(7):841-5. PMID: 6329708.
89. Harlow E and Lane D. Antibodies: A Laboratory Manual, Cold Spring Harbor Laboratory Press, New York, 1988.
90. Geng J G, Moore K L, Johnson A E, McEver R P. Neutrophil recognition requires a $Ca^{2+}$-induced conformational change in the lectin domain of GMP-140. J. Biol. Chem., 1991. 266(33): 22313-22318. PMID: 1718992.
91. Mehta P, Patel K D, Laue T M, Erickson H P, Mcever R P. Souluble monomeric P-selectin containing only the lectin and epidermal growth factor domains binds to P-selectin glycoprotein ligand-1 on leukocytes. Blood, 1997. Sep. 15; 90(6): 2381-9. PMID: 9310489.
92. Hirose M, Kawashima H, Miyasaka M. A functional epitope on P-selectin that supports binding of P-selectin to P-selectin glycoprotein ligand-1 but not to sialyl Lewis X oligosaccharides. Int. Immunol., 1998. May; 10(5): 639-49. PMID: 9645612.
93. Ruchaud-Sparangano M H, Malaud E, Gayet O, Chignier E, Buckland R, McGregor J L. Mapping the epitope of a functional P-selectin monoclonal antibody (LYP20) to a short complement-like repeat (SCR 4) domain: use of human-mouse chimera and homologue-replacement mutagenesis. Biochem. J., 1998. 1; 332(Pt2):309-14. PMID: 9601057.
94. Chestnut, R M, Polley, M J, Paulson, J C, Hones, T, Saldanha, J W, Bendig, M M, Kriegler, M. Perez, C, Bayer, R Nunn, M. Antibodies to P-selectin and Their Uses. U.S. Pat. No. 5,800,815. Sep. 1, 1998.
95. Berg E L, Fromm C, Melrose J, Tsurushita N. Antibodies cross-reactive with E- and P-selectin block both E- and P-selectin functions. Blood, 1995. Jan. 1; 85(1):31-7. PMID: 7528571.
96. Leppanen A, Mehta P, Ouyang Y B, Ju T, Helin J, Moore K L, van Die I, Canfield W M, McEver R P, Cummings R D. 1999. A novel glycosulfopeptide binds to P-selectin and inhibits leukocyte adhesion to P-selectin. J Biol Chem August 27; 274(35):24838-48. PMID: 10455156.

What is claimed is:

1. A method of treating or inhibiting an inflammatory or thrombotic condition or disorder in a subject in need of such therapy, comprising:
    administering to the subject a therapeutically-effective amount of an antibody or binding fragment thereof which specifically binds to a conformational epitope of P-selectin which is within amino acid positions 1-35 of SEQ ID NO:1,
    wherein the antibody or binding fragment thereof has the ability to block the binding of P-selectin glycoprotein ligand-1 (PSGL-1) to P-selectin and the ability to cause dissociation of a preformed P-selectin-PSGL-1 complex;
    wherein the amino acids in amino acid positions 4, 14, 17, 21, and 22 are H, I, K, N, and R, respectively;
    provided that the antibody or binding fragment thereof is not G1 antibody, the G1 antibody comprising variable light chains each individually having an amino acid sequence selected from the group consisting of SEQ ID NOs: 47, 51, 53, 55, and 67, and further comprising variable heavy chains each individually having an amino acid sequence selected from the group consisting of SEQ ID NOs: 61, 65, and 69;
    further provided that the antibody or binding fragment thereof is not hSel001 antibody comprising variable light chains each individually having an amino acid sequence of SEQ ID NO:40 and variable heavy chains each individually having an amino acid sequence of SEQ ID NO:44; further provided that the antibody or binding fragment thereof is not a binding fragment of the G1 antibody; or a binding fragment of the hSel001 antibody.

2. The method of claim 1 wherein the conformational epitope is within amino acids 4-23 of SEQ ID NO:1.

3. The method of claim 1 wherein binding is abrogated when any one or more of amino acid positions 4, 14, 17, 21, or 22 is substituted with N, N, V, R, or H, respectively.

4. The method of claim 1 wherein the conformational epitope further comprises amino acid positions 20 and 23 of SEQ ID NO:1.

5. The method of claim 1 wherein the antibody or binding fragment thereof has the ability to cause dissociation of cell-cell binding between activated endothelial cells and leukocytes, lymphocytes, sickled red cells, and/or platelets.

6. The method of claim 1 wherein the antibody or binding fragment thereof has the ability to cause dissociation of cell-cell binding between activated platelets and leukocytes, lymphocytes, sickled red cells, and/or platelets.

7. The method of claim 1 wherein the antibody or binding fragment thereof has the ability to block the function of P-selectin by inhibiting the binding of activated endothelial cells to leukocytes, lymphocytes, sickled red cells, and/or platelets.

8. The method of claim 1 wherein the antibody or binding fragment thereof has the ability to block the function of P-selectin by inhibiting the binding of activated platelets to leukocytes, lymphocytes, sickled red cells, and/or platelets.

9. The method of claim 1 wherein the antibody or binding fragment thereof is monoclonal.

10. The method of claim 1 wherein the antibody or fragment thereof is chimeric, human, or humanized.

11. The method of claim 1 wherein the antibody or binding fragment thereof comprises an immunoglobulin selected from the class consisting of IgA, IgD, IgE, IgG, and IgM.

12. The method of claim 11 wherein the antibody or fragment thereof is IgG1, IgG2, IgG3, IgG4, or an IgG2/G4 chimera.

13. The method of claim 1 wherein the binding fragment comprises at least one of a Fab, Fab', F(ab)$_2$, or scFv fragment.

14. The method of claim 1 wherein the antibody or binding fragment thereof binds to the conformational epitope with a Kd≤1000 μM, a Kd≤500 nM, a Kd≤100 nM, a Kd≤50 nM, a Kd≤25 nM, a Kd≤10 nM, a Kd≤5 nM, a Kd≤1 nM, or a Kd≤0.1 nM.

15. The method of claim 1 wherein the inflammatory or thrombotic condition or disorder is related to at least one of vasoocclusive sickle cell pain crisis, tumor metastasis, thrombosis, atherosclerosis, allergic reactions, thyroiditis, psoriasis, dermatitis, nephritis, lupus erythematosis, scleroderma, sepsis, rhinitis, anaphylaxis, diabetes, multiple sclerosis, graft rejection, graft vs. host disease, asthma, chronic obstructive pulmonary disease, inflammatory bowel disease, arthritis, and ischemic reperfusion injury, type IV delayed hypersensitivity, systematic inflammatory response syndrome, or multiple organ failure.

16. The method of claim 15 wherein the ischemic reperfusion injury is caused by at least one of myocardial infarction, stroke, and organ transplantation.

17. The method of claim 1 wherein said antibody is administered to the subject parenterally, intramuscularly, intraperitoneally, epidurally, or orally, intravenously, subcutaneously, or in a nebulized form.

18. The method of claim 1 wherein said antibody or binding fragment is administered to the subject in an amount of 1 ng/kg to 100 mg/kg.

\* \* \* \* \*

SEQUENCE LISTING

<160> NUMBER OF SEQ ID NOS: 83

<210> SEQ ID NO 1
<211> LENGTH: 279
<212> TYPE: PRT
<213> ORGANISM: Homo sapiens

<400> SEQUENCE: 1

```
Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
    50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140
```

```
Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
            165                 170                 175

Gly Asn Phe Ser Phe Asn Ser Gln Cys Ser Phe His Cys Thr Asp Gly
        180                 185                 190

Tyr Gln Val Asn Gly Pro Ser Lys Leu Glu Cys Leu Ala Ser Gly Ile
    195                 200                 205

Trp Thr Asn Lys Pro Pro Gln Cys Leu Ala Ala Gln Cys Pro Pro Leu
210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
            275

<210> SEQ ID NO 2
<211> LENGTH: 282
<212> TYPE: PRT
<213> ORGANISM: Mus musculus

<400> SEQUENCE: 2

Trp Thr Tyr Asn Tyr Ser Thr Lys Ala Tyr Ser Trp Asn Asn Ser Arg
1               5                   10                  15

Val Phe Cys Arg Arg His Phe Thr Asp Leu Val Ala Ile Gln Asn Lys
            20                  25                  30

Asn Glu Ile Ala His Leu Asn Asp Val Ile Pro Phe Phe Asn Ser Tyr
        35                  40                  45

Tyr Trp Ile Gly Ile Arg Lys Ile Asn Asn Lys Trp Thr Trp Val Gly
    50                  55                  60

Thr Asn Lys Thr Leu Thr Glu Glu Ala Glu Asn Trp Ala Asp Asn Glu
65                  70                  75                  80

Pro Asn Asn Lys Lys Asn Asn Gln Asp Cys Val Glu Ile Tyr Ile Lys
                85                  90                  95

Ser Asn Ser Ala Pro Gly Lys Trp Asn Asp Glu Pro Cys Phe Lys Arg
            100                 105                 110

Lys Arg Ala Leu Cys Tyr Thr Ala Ser Cys Gln Asp Met Ser Cys Ser
        115                 120                 125

Asn Gln Gly Glu Cys Ile Glu Thr Ile Gly Ser Tyr Thr Cys Ser Cys
130                 135                 140

Tyr Pro Gly Phe Tyr Gly Pro Glu Cys Glu Tyr Val Lys Glu Cys Gly
145                 150                 155                 160

Lys Val Asn Ile Pro Gln His Val Leu Met Asn Cys Ser His Pro Leu
            165                 170                 175

Gly Glu Phe Ser Phe Asn Ser Gln Cys Thr Phe Ser Cys Ala Glu Gly
        180                 185                 190

Tyr Glu Leu Asp Gly Pro Gly Leu Gln Cys Leu Ala Ser Gly Ile
    195                 200                 205

Trp Thr Asn Asn Pro Pro Lys Cys Asp Ala Val Gln Cys Gln Ser Leu
210                 215                 220

Glu Ala Pro Pro His Gly Thr Met Ala Cys Met His Pro Ile Ala Ala
```

```
                225                 230                 235                 240

Phe Ala Tyr Asp Ser Ser Cys Lys Phe Glu Cys Gln Pro Gly Tyr Arg
                245                 250                 255

Ala Arg Gly Ser Asn Thr Leu His Cys Thr Gly Ser Gly Gln Trp Ser
                260                 265                 270

Glu Pro Leu Pro Thr Cys Glu Ala Ile Ala
                275                 280

<210> SEQ ID NO 3
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-1 (mouse P-selecin amino acids
      substituted into human P-selectin at positions 4, 14, 17, 18, 20,
      21, 22, 23)
<220> FEATURE:
<221> NAME/KEY: misc_feature
<222> LOCATION: (4)..(4)
<223> OTHER INFORMATION: His to Asn
<220> FEATURE:
<221> NAME/KEY: misc_feature
<222> LOCATION: (14)..(14)
<223> OTHER INFORMATION: Ile to Asn
<220> FEATURE:
<221> NAME/KEY: misc_feature
<222> LOCATION: (17)..(17)
<223> OTHER INFORMATION: Lys to Val
<220> FEATURE:
<221> NAME/KEY: misc_feature
<222> LOCATION: (18)..(18)
<223> OTHER INFORMATION: Tyr to Phe
<220> FEATURE:
<221> NAME/KEY: misc_feature
<222> LOCATION: (20)..(20)
<223> OTHER INFORMATION: Gln to Arg
<220> FEATURE:
<221> NAME/KEY: misc_feature
<222> LOCATION: (21)..(21)
<223> OTHER INFORMATION: Asn to Arg
<220> FEATURE:
<221> NAME/KEY: misc_feature
<222> LOCATION: (22)..(22)
<223> OTHER INFORMATION: Arg to His
<220> FEATURE:
<221> NAME/KEY: misc_feature
<222> LOCATION: (23)..(23)
<223> OTHER INFORMATION: Tyr to Phe

<400> SEQUENCE: 3

Trp Thr Tyr Asn Tyr Ser Thr Lys Ala Tyr Ser Trp Asn Asn Ser Arg
1               5                   10                  15

Val Phe Cys Arg Arg His Phe Thr Asp Leu Val Ala Ile Gln Asn Lys
                20                  25                  30

Asn Glu Ile Asp Tyr Leu Asn Lys Val Leu Pro Tyr Tyr Ser Ser Tyr
            35                  40                  45

Tyr Trp Ile Gly Ile Arg Lys Asn Asn Lys Thr Trp Thr Trp Val Gly
        50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110
```

```
Lys His Ala Leu Cys Tyr Thr Ala Ser Cys Gln Asp Met Ser Cys Ser
            115                 120                 125

Lys Gln Gly Glu Cys Leu Glu Thr Ile Gly Asn Tyr Thr Cys Ser Cys
        130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
        195                 200                 205

Trp Thr Asn Lys Pro Pro Gln Cys Leu Ala Ala Gln Cys Pro Pro Leu
210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
        275

<210> SEQ ID NO 4
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-2 (human P-selectin positions 1-35;
      mouse P-selectin thereafter)

<400> SEQUENCE: 4

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Ala His Leu Asn Asp Val Ile Pro Phe Phe Asn Ser Tyr
        35                  40                  45

Tyr Trp Ile Gly Ile Arg Lys Ile Asn Asn Lys Trp Thr Trp Val Gly
    50                  55                  60

Thr Asn Lys Thr Leu Thr Glu Glu Ala Glu Asn Trp Ala Asp Asn Glu
65                  70                  75                  80

Pro Asn Asn Lys Lys Asn Asn Gln Asp Cys Val Glu Ile Tyr Ile Lys
                85                  90                  95

Ser Asn Ser Ala Pro Gly Lys Trp Asn Asp Glu Pro Cys Phe Lys Arg
            100                 105                 110

Lys Arg Ala Leu Cys Tyr Thr Ala Ser Cys Gln Asp Met Ser Cys Ser
        115                 120                 125

Asn Gln Gly Glu Cys Ile Glu Thr Ile Gly Ser Tyr Thr Cys Ser Cys
    130                 135                 140

Tyr Pro Gly Phe Tyr Gly Pro Glu Cys Glu Tyr Val Lys Glu Cys Gly
145                 150                 155                 160

Lys Val Asn Ile Pro Gln His Val Leu Met Asn Cys Ser His Pro Leu
                165                 170                 175
```

```
Gly Glu Phe Ser Phe Asn Ser Gln Cys Thr Phe Ser Cys Ala Glu Gly
            180                 185                 190

Tyr Glu Leu Asp Gly Pro Gly Glu Leu Gln Cys Leu Ala Ser Gly Ile
            195                 200                 205

Trp Thr Asn Asn Pro Pro Lys Cys Asp Ala Val Gln Cys Gln Ser Leu
210                 215                 220

Glu Ala Pro Pro His Gly Thr Met Ala Cys Met His Pro Ile Ala Ala
225                 230                 235                 240

Phe Ala Tyr Asp Ser Ser Cys Lys Phe Glu Cys Gln Pro Gly Tyr Arg
            245                 250                 255

Ala Arg Gly Ser Asn Thr Leu His Cys Thr Gly Ser Gly Gln Trp Ser
            260                 265                 270

Glu Pro Leu Pro Thr Cys Glu Ala Ile Ala
            275                 280

<210> SEQ ID NO 5
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-3 (mouse P-selecin amino acids
      substituted into human P-selectin at positions 4, 14, 17, 18)
<220> FEATURE:
<221> NAME/KEY: misc_feature
<222> LOCATION: (4)..(4)
<223> OTHER INFORMATION: His to Asn
<220> FEATURE:
<221> NAME/KEY: misc_feature
<222> LOCATION: (14)..(14)
<223> OTHER INFORMATION: Ile to Asn
<220> FEATURE:
<221> NAME/KEY: misc_feature
<222> LOCATION: (17)..(17)
<223> OTHER INFORMATION: Lys to Val
<220> FEATURE:
<221> NAME/KEY: misc_feature
<222> LOCATION: (18)..(18)
<223> OTHER INFORMATION: Tyr to Phe

<400> SEQUENCE: 5

Trp Thr Tyr Asn Tyr Ser Thr Lys Ala Tyr Ser Trp Asn Asn Ser Arg
1               5                   10                  15

Val Phe Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140
```

```
Tyr Pro Gly Phe Tyr Gly Pro Glu Cys Glu Tyr Val Arg Glu Cys Gly
145                 150                 155                 160

Gl

```
                    115                 120                 125
Lys Gln Gly Glu Cys Leu Glu Thr Ile Gly Asn Tyr Thr Cys Ser Cys
        130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
        195                 200                 205

Trp Thr Asn Lys Pro Pro Gln Cys Leu Ala Ala Gln Cys Pro Pro Leu
    210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
        275
```

<210> SEQ ID NO 7
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-5 (single amino acid change in human
      P-selectin - human H4 to mouse N4)
<220> FEATURE:
<221> NAME/KEY: misc_feature
<222> LOCATION: (4)..(4)
<223> OTHER INFORMATION: His to Asn

<400> SEQUENCE: 7

```
Trp Thr Tyr Asn Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140

Tyr Pro Gly Phe Tyr Gly Pro Glu Cys Glu Tyr Val Arg Glu Cys Gly
145                 150                 155                 160
```

```
Glu Leu Glu Leu Pro Gln His Val Leu Met Asn Cys Ser His Pro Leu
            165                 170                 175

Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
            195                 200                 205

Trp Thr Asn Lys Pro Pro Gln Cys Leu Ala Ala Gln Cys Pro Pro Leu
            210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
            245                 250                 255

Leu Val Gly Pro Glu Val Val Gln Cys Thr Ala Ser Gly Val Trp Thr
            260                 265                 270

Ala Pro Ala Pro Val Cys Lys
            275

<210> SEQ ID NO 8
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-5Q (substitution of Q for H4 in human
      P-selectin - removes putative glycosylation site)
<220> FEATURE:
<221> NAME/KEY: misc_feature
<222> LOCATION: (4)..(4)
<223> OTHER INFORMATION: His to Gln

<400> SEQUENCE: 8

Trp Thr Tyr Gln Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
            35                  40                  45

Tyr Trp Ile Gly Ile Arg Lys Asn Asn Lys Thr Trp Thr Trp Val Gly
            50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
            85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
            115                 120                 125

Lys Gln Gly Glu Cys Leu Glu Thr Ile Gly Asn Tyr Thr Cys Ser Cys
            130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
            165                 170                 175

Gly Asn Phe Ser Phe Asn Ser Gln Cys Ser Phe His Cys Thr Asp Gly
            180                 185                 190
```

```
Tyr Gln Val Asn Gly Pro Ser Lys Leu Glu Cys Leu Ala Ser Gly Ile
            195                 200                 205

Trp Thr Asn Lys Pro Pro Gln Cys Leu Ala Ala Gln Cys Pro Pro Leu
    210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
            275

<210> SEQ ID NO 9
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-6 (human P-selectin positions 1-121;
      thereafter mouse P-selectin)

<400> SEQUENCE: 9

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
    50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Asn Gln Gly Glu Cys Ile Glu Thr Ile Gly Ser Tyr Thr Cys Ser Cys
    130                 135                 140

Tyr Pro Gly Phe Tyr Gly Pro Glu Cys Glu Tyr Val Lys Glu Cys Gly
145                 150                 155                 160

Lys Val Asn Ile Pro Gln His Val Leu Met Asn Cys Ser His Pro Leu
                165                 170                 175

Gly Glu Phe Ser Phe Asn Ser Gln Cys Thr Phe Ser Cys Ala Glu Gly
            180                 185                 190

Tyr Glu Leu Asp Gly Pro Gly Glu Leu Gln Cys Leu Ala Ser Gly Ile
        195                 200                 205

Trp Thr Asn Asn Pro Pro Lys Cys Asp Ala Val Gln Cys Gln Ser Leu
    210                 215                 220

Glu Ala Pro His Gly Thr Met Ala Cys Met His Pro Ile Ala Ala
225                 230                 235                 240

Phe Ala Tyr Asp Ser Ser Cys Lys Phe Glu Cys Gln Pro Gly Tyr Arg
                245                 250                 255
```

```
Ala Arg Gly Ser Asn Thr Leu His Cys Thr Gly Ser Gly Gln Trp Ser
            260                 265                 270

Glu Pro Leu Pro Thr Cys Glu Ala Ile Ala
        275                 280

<210> SEQ ID NO 10
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-7 (human P-selectin positions 1-177;
      thereafter mouse P-selectin)

<400> SEQUENCE: 10

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
    50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Glu Phe Ser Phe Asn Ser Gln Cys Thr Phe Ser Cys Ala Glu Gly
            180                 185                 190

Tyr Glu Leu Asp Gly Pro Gly Glu Leu Gln Cys Leu Ala Ser Gly Ile
        195                 200                 205

Trp Thr Asn Asn Pro Pro Lys Cys Asp Ala Val Gln Cys Gln Ser Leu
    210                 215                 220

Glu Ala Pro Pro His Gly Thr Met Ala Cys Met His Pro Ile Ala Ala
225                 230                 235                 240

Phe Ala Tyr Asp Ser Ser Cys Lys Phe Glu Cys Gln Pro Gly Tyr Arg
                245                 250                 255

Ala Arg Gly Ser Asn Thr Leu His Cys Thr Gly Ser Gly Gln Trp Ser
            260                 265                 270

Glu Pro Leu Pro Thr Cys Glu Ala Ile Ala
        275                 280

<210> SEQ ID NO 11
<211> LENGTH: 282
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera 7B (human P-selectin positions 1-156;
      thereafter mouse P-selectin)

<400> SEQUENCE: 11
```

| | | | | | | | | | | | | | | |
|---|---|---|---|---|---|---|---|---|---|---|---|---|---|---|
| Trp | Thr | Tyr | His | Tyr | Ser | Thr | Lys | Ala | Tyr | Ser | Trp | Asn | Ile | Ser | Arg |
| 1 | | | | 5 | | | | | 10 | | | | | 15 |
| Lys | Tyr | Cys | Gln | Asn | Arg | Tyr | Thr | Asp | Leu | Val | Ala | Ile | Gln | Asn | Lys |
| | | | 20 | | | | | 25 | | | | | 30 | |
| Asn | Glu | Ile | Asp | Tyr | Leu | Asn | Lys | Val | Leu | Pro | Tyr | Tyr | Ser | Ser | Tyr |
| | | 35 | | | | | 40 | | | | | 45 | | | |
| Tyr | Trp | Ile | Gly | Ile | Arg | Lys | Asn | Asn | Lys | Thr | Trp | Thr | Trp | Val | Gly |
| | 50 | | | | | 55 | | | | | 60 | | | | |
| Thr | Lys | Lys | Ala | Leu | Thr | Asn | Glu | Ala | Glu | Asn | Trp | Ala | Asp | Asn | Glu |
| 65 | | | | | 70 | | | | | 75 | | | | | 80 |
| Pro | Asn | Asn | Lys | Arg | Asn | Asn | Glu | Asp | Cys | Val | Glu | Ile | Tyr | Ile | Lys |
| | | | | 85 | | | | | 90 | | | | | 95 | |
| Ser | Pro | Ser | Ala | Pro | Gly | Lys | Trp | Asn | Asp | Glu | His | Cys | Leu | Lys | Lys |
| | | | 100 | | | | | 105 | | | | | 110 | | |
| Lys | His | Ala | Leu | Cys | Tyr | Thr | Ala | Ser | Cys | Gln | Asp | Met | Ser | Cys | Ser |
| | | 115 | | | | | 120 | | | | | 125 | | | |
| Lys | Gln | Gly | Glu | Cys | Leu | Glu | Thr | Ile | Gly | Asn | Tyr | Thr | Cys | Ser | Cys |
| 130 | | | | | 135 | | | | | 140 | | | | | |
| Tyr | Pro | Gly | Phe | Tyr | Gly | Pro | Glu | Cys | Glu | Tyr | Val | Lys | Glu | Cys | Gly |
| 145 | | | | | 150 | | | | | 155 | | | | | 160 |
| Lys | Val | Asn | Ile | Pro | Gln | His | Val | Leu | Met | Asn | Cys | Ser | His | Pro | Leu |
| | | | | 165 | | | | | 170 | | | | | 175 | |
| Gly | Glu | Phe | Ser | Phe | Asn | Ser | Gln | Cys | Thr | Phe | Ser | Cys | Ala | Glu | Gly |
| | | | 180 | | | | | 185 | | | | | 190 | | |
| Tyr | Glu | Leu | Asp | Gly | Pro | Gly | Glu | Leu | Gln | Cys | Leu | Ala | Ser | Gly | Ile |
| | | 195 | | | | | 200 | | | | | 205 | | | |
| Trp | Thr | Asn | Asn | Pro | Pro | Lys | Cys | Asp | Ala | Val | Gln | Cys | Gln | Ser | Leu |
| | 210 | | | | | 215 | | | | | 220 | | | | |
| Glu | Ala | Pro | Pro | His | Gly | Thr | Met | Ala | Cys | Met | His | Pro | Ile | Ala | Ala |
| 225 | | | | | 230 | | | | | 235 | | | | | 240 |
| Phe | Ala | Tyr | Asp | Ser | Ser | Cys | Lys | Phe | Glu | Cys | Gln | Pro | Gly | Tyr | Arg |
| | | | 245 | | | | | 250 | | | | | 255 | | |
| Ala | Arg | Gly | Ser | Asn | Thr | Leu | His | Cys | Thr | Gly | Ser | Gly | Gln | Trp | Ser |
| | | 260 | | | | | 265 | | | | | 270 | | | |
| Glu | Pro | Leu | Pro | Thr | Cys | Glu | Ala | Ile | Ala | | | | | | |
| | | 275 | | | | | 280 | | | | | | | | |

```
<210> SEQ ID NO 12
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-8 (single substitution in human
      P-selectin - human I14 to mouse N14)
<220> FEATURE:
<221> NAME/KEY: misc_feature
<222> LOCATION: (14)..(14)
<223> OTHER INFORMATION: Ile to Asn
```

-continued

<400> SEQUENCE: 12

```
Trp Thr Tyr Asn Tyr Ser Thr Lys Ala Tyr Ser Trp Asn Asn Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
    50                  55                  60

Thr Lys Lys Ala Leu Thr Asn Glu Ala Glu Asn Trp Ala Asp Asn Glu
65              70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
        195                 200                 205

Trp Thr Asn Lys Pro Pro Gln Cys Leu Ala Ala Gln Cys Pro Pro Leu
    210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
        275
```

<210> SEQ ID NO 13
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-9 (single substitution in human
      P-selectin - human K17 to mouse V17)
<220> FEATURE:
<221> NAME/KEY: misc_feature
<222> LOCATION: (17)..(17)
<223> OTHER INFORMATION: Lys to Val

<400> SEQUENCE: 13

```
Trp Thr Tyr His Tyr Ser Thr Lys Ala Tyr Ser Trp Asn Ile Ser Arg
1               5                   10                  15

Val Tyr Cys Gln Asn Arg Tyr Thr Asp Leu Val Ala Ile Gln Asn Lys
```

```
                20                  25                  30

Asn Glu Ile Asp Tyr Leu Asn Lys Val Leu Pro Tyr Tyr Ser Ser Tyr
            35                  40                  45

Tyr Trp Ile Gly Ile Arg Lys Asn Asn Lys Thr Trp Thr Trp Val Gly
        50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
        195                 200                 205

Trp Thr Asn Lys Pro Pro Gln Cys Leu Ala Ala Gln Cys Pro Pro Leu
    210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
        275

<210> SEQ ID NO 14
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-10 (single substitution in human
      P-selectin - human Y18 to mouse F18)
<220> FEATURE:
<221> NAME/KEY: misc_feature
<222> LOCATION: (18)..(18)
<223> OTHER INFORMATION: Tyr to Phe

<400> SEQUENCE: 14

Trp Thr Tyr His Tyr Ser Thr Lys Ala Tyr Ser Trp Asn Ile Ser Arg
1               5                   10                  15

Lys Phe Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
    50                  55                  60
```

```
Thr Lys Lys Ala Leu Thr Asn Glu Ala Glu Asn Trp Ala Asp Asn Glu
 65                  70                  75                  80

Pro Asn Asn Lys Arg Asn Asn Glu Asp Cys Val Glu Ile Tyr Ile Lys
                 85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
            115                 120                 125

Lys Gln Gly Glu Cys Leu Glu Thr Ile Gly Asn Tyr Thr Cys Ser Cys
130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
            195                 200                 205

Trp Thr Asn Lys Pro Pro Gln Cys Leu Ala Ala Gln Cys Pro Pro Leu
210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
            275

<210> SEQ ID NO 15
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-11 (single substitution in human
      P-selectin - human Q20 to mouse R20)
<220> FEATURE:
<221> NAME/KEY: misc_feature
<222> LOCATION: (20)..(20)
<223> OTHER INFORMATION: Gln to Arg

<400> SEQUENCE: 15

Trp Thr Tyr His Tyr Ser Thr Lys Ala Tyr Ser Trp Asn Ile Ser Arg
  1               5                  10                  15

Lys Tyr Cys Arg Asn Arg Tyr Thr Asp Leu Val Ala Ile Gln Asn Lys
                 20                  25                  30

Asn Glu Ile Asp Tyr Leu Asn Lys Val Leu Pro Tyr Tyr Ser Ser Tyr
             35                  40                  45

Tyr Trp Ile Gly Ile Arg Lys Asn Asn Lys Thr Trp Thr Trp Val Gly
 50                  55                  60

Thr Lys Lys Ala Leu Thr Asn Glu Ala Glu Asn Trp Ala Asp Asn Glu
 65                  70                  75                  80

Pro Asn Asn Lys Arg Asn Asn Glu Asp Cys Val Glu Ile Tyr Ile Lys
                 85                  90                  95
```

```
Ser Pro Ser Ala Pro Gly Lys Trp Asn Asp Glu His Cys Leu Lys Lys
            100                 105                 110

Lys His Ala Leu Cys T

```
            130                 135                 140
Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
        195                 200                 205

Trp Thr Asn Lys Pro Pro Gln Cys Leu Ala Ala Gln Cys Pro Pro Leu
    210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
        275

<210> SEQ ID NO 17
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-13 (single substitution in human
      P-selectin - human R22 to mouse H22)
<220> FEATURE:
<221> NAME/KEY: misc_feature
<222> LOCATION: (22)..(22)
<223> OTHER INFORMATION: Arg to His

<400> SEQUENCE: 17

Trp Thr Tyr His Tyr Ser Thr Lys Ala Tyr Ser Trp Asn Ile Ser Arg
1               5                   10                  15

Lys Tyr Cys Gln Asn His Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
    50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175
```

```
Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
        195                 200                 205

Trp Thr Asn Lys Pro Pro Gln Cys Leu Ala Ala Gln Cys Pro Pro Leu
    210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
            275
```

<210> SEQ ID NO 18
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-14 (single substitution in human
      P-selectin - human Y23 to mouse F23)
<220> FEATURE:
<221> NAME/KEY: misc_feature
<222> LOCATION: (23)..(23)
<223> OTHER INFORMATION: Tyr to Phe

<400> SEQUENCE: 18

```
Trp Thr Tyr His Tyr Ser Thr Lys Ala Tyr Ser Trp Asn Ile Ser Arg
1               5                   10                  15

Lys Tyr Cys Gln Asn Arg Phe Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
    50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
        195                 200                 205
```

```
Trp Thr Asn Lys Pro Pro Gln Cys Leu Ala Ala Gln Cys Pro Pro Leu
210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
                260                 265                 270

Ala Pro Ala Pro Val Cys Lys
        275

<210> SEQ ID NO 19
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-15 (human P-selectin positions 1-97;
      thereafter mouse P-selectin)

<400> SEQUENCE: 19

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Asn Ser Ala Pro Gly Lys Trp Asn Asp Glu Pro Cys Phe Lys Arg
            100                 105                 110

Lys Arg Ala Leu Cys Tyr Thr Ala Ser Cys Gln Asp Met Ser Cys Ser
        115                 120                 125

Asn Gln Gly Glu Cys Ile Glu Thr Ile Gly Ser Tyr Thr Cys Ser Cys
    130                 135                 140

Tyr Pro Gly Phe Tyr Gly Pro Glu Cys Glu Tyr Val Lys Glu Cys Gly
145                 150                 155                 160

Lys Val Asn Ile Pro Gln His Val Leu Met Asn Cys Ser His Pro Leu
                165                 170                 175

Gly Glu Phe Ser Phe Asn Ser Gln Cys Thr Phe Ser Cys Ala Glu Gly
            180                 185                 190

Tyr Glu Leu Asp Gly Pro Gly Glu Leu Gln Cys Leu Ala Ser Gly Ile
        195                 200                 205

Trp Thr Asn Asn Pro Pro Lys Cys Asp Ala Val Gln Cys Gln Ser Leu
210                 215                 220

Glu Ala Pro Pro His Gly Thr Met Ala Cys Met His Pro Ile Ala Ala
225                 230                 235                 240

Phe Ala Tyr Asp Ser Ser Cys Lys Phe Glu Cys Gln Pro Gly Tyr Arg
                245                 250                 255

Ala Arg Gly Ser Asn Thr Leu His Cys Thr Gly Ser Gly Gln Trp Ser
            260                 265                 270
```

Glu Pro Leu Pro Thr Cys Glu Ala Ile Ala
        275                 280

<210> SEQ ID NO 20
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-16 (human P-selectin amino acids
      substituted into mouse P-selectin at positions 4, 14, 17, 21, 22)
<220> FEATURE:
<221> NAME/KEY: misc_feature
<222> LOCATION: (4)..(4)
<223> OTHER INFORMATION: Asn to His
<220> FEATURE:
<221> NAME/KEY: misc_feature
<222> LOCATION: (14)..(14)
<223> OTHER INFORMATION: Asn to Ile
<220> FEATURE:
<221> NAME/KEY: misc_feature
<222> LOCATION: (17)..(17)
<223> OTHER INFORMATION: Val to Lys
<220> FEATURE:
<221> NAME/KEY: misc_feature
<222> LOCATION: (21)..(21)
<223> OTHER INFORMATION: Arg to Asn
<220> FEATURE:
<221> NAME/KEY: misc_feature
<222> LOCATION: (22)..(22)
<223> OTHER INFORMATION: His to Arg

<400> SEQUENCE: 20

Trp Thr Tyr His Tyr Ser Thr Lys Ala Tyr Ser Trp Asn Ile Ser Arg
1               5                   10                  15

Lys Phe Cys Arg Asn Arg Phe Thr Asp Leu Val Ala Ile Gln Asn Lys
            20                  25                  30

Asn Glu Ile Ala His Leu Asn Asp Val Ile Pro Phe Phe Asn Ser Tyr
        35                  40                  45

Tyr Trp Ile Gly Ile Arg Lys Ile Asn Asn Lys Trp Thr Trp Val Gly
    50                  55                  60

Thr Asn Lys Thr Leu Thr Glu Glu Ala Glu Asn Trp Ala Asp Asn Glu
65                  70                  75                  80

Pro Asn Asn Lys Lys Asn Gln Asp Cys Val Glu Ile Tyr Ile Lys
                85                  90                  95

Ser Asn Ser Ala Pro Gly Lys Trp Asn Asp Glu Pro Cys Phe Lys Arg
            100                 105                 110

Lys Arg Ala Leu Cys Tyr Thr Ala Ser Cys Gln Asp Met Ser Cys Ser
        115                 120                 125

Asn Gln Gly Glu Cys Ile Glu Thr Ile Gly Ser Tyr Thr Cys Ser Cys
    130                 135                 140

Tyr Pro Gly Phe Tyr Gly Pro Glu Cys Glu Tyr Val Lys Glu Cys Gly
145                 150                 155                 160

Lys Val Asn Ile Pro Gln His Val Leu Met Asn Cys Ser His Pro Leu
                165                 170                 175

Gly Glu Phe Ser Phe Asn Ser Gln Cys Thr Phe Ser Cys Ala Glu Gly
            180                 185                 190

Tyr Glu Leu Asp Gly Pro Gly Glu Leu Gln Cys Leu Ala Ser Gly Ile
        195                 200                 205

Trp Thr Asn Asn Pro Pro Lys Cys Asp Ala Val Gln Cys Gln Ser Leu
    210                 215                 220

Glu Ala Pro Pro His Gly Thr Met Ala Cys Met His Pro Ile Ala Ala
225                 230                 235                 240

Phe Ala Tyr Asp Ser Ser Cys Lys Phe Glu Cys Gln Pro Gly Tyr Arg
                245                 250                 255

Ala Arg Gly Ser Asn Thr Leu His Cys Thr Gly Ser Gly Gln Trp Ser
                260                 265                 270

Glu Pro Leu Pro Thr Cys Glu Ala Ile Ala
            275                 280

<210> SEQ ID NO 21
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-17 (human P-selectin positions 1-35,
      and 43-154; mouse P-selectin positions 36-42, and 155-282)

<400> SEQUENCE: 21

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
                20                  25                  30

Asn Glu Ile Ala His Leu Asn Asp Val Ile Pro Tyr Tyr Ser Ser Tyr
                35                  40                  45

Tyr Trp Ile Gly Ile Arg Lys Asn Asn Lys Thr Trp Thr Trp Val Gly
50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
                100                 105                 110

Lys His Ala Leu Cys Tyr Thr Ala Ser Cys Gln Asp Met Ser Cys Ser
                115                 120                 125

Lys Gln Gly Glu Cys Leu Glu Thr Ile Gly Asn Tyr Thr Cys Ser Cys
130                 135                 140

Tyr Pro Gly Phe Tyr Gly Pro Glu Cys Glu Tyr Val Lys Glu Cys Gly
145                 150                 155                 160

Lys Val Asn Ile Pro Gln His Val Leu Met Asn Cys Ser His Pro Leu
                165                 170                 175

Gly Glu Phe Ser Phe Asn Ser Gln Cys Thr Phe Ser Cys Ala Glu Gly
                180                 185                 190

Tyr Glu Leu Asp Gly Pro Gly Glu Leu Gln Cys Leu Ala Ser Gly Ile
                195                 200                 205

Trp Thr Asn Asn Pro Pro Lys Cys Asp Ala Val Gln Cys Gln Ser Leu
                210                 215                 220

Glu Ala Pro Pro His Gly Thr Met Ala Cys Met His Pro Ile Ala Ala
225                 230                 235                 240

Phe Ala Tyr Asp Ser Ser Cys Lys Phe Glu Cys Gln Pro Gly Tyr Arg
                245                 250                 255

Ala Arg Gly Ser Asn Thr Leu His Cys Thr Gly Ser Gly Gln Trp Ser
                260                 265                 270

Glu Pro Leu Pro Thr Cys Glu Ala Ile Ala
            275                 280

275             280

<210> SEQ ID NO 22
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-17B (human P-selectin positions 1-35
      and 43-279; mouse P-selectin positions 36-42)

<400> SEQUENCE: 22

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Ala His Leu Asn Asp Val Ile Pro Tyr Tyr Ser Ser Tyr
        35                  40                  45

Tyr Trp Ile Gly Ile Arg Lys Asn Asn Lys Thr Trp Thr Trp Val Gly
    50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
        195                 200                 205

Trp Thr Asn Lys Pro Pro Gln Cys Leu Ala Ala Gln Cys Pro Pro Leu
    210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
        275

<210> SEQ ID NO 23
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: Chimera-18 (human P-selectin positions C (C1,
C2, C3) and mouse CR1, CR2 substituted with mouse P-selectin C
(C1, C2, C3), CR1 and CR2)

<400> SEQUENCE: 23

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Phe Phe Asn Ser Tyr
        35                  40                  45

Tyr Trp Ile Gly Ile Arg Lys Asn Asn Lys Thr Trp Thr Trp Val Gly
    50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Asn Ser Ala Pro Gly Lys Trp Asn Asp Glu His Cys Leu Lys Lys
            100                 105                 110

Lys Arg Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140

Tyr Pro Gly Phe Tyr Gly Pro Glu Cys Glu Tyr Val Lys Glu Cys Gly
145                 150                 155                 160

Lys Val Asn Ile Pro Gln His Val Leu Met Asn Cys Ser His Pro Leu
                165                 170                 175

Gly Glu Phe Ser Phe Asn Ser Gln Cys Thr Phe Ser Cys Ala Glu Gly
            180                 185                 190

Tyr Glu Leu Asp Gly Pro Gly Glu Leu Gln Cys Leu Ala Ser Gly Ile
        195                 200                 205

Trp Thr Asn Asn Pro Pro Lys Cys Asp Ala Val Gln Cys Gln Ser Leu
    210                 215                 220

Glu Ala Pro Pro His Gly Thr Met Ala Cys Met His Pro Ile Ala Ala
225                 230                 235                 240

Phe Ala Tyr Asp Ser Ser Cys Lys Phe Glu Cys Gln Pro Gly Tyr Arg
                245                 250                 255

Ala Arg Gly Ser Asn Thr Leu His Cys Thr Gly Ser Gly Gln Trp Ser
            260                 265                 270

Glu Pro Leu Pro Thr Cys Glu Ala Ile Ala
        275                 280

<210> SEQ ID NO 24
<211> LENGTH: 279
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Chimera-18B (human P-selectin positions C (C1,
C2, C3 substituted with mouse P-selectin positions C (C1, C2, C3))

<400> SEQUENCE: 24

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Phe Phe Asn Ser Tyr
            35                  40                  45

Tyr Trp Ile Gly Ile Arg Lys Asn Asn Lys Thr Trp Thr Trp Val Gly
     50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Asn Ser Ala Pro Gly Lys Trp Asn Asp Glu His Cys Leu Lys Lys
                100                 105                 110

Lys Arg Ala Leu Cys Tyr Thr Ala Ser Cys Gln Asp Met Ser Cys Ser
                115                 120                 125

Lys Gln Gly Glu Cys Leu Glu Thr Ile Gly Asn Tyr Thr Cys Ser Cys
            130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Asn Phe Ser Phe Asn Ser Gln Cys Ser Phe His Cys Thr Asp Gly
                180                 185                 190

Tyr Gln Val Asn Gly Pro Ser Lys Leu Glu Cys Leu Ala Ser Gly Ile
            195                 200                 205

Trp Thr Asn Lys Pro Pro Gln Cys Leu Ala Ala Gln Cys Pro Pro Leu
    210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
            275

<210> SEQ ID NO 25
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-19 (human P-selectin positions Cluster
      D, CR1, CR2 substituted with mouse P-selectin D, CR1 and CR2)

<400> SEQUENCE: 25

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
                20                  25                  30

Asn Glu Ile Asp Tyr Leu Asn Lys Val Leu Pro Tyr Tyr Ser Ser Tyr
            35                  40                  45

Tyr Trp Ile Gly Ile Arg Lys Ile Asn Asn Lys Trp Thr Trp Val Gly
     50                  55                  60

Thr Asn Lys Thr Leu Thr Glu Glu Ala Glu Asn Trp Ala Asp Asn Glu
65                  70                  75                  80

Pro Asn Asn Lys Arg Asn Asn Glu Asp Cys Val Glu Ile Tyr Ile Lys

```
                85                  90                  95
Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140

Tyr Pro Gly Phe Tyr Gly Pro Glu Cys Glu Tyr Val Lys Glu Cys Gly
145                 150                 155                 160

Lys Val Asn Ile Pro Gln His Val Leu Met Asn Cys Ser His Pro Leu
                165                 170                 175

Gly Glu Phe Ser Phe Asn Ser Gln Cys Thr Phe Ser Cys Ala Glu Gly
            180                 185                 190

Tyr Glu Leu Asp Gly Pro Gly Glu Leu Gln Cys Leu Ala Ser Gly Ile
        195                 200                 205

Trp Thr Asn Asn Pro Pro Lys Cys Asp Ala Val Gln Cys Gln Ser Leu
    210                 215                 220

Glu Ala Pro Pro His Gly Thr Met Ala Cys Met His Pro Ile Ala Ala
225                 230                 235                 240

Phe Ala Tyr Asp Ser Ser Cys Lys Phe Glu Cys Gln Pro Gly Tyr Arg
                245                 250                 255

Ala Arg Gly Ser Asn Thr Leu His Cys Thr Gly Ser Gly Gln Trp Ser
            260                 265                 270

Glu Pro Leu Pro Thr Cys Glu Ala Ile Ala
        275                 280

<210> SEQ ID NO 26
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-19B (human P-selectin positions Cluster
      D substituted with mouse P-selectin Cluster D)

<400> SEQUENCE: 26

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Ile Asn Asn Lys Trp Thr Trp Val Gly
    50                  55                  60

Thr Asn Lys Thr Leu Thr Glu Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140
```

```
Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
            165                 170                 175

Gly Asn Phe Ser Phe Asn Ser Gln Cys Ser Phe His Cys Thr Asp Gly
        180                 185                 190

Tyr Gln Val Asn Gly Pro Ser Lys Leu Glu Cys Leu Ala Ser Gly Ile
    195                 200                 205

Trp Thr Asn Lys Pro Pro Gln Cys Leu Ala Ala Gln Cys Pro Pro Leu
    210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
            245                 250                 255

Leu Val Gly Pro Glu Val Val Gln Cys Thr Ala Ser Gly Val Trp Thr
        260                 265                 270

Ala Pro Ala Pro Val Cys Lys
        275

<210> SEQ ID NO 27
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-20 (human P-selectin positions E, CR1
      and CR2 substituted with mouse P-selectin Cluster E, CR1 and CR2)

<400> SEQUENCE: 27

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
    50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu Pro Cys Phe Lys Arg
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140

Tyr Pro Gly Phe Tyr Gly Pro Glu Cys Glu Tyr Val Lys Glu Cys Gly
145                 150                 155                 160

Lys Val Asn Ile Pro Gln His Val Leu Met Asn Cys Ser His Pro Leu
            165                 170                 175

Gly Glu Phe Ser Phe Asn Ser Gln Cys Thr Phe Ser Cys Ala Glu Gly
        180                 185                 190

Tyr Glu Leu Asp Gly Pro Gly Glu Leu Gln Cys Leu Ala Ser Gly Ile
    195                 200                 205
```

Trp Thr Asn Asn Pro Pro Lys Cys Asp Ala Val Gln Cys Gln Ser Leu
            210                 215                 220

Glu Ala Pro Pro His Gly Thr Met Ala Cys Met His Pro Ile Ala Ala
225                 230                 235                 240

Phe Ala Tyr Asp Ser Ser Cys Lys Phe Glu Cys Gln Pro Gly Tyr Arg
                245                 250                 255

Ala Arg Gly Ser Asn Thr Leu His Cys Thr Gly Ser Gly Gln Trp Ser
            260                 265                 270

Glu Pro Leu Pro Thr Cys Glu Ala Ile Ala
        275                 280

<210> SEQ ID NO 28
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-20B (human P-selectin positions E
      substituted with mouse P-selectin Cluster E)

<400> SEQUENCE: 28

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
    50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu Pro Cys Phe Lys Arg
            100                 105                 110

Lys His Ala Leu Cys Tyr Thr Ala Ser Cys Gln Asp Met Ser Cys Ser
        115                 120                 125

Lys Gln Gly Glu Cys Leu Glu Thr Ile Gly Asn Tyr Thr Cys Ser Cys
    130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
        195                 200                 205

Trp Thr Asn Lys Pro Pro Gln Cys Leu Ala Ala Gln Cys Pro Pro Leu
    210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr

Ala Pro Ala Pro Val Cys Lys
        275

<210> SEQ ID NO 29
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimera-21 (human P-selectin positions Cluster
      F substituted with mouse P-selectin Cluster F)

<400> SEQUENCE: 29

Trp Thr Tyr His Tyr Ser Thr Lys Ala Tyr Ser Trp Asn Ile Ser Arg
1               5                   10                  15

Lys Tyr Cys Gln Asn Arg Tyr Thr Asp Leu Val Ala Ile Gln Asn Lys
            20                  25                  30

Asn Glu Ile Asp Tyr Leu Asn Lys Val Leu Pro Tyr Tyr Ser Ser Tyr
        35                  40                  45

Tyr Trp Ile Gly Ile Arg Lys Asn Asn Lys Thr Trp Thr Trp Val Gly
    50                  55                  60

Thr Lys Lys Ala Leu Thr Asn Glu Ala Glu Asn Trp Ala Asp Asn Glu
65                  70                  75                  80

Pro Asn Asn Lys Arg Asn Asn Glu Asp Cys Val Glu Ile Tyr Ile Lys
                85                  90                  95

Ser Pro Ser Ala Pro Gly Lys Trp Asn Asp Glu His Cys Leu Lys Lys
            100                 105                 110

Lys His Ala Leu Cys Tyr Thr Ala Ser Cys Gln Asp Met Ser Cys Ser
        115                 120                 125

Asn Gln Gly Glu Cys Ile Glu Thr Ile Gly Ser Tyr Thr Cys Ser Cys
    130                 135                 140

Tyr Pro Gly Phe Tyr Gly Pro Glu Cys Glu Tyr Val Arg Glu Cys Gly
145                 150                 155                 160

Glu Leu Glu Leu Pro Gln His Val Leu Met Asn Cys Ser His Pro Leu
                165                 170                 175

Gly Asn Phe Ser Phe Asn Ser Gln Cys Ser Phe His Cys Thr Asp Gly
            180                 185                 190

Tyr Gln Val Asn Gly Pro Ser Lys Leu Glu Cys Leu Ala Ser Gly Ile
        195                 200                 205

Trp Thr Asn Lys Pro Pro Gln Cys Leu Ala Ala Gln Cys Pro Pro Leu
    210                 215                 220

Lys Ile Pro Glu Arg Gly Asn Met Thr Cys Leu His Ser Ala Lys Ala
225                 230                 235                 240

Phe Gln His Gln Ser Ser Cys Ser Phe Ser Cys Glu Glu Gly Phe Ala
                245                 250                 255

Leu Val Gly Pro Glu Val Val Gln Cys Thr Ala Ser Gly Val Trp Thr
            260                 265                 270

Ala Pro Ala Pro Val Cys Lys
        275

<210> SEQ ID NO 30
<211> LENGTH: 5
<212> TYPE: PRT
<213> ORGANISM: Unknown
<220> FEATURE:

```
<223> OTHER INFORMATION: Description of Unknown: Enterokinase protease
      cleavage site peptide

<400> SEQUENCE: 30

Asp Asp Asp Asp Lys
1               5

<210> SEQ ID NO 31
<211> LENGTH: 6
<212> TYPE: PRT
<213> ORGANISM: Unknown
<220> FEATURE:
<223> OTHER INFORMATION: Description of Unknown: Thrombin protease
      cleavage site peptide

<400> SEQUENCE: 31

Leu Val Pro Arg Gly Ser
1               5

<210> SEQ ID NO 32
<211> LENGTH: 4
<212> TYPE: PRT
<213> ORGANISM: Unknown
<220> FEATURE:
<223> OTHER INFORMATION: Description of Unknown: Factor Xa protease
      cleavage site peptide

<400> SEQUENCE: 32

Ile Glu Gly Arg
1

<210> SEQ ID NO 33
<211> LENGTH: 7
<212> TYPE: PRT
<213> ORGANISM: Mus sp.

<400> SEQUENCE: 33

Ala Ala Ser Asn Leu Glu Ser
1               5

<210> SEQ ID NO 34
<211> LENGTH: 9
<212> TYPE: PRT
<213> ORGANISM: Mus sp.

<400> SEQUENCE: 34

Gln Gln Ser Asp Glu Asn Pro Leu Thr
1               5

<210> SEQ ID NO 35
<211> LENGTH: 5
<212> TYPE: PRT
<213> ORGANISM: Mus sp.

<400> SEQUENCE: 35

Ser Tyr Asp Ile Asn
1               5

<210> SEQ ID NO 36
<211> LENGTH: 17
<212> TYPE: PRT
<213> ORGANISM: Mus sp.

<400> SEQUENCE: 36

Trp Ile Tyr Pro Gly Asp Gly Ser Ile Lys Tyr Asn Glu Lys Phe Lys
1               5                   10                  15
```

Gly

<210> SEQ ID NO 37
<211> LENGTH: 13
<212> TYPE: PRT
<213> ORGANISM: Mus sp.

<400> SEQUENCE: 37

Arg Gly Glu Tyr Gly Asn Tyr Glu Gly Ala Met Asp Tyr
1               5                   10

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly His Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asn Pro Leu Thr Phe Gly Thr Gly Thr Lys Leu Glu Leu Lys
            100                 105                 110

<210> SEQ ID NO 39
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

```
<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly His Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asp
                85                  90                  95

Glu Asn Pro Leu Thr Phe Gly Gly Gly Thr Lys Val Glu Ile Lys
            100                 105                 110

<210> SEQ ID NO 41
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly His Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Ile Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asp
                85                  90                  95

Glu Asn Pro Leu Thr Phe Gly Gly Gly Thr Lys Val Glu Ile Lys
            100                 105                 110

<210> SEQ ID NO 42
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Ser Tyr
            20                  25                  30
```

Asp Ile Asn Trp Val Lys Gln Arg Pro Gly Gln Gly Leu Glu Trp Ile
            35                  40                  45

Gly Trp Ile Tyr Pro Gly Asp Gly Ser Ile Lys Tyr Asn Glu Lys Phe
        50                  55                  60

Lys Gly Lys Ala Thr Leu Thr Val Asp Lys Ser Ser Ser Thr Ala Tyr
 65                  70                  75                  80

Met Gln Val Ser Ser Leu Thr Ser Glu Asn Ser Ala Val Tyr Phe Cys
                85                  90                  95

Ala Arg Arg Gly Glu Tyr Gly Asn Tyr Glu Gly Ala Met Asp Tyr Trp
                100                 105                 110

Gly Gln Gly Thr Ile Val Thr Val Ser Ser
            115                 120

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Val Gly Arg Cys Ser Ser Thr Ser Cys Asp Tyr Trp Gly
                100                 105                 110

Gln Gly Thr Leu Val Thr Val Ser Ser
            115                 120

<210> SEQ ID NO 44
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30

Asp Ile Asn Trp Val Arg Gln Ala Pro Gly Lys Gly Leu Glu Trp Met
        35                  40                  45

Gly Trp Ile Tyr Pro Gly Asp Gly Ser Ile Lys Tyr Asn Glu Lys Phe
    50                  55                  60

Lys Gly Arg Val Thr Met Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Gly Glu Tyr Gly Asn Tyr Glu Gly Ala Met Asp Tyr Trp
            100                 105                 110

Gly Gln Gly Thr Leu Val Thr Val Ser Ser
        115                 120

<210> SEQ ID NO 45
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30

Asp Ile Asn Trp Val Arg Gln Ala Pro Gly Lys Gly Leu Glu Trp Ile
            35                  40                  45

Gly Trp Ile Tyr Pro Gly Asp Gly Ser Ile Lys Tyr Asn Glu Lys Phe
        50                  55                  60

Lys Gly Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Gly Glu Tyr Gly Asn Tyr Glu Gly Ala Met Asp Tyr Trp
            100                 105                 110

Gly Gln Gly Thr Leu Val Thr Val Ser Ser
        115                 120

<210> SEQ ID NO 46
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gacattgtgc taacccaatc tccagcttct ttggctgtgt ctctagggca gagggccacc      60
atctcctgca aggccagcca agtgttgat tatgatggtc atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtgatga aaatcccctc     300
acgttcggta ctgggaccaa gctggagctg aaacgg                               336

<210> SEQ ID NO 47
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly His Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asn Pro Leu Thr Phe Gly Thr Gly Thr Lys Leu Glu Leu Lys Arg
            100                 105                 110
```

<210> SEQ ID NO 48
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
gacattgtgc tgacccaatc tccagcttct ttggctgtgt ctctagggca gagggccacc    60
atctcctgca aggccagcca agtgttgat tatgatggtc atagttatat gaactggtac   120
caacagaaac caggacagcc acccaaactc ctcatctatg ctgcatccaa tctagaatct   180
gggatcccag ccaggtttag tggcagtggg tctgggacag acttcaccct caacatccat   240
cctgtggagg aggaggatgc tgcaacctat tactgtcagc aaagtgatga aaatccctc   300
acgttcggta ctgggaccaa gctggagctg aaacgg                             336
```

<210> SEQ ID NO 49
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly His Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asn Pro Leu Thr Phe Gly Thr Gly Thr Lys Leu Glu Leu Lys Arg
            100                 105                 110
```

<210> SEQ ID NO 50
<211> LENGTH: 336

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
gacatccaga tgacacagtc tccagcttct ttggctgtgt ctctagggca gagggccacc      60
atctcctgca aggccagcca aagtgttgat tatgatggtc atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtgatga aaatccctc      300 acgttcggta ctgggaccaa gctggagctg aaacgg                               336

<210> SEQ ID NO 51
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Gln Met Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly His Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asn Pro Leu Thr Phe Gly Thr Gly Thr Lys Leu Glu Leu Lys Arg
            100                 105                 110

<210> SEQ ID NO 52
<211> LENGTH: 331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gacattgtgc tgacccagtc tccagcttct ttggctgtgt ctctagggca gagggccacc      60
atctcctgca aggccagcca aagtgttgat tatgatggtc atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtgatga aaatccctc      300 acgttcggta ctgggaccaa gctggagctg a                                    331

<210> SEQ ID NO 53
<211> LENGTH: 110
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 53

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly His Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asn Pro Leu Thr Phe Gly Thr Gly Thr Lys Leu Glu Leu
            100                 105                 110
```

<210> SEQ ID NO 54
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
gacattgtgc taacccagtc tccagcttct ttggctgtgt ctctagggca gagggccacc      60
atctcctgca aggccagcca agtgttgat tatgatggtc atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtgatga aaatcccctc     300
acgttcggta ctgggaccaa gctggagctg aaacgg                              336
```

<210> SEQ ID NO 55
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly His Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95
```

```
Glu Asn Pro Leu Thr Phe Gly Thr Gly Thr Lys Leu Glu Leu Lys Arg
            100                 105                 110
```

<210> SEQ ID NO 56
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
aggtgaagct gcagcagtca ggacctgagc tggtgaagcc tggggcttta gtgaagatat    60
cctgcaaggc ttctggttac accttcacaa gctacgatat aaattgggtg aagcagaggc   120
ctggacaggg acttgagtgg attggatgga tttatcctgg agatggtagt attaagtaca   180
atgagaaatt caagggcaag gccacactga ctgtagacaa atcctccagc acagcctaca   240
tgcaggtcag cagcctgact tctgagaatt ctgcagtcta tttctgtgca agacgggggg   300
agtatggtaa ctacgagggg gctatggact actggggcca aggaccacg gtcaccgtct    360 cctca                                                               365
```

<210> SEQ ID NO 57
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Val Lys Leu Gln Gln Ser Gly Pro Glu Leu Val Lys Pro Gly Ala Leu
1               5                   10                  15

Val Lys Ile Ser Cys Lys Ala Ser Gly Tyr Thr Phe Thr Ser Tyr Asp
            20                  25                  30

Ile Asn Trp Val Lys Gln Arg Pro Gly Gln Gly Leu Glu Trp Ile Gly
        35                  40                  45

Trp Ile Tyr Pro Gly Asp Gly Ser Ile Lys Tyr Asn Glu Lys Phe Lys
    50                  55                  60

Gly Lys Ala Thr Leu Thr Val Asp Lys Ser Ser Ser Thr Ala Tyr Met
65                  70                  75                  80

Gln Val Ser Ser Leu Thr Ser Glu Asn Ser Ala Val Tyr Phe Cys Ala
                85                  90                  95

Arg Arg Gly Glu Tyr Gly Asn Tyr Glu Gly Ala Met Asp Tyr Trp Gly
            100                 105                 110

Gln Gly Thr Thr Val Thr Val Ser Ser
        115                 120
```

<210> SEQ ID NO 58
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
aggtcaagct gcagcagtct ggacctgagc tggtgaagcc tggggcttta gtgaagatat    60
cctgcaaggc ttctggttac accttcacaa gctacgatat aaattgggtg aagcagaggc   120
```

```
ctggacaggg acttgagtgg attggatgga tttatcctgg agatggtagt attaagtaca    180
atgagaaatt caagggcaag gccacactga ctgtagacaa atcctccagc acagcctaca    240
tgcaggtcag cagcctgact tctgagaatt ctgcagtcta tttctgtgca agacgggggg    300
agtatggtaa ctacgagggg gctatggact actggggcca agggaccacg gtcaccgtct    360
cctca                                                               365
```

<210> SEQ ID NO 59
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Val Lys Leu Gln Gln Ser Gly Pro Glu Leu Val Lys Pro Gly Ala Leu
1               5                   10                  15

Val Lys Ile Ser Cys Lys Ala Ser Gly Tyr Thr Phe Thr Ser Tyr Asp
            20                  25                  30

Ile Asn Trp Val Lys Gln Arg Pro Gly Gln Gly Leu Glu Trp Ile Gly
        35                  40                  45

Trp Ile Tyr Pro Gly Asp Gly Ser Ile Lys Tyr Asn Glu Lys Phe Lys
    50                  55                  60

Gly Lys Ala Thr Leu Thr Val Asp Lys Ser Ser Ser Thr Ala Tyr Met
65                  70                  75                  80

Gln Val Ser Ser Leu Thr Ser Glu Asn Ser Ala Val Tyr Phe Cys Ala
                85                  90                  95

Arg Arg Gly Glu Tyr Gly Asn Tyr Glu Gly Ala Met Asp Tyr Trp Gly
            100                 105                 110

Gln Gly Thr Thr Val Thr Val Ser Ser
        115                 120

<210> SEQ ID NO 60
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
aggtgcagct gcaggagtct ggacctgagc tggtgaagcc tggggcttta gtgaagatat     60
cctgcaaggc ttctggttac accttcacaa gctacgatat aaattgggtg aagcagaggc    120
ctggacaggg acttgagtgg attggatgga tttatcctgg agatggtagt attaagtaca    180
atgagaaatt caagggcaag gccacactga ctgtagacaa atcctccagc acagcctaca    240
tgcaggtcag cagcctgact tctgagaatt ctgcagtcta tttctgtgca agacgggggg    300
agtatggtaa ctacgagggg gctatggact actggggcca agggaccacg gtcaccgtct    360
cctca                                                               365
```

<210> SEQ ID NO 61
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 61

Val Gln Leu Gln Glu Ser Gly Pro Glu Leu Val Lys Pro Gly Ala Leu
1               5                   10                  15

Val Lys Ile Ser Cys Lys Ala Ser Gly Tyr Thr Phe Thr Ser Tyr Asp
            20                  25                  30

Ile Asn Trp Val Lys Gln Arg Pro Gly Gln Gly Leu Glu Trp Ile Gly
        35                  40                  45

Trp Ile Tyr Pro Gly Asp Gly Ser Ile Lys Tyr Asn Glu Lys Phe Lys
    50                  55                  60

Gly Lys Ala Thr Leu Thr Val Asp Lys Ser Ser Thr Ala Tyr Met
65                  70                  75                  80

Gln Val Ser Ser Leu Thr Ser Glu Asn Ser Ala Val Tyr Phe Cys Ala
                85                  90                  95

Arg Arg Gly Glu Tyr Gly Asn Tyr Glu Gly Ala Met Asp Tyr Trp Gly
            100                 105                 110

Gln Gly Thr Thr Val Thr Val Ser Ser
        115                 120

<210> SEQ ID NO 62
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
aggtgaagct gcagcagtct ggacctgagc tggtgaagcc tggggcttta gtgaagatat    60
cctgcaaggc ttctggttac accttcacaa gctacgatat aaattgggtg aagcagaggc   120
ctggacaggg acttgagtgg attggatgga tttatcctgg agatggtagt attaagtaca   180
atgagaaatt caagggcaag gccacactga ctgtagacaa atcctccagc acagcctaca   240
tgcaggtcag cagcctgact tctgagaatt ctgcagtcta tttctgtgca agacgggggg   300
agtatggtaa ctacgagggg gctatggact actggggcca agggaccacg gtcaccgtct   360
cctca                                                               365

<210> SEQ ID NO 63
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Val Lys Leu Gln Gln Ser Gly Pro Glu Leu Val Lys Pro Gly Ala Leu
1               5                   10                  15

Val Lys Ile Ser Cys Lys Ala Ser Gly Tyr Thr Phe Thr Ser Tyr Asp
            20                  25                  30

Ile Asn Trp Val Lys Gln Arg Pro Gly Gln Gly Leu Glu Trp Ile Gly
        35                  40                  45

Trp Ile Tyr Pro Gly Asp Gly Ser Ile Lys Tyr Asn Glu Lys Phe Lys
    50                  55                  60

Gly Lys Ala Thr Leu Thr Val Asp Lys Ser Ser Thr Ala Tyr Met
65                  70                  75                  80

Gln Val Ser Ser Leu Thr Ser Glu Asn Ser Ala Val Tyr Phe Cys Ala
                85                  90                  95

```
Arg Arg Gly Glu Tyr Gly Asn Tyr Glu Gly Ala Met Asp Tyr Trp Gly
            100                 105                 110

Gln Gly Thr Thr Val Thr Val Ser Ser
        115                 120

<210> SEQ ID NO 64
<211> LENGTH: 365
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
aggtgcagct gcagcagtca ggacctgaac tggtgaagcc tggggcttta gtgaagatat    60
cctgcaaggc ttctggttac accttcacaa gctacgatat aaattgggtg aagcagaggc   120
ctggacaggg acttgagtgg attggatgga tttatcctgg agatggtagt attaagtaca   180
atgagaaatt caagggcaag gccacactga ctgtagacaa atcctccagc acagcctaca   240
tgcaggtcag cagcctgact tctgagaatt ctgcagtcta tttctgtgca agacgggggg   300
agtatggtaa ctacgagggg gctatggact actggggcca aggaccacg gtcaccgtct    360 cctca                                                               365

<210> SEQ ID NO 65
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Val Gln Leu Gln Gln Ser Gly Pro Glu Leu Val Lys Pro Gly Ala Leu
1               5                   10                  15

Val Lys Ile Ser Cys Lys Ala Ser Gly Tyr Thr Phe Thr Ser Tyr Asp
            20                  25                  30

Ile Asn Trp Val Lys Gln Arg Pro Gly Gln Gly Leu Glu Trp Ile Gly
        35                  40                  45

Trp Ile Tyr Pro Gly Asp Gly Ser Ile Lys Tyr Asn Glu Lys Phe Lys
    50                  55                  60

Gly Lys Ala Thr Leu Thr Val Asp Lys Ser Ser Ser Thr Ala Tyr Met
65                  70                  75                  80

Gln Val Ser Ser Leu Thr Ser Glu Asn Ser Ala Val Tyr Phe Cys Ala
                85                  90                  95

Arg Arg Gly Glu Tyr Gly Asn Tyr Glu Gly Ala Met Asp Tyr Trp Gly
            100                 105                 110

Gln Gly Thr Thr Val Thr Val Ser Ser
        115                 120

<210> SEQ ID NO 66
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
gacattgtgc tgacccagtc tccagcttct ttggctgtgt ctctagggca gagggccacc    60
```

```
atctcctgca aggccagcca aagtgttgat tatgatggtc atagttatat gaactggtac    120
caacagaaac caggacagcc acccaaactc ctcatctatg ctgcatccaa tctagaatct    180
gggatcccag ccaggtttag tggcagtggg tctgggacag acttcaccct caacatccat    240
cctgtggagg aggaggatgc tgcaacctat tactgtcagc aaagtgatga aaatcccctc    300
acgttcggta ctgggaccaa gctggagctg aaacgg                              336
```

<210> SEQ ID NO 67
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 67

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly His Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asp
                85                  90                  95

Glu Asn Pro Leu Thr Phe Gly Thr Gly Thr Lys Leu Glu Leu Lys Arg
            100                 105                 110

<210> SEQ ID NO 68
<211> LENGTH: 365
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 68

```
aggtgaagct gcagcagtct ggacctgagc tggtgaagcc tggggcttta gtgaagatat    60
cctgcaaggc ttctggttac accttcacaa gctacgatat aaattgggtg aagcagaggc    120
ctggacaggg acttgagtgg attggatgga tttatcctgg agatggtagt attaagtaca    180
atgagaaatt caagggcaag gccacactga ctgtagacaa atcctccagc acagcctaca    240
tgcaggtcag cagcctgact tctgagaatt ctgcagtcta tttctgtgca agacgggggg    300
agtatggtaa ctacgagggg gctatggact actggggcca agggaccacg gtcaccgtct    360
cctca                                                                365
```

<210> SEQ ID NO 69
<211> LENGTH: 121
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 69

```
Val Lys Leu Gln Gln Ser Gly Pro Glu Leu Val Lys Pro Gly Ala Leu
1               5                   10                  15

Val Lys Ile Ser Cys Lys Ala Ser Gly Tyr Thr Phe Thr Ser Tyr Asp
            20                  25                  30

Ile Asn Trp Val Lys Gln Arg Pro Gly Gln Gly Leu Glu Trp Ile Gly
        35                  40                  45

Trp Ile Tyr Pro Gly Asp Gly Ser Ile Lys Tyr Asn Glu Lys Phe Lys
    50                  55                  60

Gly Lys Ala Thr Leu Thr Val Asp Lys Ser Ser Ser Thr Ala Tyr Met
65                  70                  75                  80

Gln Val Ser Ser Leu Thr Ser Glu Asn Ser Ala Val Tyr Phe Cys Ala
                85                  90                  95

Arg Arg Gly Glu Tyr Gly Asn Tyr Glu Gly Ala Met Asp Tyr Trp Gly
                100                 105                 110

Gln Gly Thr Thr Val Thr Val Ser Ser
                115                 120
```

<210> SEQ ID NO 70
<211> LENGTH: 365
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 70

```
aggtgcagct gcagcagtca ggacctgaac tggtgaagcc tggggcttta gtgaagatat      60
cctgcaaggc ttctggttac accttcacaa gctacgatat aaattgggtg aagcagaggc     120
ctggacaggg acttgagtgg attggatgga tttatcctgg agatggtagt attaagtaca     180
atgagaaatt caagggcaag gccacactga ctgtagacaa atcctccagc acagcctaca     240
tgcaggtcag cagcctgact tctgagaatt ctgcagtcta tttctgtgca agacgggggg     300
agtatggtaa ctacgagggg gctatggact actggggcca agggaccacg gtcaccgtct     360
cctca                                                                 365
```

<210> SEQ ID NO 71
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

```
Val Gln Leu Gln Gln Ser Gly Pro Glu Leu Val Lys Pro Gly Ala Leu
1               5                   10                  15

Val Lys Ile Ser Cys Lys Ala Ser Gly Tyr Thr Phe Thr Ser Tyr Asp
            20                  25                  30

Ile Asn Trp Val Lys Gln Arg Pro Gly Gln Gly Leu Glu Trp Ile Gly
        35                  40                  45

Trp Ile Tyr Pro Gly Asp Gly Ser Ile Lys Tyr Asn Glu Lys Phe Lys
    50                  55                  60

Gly Lys Ala Thr Leu Thr Val Asp Lys Ser Ser Ser Thr Ala Tyr Met
65                  70                  75                  80

Gln Val Ser Ser Leu Thr Ser Glu Asn Ser Ala Val Tyr Phe Cys Ala
                85                  90                  95

Arg Arg Gly Glu Tyr Gly Asn Tyr Glu Gly Ala Met Asp Tyr Trp Gly
```

```
                    100                 105                 110

Gln Gly Thr Thr Val Thr Val Ser Ser
        115                 120

<210> SEQ ID NO 72
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Ser Tyr
            20                  25                  30

Asp Ile Asn Trp Val Lys Gln Arg Pro Gly Gln Gly Leu Glu Trp Ile
        35                  40                  45

Gly Trp Ile Tyr Pro Gly Asp Gly Ser Ile Lys Tyr Asn Glu Lys Phe
    50                  55                  60

Lys Gly Lys Ala Thr Leu Thr Val Asp Lys Ser Ser Ser Thr Ala Tyr
65                  70                  75                  80

Met Gln Val Ser Ser Leu Thr Ser Glu Asn Ser Ala Val Tyr Phe Cys
                85                  90                  95

Ala Arg Arg Gly Glu Tyr Gly Asn Tyr Glu Gly Ala Met Asp Tyr Trp
            100                 105                 110

Gly Gln Gly Thr Thr Val Thr Val Ser Ser
        115                 120

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Ile Val Leu Thr Gln Ser Pro Ala Ser Leu Ala Val Ser Leu Gly
1               5                   10                  15

Gln Arg Ala Thr Ile Ser Ser Lys Ala
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Cys or any naturally occurring amino acid

<400> SEQUENCE: 74

Val Gln Leu Gln Gln Ser Gly Pro Glu Leu Val Lys Pro Gly Ala Leu
1               5                   10                  15

Val Lys Ile Ser Xaa Lys Ala Ser Gly
            20                  25
```

```
<210> SEQ ID NO 75
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly His Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asp
                85                  90                  95

Glu Asn Pro Leu Thr Phe Gly Gly Gly Thr Lys Val Glu Ile Lys
            100                 105                 110

<210> SEQ ID NO 76
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly His Ser Tyr Met Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asp
                85                  90                  95

Glu Asn Pro Leu Thr Phe Gly Gly Gly Thr Lys Val Glu Ile Lys
            100                 105                 110

<210> SEQ ID NO 77
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30
```

```
Gly His Ser Tyr Met Asn Trp Tyr Gln Gln Lys Pro Gly Lys Ala Pro
            35                  40                  45

Lys Leu Leu Ile Tyr Ala Ala Ser Asn Leu Glu Ser Gly Ile Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asp
                 85                  90                  95

Glu Asn Pro Leu Thr Phe Gly Gly Gly Thr Lys Val Glu Ile Lys
                100                 105                 110

<210> SEQ ID NO 78
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Gln Leu Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Asp
                 20                  25                  30

Gly His Ser Tyr Met Asn Trp Tyr Gln Gln Lys Pro Gly Lys Ala Pro
            35                  40                  45

Lys Leu Leu Ile Tyr Ala Ala Ser Asn Leu Glu Ser Gly Ile Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Asp
                 85                  90                  95

Glu Asn Pro Leu Thr Phe Gly Gly Gly Thr Lys Val Glu Ile Lys
                100                 105                 110

<210> SEQ ID NO 79
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Phe Thr Ser Tyr
                 20                  25                  30

Asp Ile Asn Trp Val Arg Gln Ala Pro Gly Lys Gly Leu Glu Trp Met
            35                  40                  45

Gly Trp Ile Tyr Pro Gly Asp Gly Ser Ile Lys Tyr Asn Glu Lys Phe
 50                  55                  60

Lys Gly Arg Val Thr Met Thr Val Asp Lys Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Glu Tyr Gly Asn Tyr Glu Gly Ala Met Asp Tyr Trp
                100                 105                 110
```

```
Gly Gln Gly Thr Leu Val Thr Val Ser Ser
        115                 120
```

<210> SEQ ID NO 80
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30

Asp Ile Asn Trp Val Arg Gln Ala Pro Gly Lys Gly Leu Glu Trp Met
        35                  40                  45

Gly Trp Ile Tyr Pro Gly Asp Gly Ser Ile Lys Tyr Asn Glu Lys Phe
    50                  55                  60

Lys Gly Arg Val Thr Met Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Glu Tyr Gly Asn Tyr Glu Gly Ala Met Asp Tyr Trp
            100                 105                 110

Gly Gln Gly Thr Leu Val Thr Val Ser Ser
        115                 120
```

<210> SEQ ID NO 81
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30

Asp Ile Asn Trp Val Arg Gln Ala Pro Gly Lys Gly Leu Glu Trp Ile
        35                  40                  45

Gly Trp Ile Tyr Pro Gly Asp Gly Ser Ile Lys Tyr Asn Glu Lys Phe
    50                  55                  60

Lys Gly Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Glu Tyr Gly Asn Tyr Glu Gly Ala Met Asp Tyr Trp
            100                 105                 110

Gly Gln Gly Thr Leu Val Thr Val Ser Ser
        115                 120
```

<210> SEQ ID NO 82
<211> LENGTH: 122
<212> TYPE: PRT
<213> ORGANISM: Artificial Sequence -continued

```
<220> FEATURE:
<223> OTHER INFORMATION: Description of Artificial Sequence: Synthetic
      polypeptide

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Tyr
            20                  25                  30

Asp Ile Asn Trp Val Arg Gln Ala Pro Gly Lys Gly Leu Glu Trp Ile
        35                  40                  45

Gly Trp Ile Tyr Pro Gly Asp Gly Ser Ile Lys Tyr Asn Glu Lys Phe
    50                  55                  60

Lys Gly Lys Ala Thr Leu Thr Val Asp Lys Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Glu Tyr Gly Asn Tyr Glu Gly Ala Met Asp Tyr Trp
            100                 105                 110

Gly Gln Gly Thr Leu Val Thr Val Ser Ser
        115                 120

<210> SEQ ID NO 83
<211> LENGTH: 15
<212> TYPE: PRT
<213> ORGANISM: Mus sp.

<400> SEQUENCE: 83

Lys Ala Ser Gln Ser Val Asp Tyr Asp Gly His Ser Tyr Met Asn
1               5                   10                  15
```